(12) United States Patent
Gerlach et al.

(10) Patent No.: US 8,394,801 B2
(45) Date of Patent: Mar. 12, 2013

(54) QUINOXALINE DERIVATIVES AND THEIR USE FOR TREATING BENIGN AND MALIGNANT TUMOUR DISORDERS

(75) Inventors: Matthias Gerlach, Brachttal (DE); Irene Seipelt, Offenbach (DE); Eckhard Guenther, Maintal (DE); Tilmann Schuster, Grossostheim (DE); Emmanuel Polymeropoulos, Frankfurt am Main (DE); Michael Czech, Frankfurt am Main (DE); Eckhard Claus, Frankfurt am Main (DE)

(73) Assignee: Aeterna Zentaris GmbH, Frankfurt am Main (DE)

( * ) Notice: Subject to any disclaimer, the term of this patent is extended or adjusted under 35 U.S.C. 154(b) by 0 days.

(21) Appl. No.: 12/731,243

(22) Filed: Mar. 25, 2010

(65) Prior Publication Data
US 2010/0266538 A1    Oct. 21, 2010

Related U.S. Application Data

(60) Provisional application No. 61/165,953, filed on Apr. 2, 2009.

(30) Foreign Application Priority Data

Apr. 2, 2009   (EP) .................................. 09157141

(51) Int. Cl.
*A61K 31/495* (2006.01)
(52) U.S. Cl. ........ 514/249; 544/116; 544/356; 546/245; 546/268.1; 548/373.1; 549/59
(58) Field of Classification Search .................. 514/249; 544/116, 356; 546/245, 268.1; 548/373.1; 549/59
See application file for complete search history.

(56) References Cited

U.S. PATENT DOCUMENTS
7,067,506 B2 *   6/2006   Keegan et al. ................ 514/183

FOREIGN PATENT DOCUMENTS
| EP | 1990342 | 11/2008 |
| WO | 2003/101444 | 12/2003 |
| WO | 2008/141065 | 11/2008 |

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
Vippagunta, et al. Advanced Drug Delivery Reviews, 48, 2001, 18.*
Chawla, et al. Curr. Res. & Info. Pharm. Sci. (CRIPS), 5, 1, 2004, 9-12.*
Koziol, et al. Justus Liebigs Annalen der Chemie, 7-8, 1976, 1276-1288.*
International Search Report, International Application No. PCT/EP2010/053891.

* cited by examiner

*Primary Examiner* — Douglas M Willis
(74) *Attorney, Agent, or Firm* — Oblon, Spivak, McClelland, Maier & Neustadt, L.L.P.

(57) ABSTRACT

The invention provides quinoxalines of the general formula I which are used as medicaments preferably for treating tumour disorders, in particular in cases of drug resistance to other active compounds and in cases of metastasic carcinoma. The possible applications are not limited to tumour disorders.

Formula I

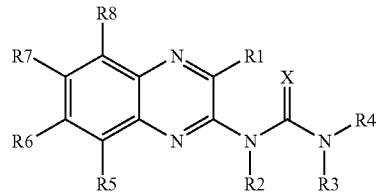

12 Claims, No Drawings

QUINOXALINE DERIVATIVES AND THEIR USE FOR TREATING BENIGN AND MALIGNANT TUMOUR DISORDERS

REFERENCE TO PRIOR APPLICATIONS

This application claims priority to U.S. provisional application Ser. No. 61/165,953, filed Apr. 2, 2009; and to European patent application 09157141.4, filed Apr. 2, 2009, both incorporated herein by reference.

TECHNICAL FIELD

The present invention relates to quinoxaline derivatives, their preparation and their use as medicaments, in particular for treating benign and malignant tumours in humans and other mammals.

STATE OF THE ART

For the next few years, a dramatic increase in oncoses and tumour-related deaths is expected worldwide. In 2001, worldwide approximately 10 million people were suffering from cancer and over 6 million people died from this disease. The development of tumours is a fundamental disease of higher organisms in the plant kingdom, in the animal kingdom and in humans. The generally recognized multistep model of carcinogenesis assumes that as a result of the accumulation of a number of mutations in an individual cell it is so modified in its proliferation and differentiation behaviour that finally, via benign intermediate stages, a malignant state with metastasis is reached. Behind the term cancer or tumour, a clinical picture with more than 200 different individual diseases is hidden. Oncoses can proceed in a benign or malignant manner. The most important tumours are those of the lung, the breast, the stomach, the cervix, the prostate, the head and neck, the large and small intestine, the liver and the blood system. There are great differences with respect to course, prognosis and response to therapy. More than 90% of the cases recognized relate to solid tumours, which in particular in the advanced stages or on metastasis are at present treatable with difficulty or untreatable. The three pillars of cancer control are still surgical removal, irradiation and chemotherapy. In spite of great advances it has still not been possible to develop medicaments which bring about a marked prolongation of the survival time or even a complete cure in the widespread solid tumours. It is therefore meaningful to invent novel medicaments for the control of cancer.

Quinoxaline derivatives are finding many applications in pharmaceutical industry as pharmacodynamically active compounds and as building blocks for syntheses.

Quinoxaline derivatives are described in the document WO08/141065 A1 as PI3K inhibitors, in the patent US2007/0254894 as angiogenesis inhibitors, in the patent WO08/015423 as CHK inhibitors, in the patents WO9854156, WO9854157, WO9854158, WO2000031049, WO2000031050 and WO2000031051 as PDGF and Lck-tyrosine kinase inhibitors, in the patents WO9962887 and WO9732858 as glutamate receptor antagonists. The literature reference J. Med. Chem. 2001, 44, 1758 describes the synthesis of XK469 derivatives with quinoxaline structure and their use as antitumour agents, the literature reference Cancer Research 1996, 3540 describes quinoxalines as Flk-1 inhibitors and J. Med. Chem. 1981, 24, 93 describes the preparation of CNS-active quinoxalines.

DESCRIPTION OF THE INVENTION

The present invention relates to quinoxaline derivatives of the general formula I, to their preparation and to their use as medicaments, in particular for treating benign and malignant tumours in humans and other mammals.

Surprisingly, it has now been found that in particular quinoxaline derivatives having a urea or thiourea group have excellent cytotoxic activity in various human tumour cell lines. In nanomolar concentrations, they inhibit the division inter alia of intestinal carcinoma cells, ovarial carcinoma cells, prostate carcinoma cells, uterus carcinoma cells, glioblastoma cells, lung carcinoma cells, leukaemia cells and breast cancer cells. The quinoxalines according to the invention having a urea or thiourea group are highly active in particular also against cell lines resistant to cis-platin, doxorubicin and vincristine. The present invention demonstrates that the quinoxalines of the general structure I are highly potent with respect to the biological action, and that use as an active compound in a medicament for controlling cancerous disorders is therefore possible.

It is an object of the present invention to provide cytotoxic substances suitable for treating a large number of tumours, in particular in cases of resistence to other medicaments and in cases of metastasic carcinoma.

This object is achieved by quinoxaline derivatives of the general formula I

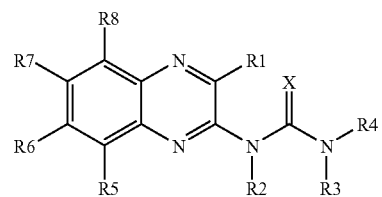

Formula I in which
X is: oxygen or sulphur;
$R_1$ is:
  (i) hydrogen,
  (ii) unsubstituted or substituted $(C_1-C_{12})$-alkyl,
  (iii) cyano,
  (iv) halogen,
$R_2/R_3$ are:
  (i) hydrogen,
  (ii) unsubstituted or substituted $(C_1-C_{12})$-alkyl,
$R_4$ is:
  (i) hydrogen,
  (ii) unsubstituted or substituted $(C_1-C_{12})$-alkyl,
  (iii) unsubstituted or substituted cycloalkyl,
  (iv) unsubstituted or substituted heterocyclyl,
  (v) unsubstituted or substituted aryl,
  (vi) unsubstituted or substituted heteroaryl,
  (vii) unsubstituted or substituted alkylaryl,
  (viii) unsubstituted or substituted alkylheteroaryl,
and
$R_5-R_8$ are:
  (i) hydrogen,
  (ii) unsubstituted or substituted $(C_1-C_{12})$-alkyl,
  (iii) unsubstituted or substituted aryl,
  (iv) unsubstituted or substituted heteroaryl,
  (v) halogen,
  (vi) cyano,
  (vii) hydroxyl,
  (viii) $(C_1-C_{12})$-alkoxy,
  (ix) amino,
  (x) carboxyl, alkoxycarbonyl, carboxyalkyl or alkoxycarbonylalkyl, (xi) alkoxycarbonylamino, alkoxycarbonylaminoalkyl, and where at least one of the substituents $R_5$-$R_8$ has to be an unsubstituted or substituted aryl or heteroaryl radical.

Some of the terms used in the description and in the patent claims are defined below.

The term "alkyl" includes for the purpose of this invention acyclic saturated or unsaturated hydrocarbon radicals which may be branched or straight-chain, having 1 to 12 C atoms, i.e. $C_{1-12}$-alkanyls, $C_{2-12}$-alkenyls and $C_{2-12}$-alkynyls. In this connection, alkenyls have at least one C=C double bond and alkynyls have at least one C=C triple bond. Alkyl is preferably selected from the group comprising methyl, ethyl, n-propyl, 2-propyl, n-butyl, sec-butyl, tert-butyl, n-pentyl, isopentyl, neopentyl, n-hexyl, 2-hexyl, n-octyl, ethylenyl (vinyl), ethynyl, propenyl (—CH$_2$CH=CH$_2$; —CH=CH—CH$_3$, —C(=CH$_2$)—CH$_3$), propynyl (—CH$_2$—C≡CH, —C≡C—CH$_3$), butenyl, butynyl, pentenyl, pentynyl, hexenyl, hexynyl, heptenyl, heptynyl, octenyl and octynyl.

The term "cycloalkyl" means for the purposes of this invention cyclic hydrocarbons having 3-12 carbon atoms, which may be saturated or unsaturated. It is possible for the linkage to the compounds of the general structure I to take place via any possible ring member of the cycloalkyl radical. The cycloalkyl radical may also be part of a bi- or polycyclic system.

The term "heterocyclyl" stands for a 3-, 4-, 5-, 6-, 7- or 8-membered cyclic organic radical which comprises at least 1, where appropriate 2, 3, 4 or 5, heteroatoms, the heteroatoms being identical or different and the cyclic radical being saturated or unsaturated, but not aromatic. It is possible for the linkage to the compounds of the general structure I to take place via any possible ring member of the heterocyclyl radical. The heterocycle may also be part of a bi- or polycyclic system. Preferred heteroatoms are nitrogen, oxygen and sulphur. It is preferred for the heterocyclyl radical to be selected from the group comprising tetrahydrofuryl, tetrahydropyranyl, pyrrolidinyl, piperidinyl, piperazinyl and morpholinyl.

The term "aryl" means for the purpose of this invention aromatic hydrocarbons having 6 to 14 carbon atoms, inter alia phenyls, naphthyls and anthracenyls. The radicals may also be fused to other saturated, (partially) unsaturated or aromatic ring systems. It is possible for the linkage to the compounds of the general structure I to take place via any possible ring member of the aryl radical.

The term "heteroaryl" stands for a 5-, 6- or 7-membered cyclic aromatic radical which comprises at least 1, where appropriate also 2, 3, 4 or 5, heteroatoms, the heteroatoms being identical or different. It is possible for the linkage to the compounds of the general structure I to take place via any possible ring member of the heteroaryl radical. The heterocycle may also be part of a bi- or polycyclic system. Preferred heteroatoms are nitrogen, oxygen and sulphur. It is preferred for the heteroaryl radical to be selected from the group comprising pyrrolyl, furyl, thienyl, thiazolyl, oxazolyl, isoxazolyl, pyrazolyl, imidazolyl, pyridinyl, pyrimidinyl, pyridazinyl, pyrazinyl, phthalazinyl, indolyl, indazolyl, indolizinyl, quinolinyl, isoquinolinyl, quinoxalinyl, quinazolinyl, carbazolyl, phenazinyl, phenothiazinyl, acridinyl.

The terms "alkylaryl" or "alkylheteroaryl" means for the purposes of the present invention that alkyl, aryl and heteroaryl have the meanings defined above, and the aryl or heteroaryl radical is linked via a $C_{1-8}$-alkyl group to the compounds of the general structure I.

In the context of "alkyl", "cycloalkyl", "heterocyclyl", "aryl", "heteroaryl", "alkylaryl" and "alkylheteroaryl", the term "substituted", in the sense of the present invention, unless explicitly defined above in the description or in the claims, is to be understood as meaning the substitution of one or more hydrogen radicals by F, Cl, Br, I, CN, CF$_3$, NH$_2$, NH-alkyl, NH-aryl, N(alkyl)$_2$, NH—CO-alkyl, NH—CO-aryl, NH—CO-heteroaryl, NH—SO$_2$-alkyl, NH—SO$_2$-aryl, NH—SO$_2$-heteroaryl, NH—CO—NH-alkyl, NH—CO—NH-aryl, NH—CO—NH-heteroaryl, NH—C(O)O-alkyl, NH—C(O)O-aryl, NH—C(O)O-heteroaryl, NO$_2$, SH, S-alkyl, OH, OCF$_3$, O-alkyl, O-aryl, O—CO-alkyl, O—CO-aryl, O—CO-heteroaryl, O—C(O)O-alkyl, O—C(O)O-aryl, O—C(O)O-heteroaryl, O—CO—NH-alkyl, O—CO—N(alkyl)$_2$, —O—CO—NH-aryl, O—CO—NH-heteroaryl, OSO$_3$H, OSO$_2$-alkyl, OSO$_2$-aryl, OSO$_2$-heteroaryl, OP(O)(OH)$_2$, alkyl-P(O)(OH)$_2$ CHO, CO$_2$H, C(O)O-alkyl, C(O)O-aryl, C(O)O-heteroaryl, CO-alkyl, CO-aryl, CO-heteroaryl, SO$_3$H, SO$_2$—NH$_2$, SO$_2$—NH-alkyl, SO$_2$—NH-aryl, SO$_2$—NH-heteroaryl, alkyl, cycloalkyl, heterocyclyl, aryl or heteroaryl, where the radicals "alkyl", "cycloalkyl", "heterocyclyl", "aryl" or "heteroaryl" may also be substituted. The substituents can be identical or different, and the substitution can be in any possible position of the alkyl, cycloalkyl, heterocyclyl, aryl and heteroaryl radical.

Polysubstituted radicals are to be understood as radicals which are polysubstituted, for example di- or trisubstituted, either at different or on the same atoms, for example trisubstituted at the same carbon atom as in the case of CF$_3$, —CH$_2$CF$_3$ or at different positions as in the case of —CH(OH)—CH=CH—CHCl$_2$.

Polysubstitution can be by identical or different substituents.

If the compounds of the general formula I according to the invention have at least one centre of asymmetry, they can be present in the form of their racemates, in the form of the pure enantiomers and/or diastereomers or in the form of mixtures of these enantiomers and/or diastereomers. The mixtures can be present in any desired mixing ratio of the stereoisomers.

Thus, for example, the compounds of the general formula I according to the invention which have one or more centres of chirality and which occur as racemates can be separated into their optical isomers, that is enantiomers or diastereomers, by methods known per se. The separation can be carried out by column separation on chiral phases or by recrystallization from an optically active solvent or using an optically active acid or base or by derivatization with an optically active reagent, such as, for example, an optically active alcohol, and subsequent removal of the radical.

If possible, the compounds according to the invention can be present in the form of the tautomers.

The compounds of the general formula I according to the invention can, if they have a sufficiently basic group, such as, for example, a primary, secondary or tertiary amine, be converted into their physiologically acceptable salts using inorganic and organic acids. Preferably, the pharmaceutically acceptable salts of the compounds of the general structure I according to the invention are formed with hydrochloric acid, hydrobromic acid, sulphuric acid, phosphoric acid, methanesulphonic acid, p-toluenesulphonic acid, carbonic acid, formic acid, acetic acid, trifluoroacetic acid, sulphoacetic acid, oxalic acid, malonic acid, maleic acid, succinic acid, tartaric acid, racemic acid, malic acid, embonic acid, mandelic acid, fumaric acid, lactic acid, citric acid, glutamic acid or aspartic acid. The salts formed are, inter alia, hydrochlorides, hydrobromides, sulphates, hydrogensulphates, phosphates, methanesulphonates, tosylates, carbonates, bicarbonates, formates, acetates, triflates, sulphoacetates, oxalates, malonates, maleates, succinates, tartrates, malates, embonates, mandelates, fumarates, lactates, citrates, glutamates and aspartates. The stoichiometry of the salts formed of the compounds according to the invention can in this case be an integral or nonintegral multiple of one.

The compounds of the general formula I according to the invention can, if they contain a sufficiently acidic group, such as, for example, the carboxyl group, be converted into their physiologically acceptable salts with inorganic and organic bases. Suitable inorganic bases are, for example, sodium hydroxide, potassium hydroxide, calcium hydroxide, suitable organic bases are ethanolamine, diethanolamine, triethanolamine, cyclohexylamine, dibenzylethylenediamine and lysine. The stoichiometry of the salts formed of the compounds according to the invention can in this case be an integral or nonintegral multiple of one.

Preference is also given to solvates and in particular hydrates of the compounds according to the invention which can be obtained, for example, by crystallization from a solvent or from aqueous solution. Here, one, two, three or any number of solvate or water molecules or integral fractions thereof may bind to the compounds according to the invention forming solvates and hydrates.

It is known that chemical substances form solids which are present in various atomic states, which are described as polymorphic forms or modifications. The different modifications of a polymorphic substance can differ greatly in their physical properties. The compounds of the general formula I according to the invention can be present in various polymorphic forms, where certain modifications may be metastable.

Most preference is given to compounds of the general formula I which are chosen from the following selection:
1-cyclopentyl-3-[7-(4-hydroxy-3-methoxyphenyl)quinoxalin-2-yl]urea (1)
1-cyclohexyl-3-[7-(4-hydroxy-3-methoxyphenyl)quinoxalin-2-yl]urea (2)
1-cyclohexyl-3-[7-(3,4-dimethoxyphenyl)quinoxalin-2-yl]urea (3)
1-[7-(3,4-dimethoxyphenyl)quinoxalin-2-yl]-3-[1-(2,2,2-trifluoroacetyl)piperidin-4-yl]urea (4)
1-[7-(4-hydroxy-3-methoxyphenyl)quinoxalin-2-yl]-3-phenylurea (5)
1-[7-(4-hydroxy-3-methoxyphenyl)quinoxalin-2-yl]-3-[1-(2,2,2-trifluoroacetyl)piperidin-4-yl]urea (6)
1-benzyl-3-[7-(4-hydroxy-3-methoxyphenyl)quinoxalin-2-yl]urea (7)
1-cyclopentyl-3-[7-(3,4-dimethoxyphenyl)quinoxalin-2-yl]urea (8)
1-tert-butyl-3-[7-(4-hydroxy-3,5-dimethylphenyl)quinoxalin-2-yl]urea (9)
1-tert-butyl-3-[7-(4-hydroxy-3-methoxyphenyl)quinoxalin-2-yl]urea (10)
1-[7-(4-hydroxy-3-methoxyphenyl)quinoxalin-2-yl]-3-thiophen-2-ylurea (11)
1-cyclohexyl-3-[7-(4-hydroxy-3,5-dimethylphenyl)quinoxalin-2-yl]urea (12)
1-cyclopentyl-3-[7-(4-hydroxy-3,5-dimethylphenyl)quinoxalin-2-yl]urea (13)
1-[7-(4-hydroxy-3,5-dimethylphenyl)quinoxalin-2-yl]-3-phenylurea (14)
1-[7-(4-hydroxy-3,5-dimethylphenyl)quinoxalin-2-yl]-3-thiophen-2-ylurea (15)
1-[7-(4-hydroxy-3,5-dimethylphenyl)quinoxalin-2-yl]-3-methylurea (16)
1-[7-(4-hydroxy-3,5-dimethylphenyl)quinoxalin-2-yl]-3-isopropylurea (17)
1-butyl-3-[7-(4-hydroxy-3,5-dimethylphenyl)quinoxalin-2-yl]urea (18)
1-ethyl-3-[7-(4-hydroxy-3,5-dimethylphenyl)quinoxalin-2-yl]urea (19)
1-cyclohexyl-3-[7-(4-hydroxy-3,5-dimethylphenyl)quinoxalin-2-yl]thiourea (20)
1-cyclohexyl-3-[7-(3,5-dichloro-4-hydroxyphenyl)quinoxalin-2-yl]thiourea (21)
1-ethyl-3-[7-(4-hydroxy-3,5-dimethylphenyl)quinoxalin-2-yl]thiourea (22)
1-cyclopropyl-3-[7-(4-hydroxy-3,5-dimethylphenyl)quinoxalin-2-yl]thiourea (23)
1-cyclopentyl-3-[7-(4-hydroxy-3,5-dimethylphenyl)quinoxalin-2-yl]thiourea (24)
1-tert-butyl-3-[7-(4-hydroxy-3,5-dimethylphenyl)quinoxalin-2-yl]thiourea (25)
1-dodecyl-3-(7-phenylquinoxalin-2-yl)urea (26)
1-(3-chloro-2-methylphenyl)-3-(7-phenylquinoxalin-2-yl)urea (27)
1-(3,4-dimethylphenyl)-3-(7-phenylquinoxalin-2-yl)urea (28)
1-allyl-3-(7-phenylquinoxalin-2-yl)urea (29)
1-cyclopentyl-3-(7-phenylquinoxalin-2-yl)urea (30)
1-[7-(4-hydroxy-3,5-dimethylphenyl)quinoxalin-2-yl]-3-isopropylthiourea (31)
1-butyl-3-[7-(4-hydroxy-3,5-dimethylphenyl)quinoxalin-2-yl]thiourea (32)
1-[7-(4-hydroxy-3,5-dimethylphenyl)quinoxalin-2-yl]-3-pentylurea (33)
1-cyclobutyl-3-[7-(4-hydroxy-3,5-dimethylphenyl)quinoxalin-2-yl]thiourea (34)
1-hexyl-3-[7-(4-hydroxy-3,5-dimethylphenyl)quinoxalin-2-yl]urea (35)
1-[7-(4-hydroxy-3,5-dimethylphenyl)quinoxalin-2-yl]-3-propylurea (36)
1-dodecyl-3-[7-(4-hydroxy-3,5-dimethylphenyl)quinoxalin-2-yl]urea (37)
1-(3-chloro-2-methylphenyl)-3-[7-(4-hydroxy-3,5-dimethylphenyl)quinoxalin-2-yl]urea (38)
1-(3-acetylphenyl)-3-[7-(4-hydroxy-3,5-dimethylphenyl)quinoxalin-2-yl]urea (39)
1-(3,4-dimethylphenyl)-3-[7-(4-hydroxy-3,5-dimethylphenyl)quinoxalin-2-yl]urea (40)
1-allyl-3-[7-(4-hydroxy-3,5-dimethylphenyl)quinoxalin-2-yl]urea (41)
1-cyclooctyl-3-[7-(4-hydroxy-3,5-dimethylphenyl)quinoxalin-2-yl]urea (42)
1-(2,4-dimethylphenyl)-3-[7-(4-hydroxy-3,5-dimethylphenyl)quinoxalin-2-yl]urea (43)
1-cyclooctyl-3-[7-(4-hydroxy-3-methoxyphenyl)quinoxalin-2-yl]urea (44)
1-adamantan-1-yl-3-(7-phenylquinoxalin-2-yl)urea (45)
1-[7-(4-hydroxy-3,5-dimethylphenyl)quinoxalin-2-yl]-3-p-tolylurea (46)
1-(3,4-dichlorophenyl)-3-[7-(4-hydroxy-3,5-dimethylphenyl)quinoxalin-2-yl]urea (47)
1-[7-(4-hydroxy-3,5-dimethylphenyl)quinoxalin-2-yl]-3-(4-methoxyphenyl)urea (48)
1-adamantan-1-yl-3-[7-(4-hydroxy-3,5-dimethylphenyl)quinoxalin-2-yl]urea (49)
1-[7-(4-hydroxy-3,5-dimethylphenyl)quinoxalin-2-yl]-3-naphthalen-2-ylurea (50)
1-[7-(4-hydroxy-3,5-dimethylphenyl)quinoxalin-2-yl]-3-(1,1,3,3-tetramethylbutyl)urea (51)
1-[7-(4-hydroxy-3,5-dimethylphenyl)quinoxalin-2-yl]-3-pyridin-3-ylurea (52)
1-((R)-1,2-dimethylpropyl)-3-[7-(4-hydroxy-3,5-dimethylphenyl)quinoxalin-2-yl]urea (53)

1-((S)-1,2-dimethylpropyl)-3-[7-(4-hydroxy-3,5-dimethylphenyl)quinoxalin-2-yl]urea (54)
1-(5-chloro-2-methylphenyl)-3-[7-(4-hydroxy-3,5-dimethylphenyl)quinoxalin-2-yl]urea (55)
1-((S)-2-phenylcyclopropyl)-3-(7-phenylquinoxalin-2-yl)urea (56)
1-[7-(4-hydroxy-3,5-dimethylphenyl)quinoxalin-2-yl]-3-((S)-2-phenylcyclopropyl)urea (57)
1-(2-chloro-6-methylphenyl)-3-[7-(4-hydroxy-3,5-dimethylphenyl)quinoxalin-2-yl]urea (58)
1-allyl-3-[7-(4-hydroxy-3-methoxyphenyl)quinoxalin-2-yl]urea (D-118068) (59)
1-(3,5-dimethylisoxazol-4-yl)-3-[7-(4-hydroxy-3,5-dimethylphenyl)quinoxalin-2-yl]urea (60)
1-sec-butyl-3-[7-(4-hydroxy-3,5-dimethylphenyl)quinoxalin-2-yl]urea (61)
1-ethyl-3-[7-(4-methoxy-3,5-dimethylphenyl)quinoxalin-2-yl]urea (62)
1-isopropyl-3-[7-(4-methoxy-3,5-dimethylphenyl)quinoxalin-2-yl]urea (63)
1-isopropyl-3-[7-(4-methoxy-3,5-dimethylphenyl)quinoxalin-2-yl]thiourea (64)
1-[7-(4-hydroxy-3,5-dimethylphenyl)quinoxalin-2-yl]-3-isobutylurea (65)
1-(1-ethylpropyl)-3-[7-(4-hydroxy-3,5-dimethylphenyl)quinoxalin-2-yl]urea (66)
1-(2,2-Dimethyl-propyl)-3-[7-(4-hydroxy-3,5-dimethyl-phenyl)-quinoxalin-2-yl]-urea (67)
1-[7-(4-Amino-phenyl)-quinoxalin-2-yl]-3-isopropyl-urea (68)
1-[7-(4-Hydroxy-phenyl)-quinoxalin-2-yl]-3-isopropyl-urea (69)
1-Isopropyl-3-[7-(1-methyl-1H-pyrazol-4-yl)-quinoxalin-2-yl]-urea (70)
1-[7-(3,5-Dichloro-4-hydroxy-phenyl)-quinoxalin-2-yl]-3-pentyl-urea (71)
1-Butyl-3-[7-(3,5-dichloro-4-hydroxy-phenyl)-quinoxalin-2-yl]-urea (72)
1-[7-(3,5-Dichloro-4-hydroxy-phenyl)-quinoxalin-2-yl]-3-propyl-urea (73)
1-[7-(3,5-Dichloro-4-hydroxy-phenyl)-quinoxalin-2-yl]-3-ethyl-urea (74)
1-[7-(3,5-Dichloro-4-hydroxy-phenyl)-quinoxalin-2-yl]-3-heptyl-urea (75)
1-[7-(3,5-Dichloro-4-hydroxy-phenyl)-quinoxalin-2-yl]-3-isopropyl-urea (76)
1-tert-Butyl-3-[7-(3,5-dichloro-4-hydroxy-phenyl)-quinoxalin-2-yl]-urea (77)
1-Cycloheptyl-3-[7-(3,5-dichloro-4-hydroxy-phenyl)-quinoxalin-2-yl]-urea (78)
1-Cyclooctyl-3-[7-(3,5-dichloro-4-hydroxy-phenyl)-quinoxalin-2-yl]-urea (79)
1-Cyclobutyl-3-[7-(3,5-dichloro-4-hydroxy-phenyl)-quinoxalin-2-yl]-thiourea (80)
1-Cyclopentyl-3-[7-(3,5-dichloro-4-hydroxy-phenyl)-quinoxalin-2-yl]-urea (81)
1-[7-(3-Chloro-4-hydroxy-5-methoxy-phenyl)-quinoxalin-2-yl]-3-isopropyl-urea (82)
1-Cyclopropyl-3-[7-(3,5-dichloro-4-hydroxy-phenyl)-quinoxalin-2-yl]-thiourea (83)
1-[7-(3,5-Dichloro-4-hydroxy-phenyl)-quinoxalin-2-yl]-3-(3-phenyl-propyl)-urea (84)
1-[7-(3,5-Dichloro-4-hydroxy-phenyl)-quinoxalin-2-yl]-3-phenethyl-urea (85)
1-[7-(3,5-Dichloro-4-hydroxy-phenyl)-quinoxalin-2-yl]-3-phenyl-urea (86)
1-Butyl-3-[7-(3,5-dichloro-4-hydroxy-phenyl)-quinoxalin-2-yl]-thiourea (87)
1-[7-(3,5-Dichloro-4-hydroxy-phenyl)-quinoxalin-2-yl]-3-ethyl-thiourea (88)
1-[7-(3,5-Dichloro-4-hydroxy-phenyl)-quinoxalin-2-yl]-3-propyl-thiourea (89)
1-[7-(3,5-Dichloro-4-hydroxy-phenyl)-quinoxalin-2-yl]-3-pentyl-thiourea (90)
1-[7-(3,5-Dichloro-4-hydroxy-phenyl)-quinoxalin-2-yl]-3-isopropyl-thiourea (91)
1-Cycloheptyl-3-[7-(3,5-dichloro-4-hydroxy-phenyl)-quinoxalin-2-yl]-thiourea (92)
1-Cyclooctyl-3-[7-(3,5-dichloro-4-hydroxy-phenyl)-quinoxalin-2-yl]-thiourea (93)
1-Benzyl-3-[7-(3,5-dichloro-4-hydroxy-phenyl)-quinoxalin-2-yl]-thiourea (94)
1-[7-(3-Chloro-4-hydroxy-phenyl)-quinoxalin-2-yl]-3-isopropyl-urea (95)
1-[7-(3,5-Dichloro-4-hydroxy-phenyl)-quinoxalin-2-yl]-3-(3-phenyl-propyl)-thiourea (96)
1-[7-(3,5-Dichloro-4-hydroxy-phenyl)-quinoxalin-2-yl]-3-phenethyl-thiourea (97)
1-[2-(4-Chloro-phenyl)-ethyl]-3-[7-(3,5-dichloro-4-hydroxy-phenyl)-quinoxalin-2-yl]-thiourea (98)
1-[7-(3,5-Dichloro-4-hydroxy-phenyl)-quinoxalin-2-yl]-3-(3-morpholin-4-yl-propyl)-thiourea (99)
1-[7-(3,5-Dichloro-4-hydroxy-phenyl)-quinoxalin-2-yl]-3-[2-(3,4-dimethoxy-phenyl)-ethyl]-thiourea (100)
1-(2-Cyclohex-1-enyl-ethyl)-3-[7-(3,5-dichloro-4-hydroxy-phenyl)-quinoxalin-2-yl]-thiourea (101)
1-[7-(3,5-Dichloro-4-hydroxy-phenyl)-quinoxalin-2-yl]-3-(2-thiophen-2-yl-ethyl)-urea (102)
1-[7-(3,5-Dichloro-4-hydroxy-phenyl)-quinoxalin-2-yl]-3-[2-(4-methoxy-phenyl)-ethyl]-thiourea (103)
1-[7-(3,5-Dichloro-4-hydroxy-phenyl)-quinoxalin-2-yl]-3-[2-(4-ethyl-phenyl)-ethyl]-urea (104)
1-[7-(3,5-Dichloro-4-hydroxy-phenyl)-quinoxalin-2-yl]-3-[2-(3,5-dimethoxy-phenyl)-ethyl]-urea (105)
1-[7-(3,5-Dichloro-4-hydroxy-phenyl)-quinoxalin-2-yl]-3-[2-(3,4-dichloro-phenyl)-ethyl]-urea (106)
1-[2-(3-Bromo-4-methoxy-phenyl)-ethyl]-3-[7-(3,5-dichloro-4-hydroxy-phenyl)-quinoxalin-2-yl]-urea (107)
1-(2-Biphenyl-4-yl-ethyl)-3-[7-(3,5-dichloro-4-hydroxy-phenyl)-quinoxalin-2-yl]-urea (108)
1-[7-(3,5-Dichloro-4-hydroxy-phenyl)-quinoxalin-2-yl]-3-[2-(2,3-dimethoxy-phenyl)-ethyl]-urea (109)
1-[7-(3,5-Dichloro-4-hydroxy-phenyl)-quinoxalin-2-yl]-3-[2-(2-fluoro-phenyl)-ethyl]-urea (110)
1-[7-(3,5-Dichloro-4-hydroxy-phenyl)-quinoxalin-2-yl]-3-[2-(2,4-dichloro-phenyl)-ethyl]-urea (111) 1-[7-(3,5-Dichloro-4-hydroxy-phenyl)-quinoxalin-2-yl]-3-[2-(4-fluoro-phenyl)-ethyl]-urea (112)
1-[7-(3,5-Dichloro-4-hydroxy-phenyl)-quinoxalin-2-yl]-3-[2-(3,4-dimethoxy-phenyl)-ethyl]-urea (113)
1-[7-(3,5-Dichloro-4-hydroxy-phenyl)-quinoxalin-2-yl]-3-[2-(4-methoxy-phenyl)-ethyl]-urea (114)
1-[7-(3,5-Dichloro-4-hydroxy-phenyl)-quinoxalin-2-yl]-3-[2-(2,5-dimethoxy-phenyl)-ethyl]-urea (115)
1-[2-(4-Chloro-phenyl)-ethyl]-3-[7-(3,5-dichloro-4-hydroxy-phenyl)-quinoxalin-2-yl]-urea (116)
1-[2-(3-Chloro-phenyl)-ethyl]-3-[7-(3,5-dichloro-4-hydroxy-phenyl)-quinoxalin-2-yl]-urea (117)
1-(2-Cyclopentyl-ethyl)-3-[7-(3,5-dichloro-4-hydroxy-phenyl)-quinoxalin-2-yl]-thiourea (118)
1-(2-Cyclohexyl-ethyl)-3-[7-(3,5-dichloro-4-hydroxy-phenyl)-quinoxalin-2-yl]-urea (119)

1-(2-Cyclohexyl-ethyl)-3-[7-(3,5-dichloro-4-hydroxy-phenyl)-quinoxalin-2-yl]-thiourea (120)

1-[7-(3,5-Dichloro-4-hydroxy-phenyl)-quinoxalin-2-yl]-3-[2-(4-hydroxy-phenyl)-ethyl]-thiourea (121)

1-[7-(3,5-Dichloro-4-hydroxy-phenyl)-quinoxalin-2-yl]-3-(2-pyridin-3-yl-ethyl)-thiourea (122)

The quinoxalines of the general formula I according to the invention are suitable for use in medicaments, in particular as antitumour agents, for the treatment of humans and other mammals. Mammals may be domesticated animals such as horses, cattle, dogs, cats, hares, sheep and the like.

According to a further aspect of the invention there is provided a method for treating tumours in humans and other mammals, characterized in that at least one quinoxaline according to the general formula I is administered to the human or another mammal in a dose effective for the treatment of tumours. The therapeutically effective dose, to be administered for the treatment, of the respective quinoxaline according to the invention depends inter alia on the type and the stage of the tumour disorder, on the age, weight and sex of the patient, on the type of administration and on the duration of the treatment. The medicaments according to the invention can be administered as liquid, semisolid and solid pharmaceutical forms. This takes place in the manner suitable in each case in the form of aerosols, powders, dusting powders and epipastics, tablets including coated tablets, emulsions, foams, solutions, suspensions, gels, ointments, pastes, pills, pastilles, capsules or suppositories.

The pharmaceutical forms comprise besides at least one ingredient of the invention, depending on the pharmaceutical form employed, where appropriate auxiliaries such as, inter alia, solvents, solution promoters, solubilizers, emulsifiers, wetting agents, antifoams, gelling agents, thickeners, film formers, binders, buffers, salt formers, desiccants, flow regulators, fillers, preservatives, antioxidants, colours, mould release agents, lubricants, disintegrants, and masking tastes and odours. The selection of the auxiliaries, and the amounts thereof to be employed, depends on the chosen pharmaceutical form and is based on the formulas known to the skilled person.

The medicaments according to the invention can be administered in a suitable dosage form to the skin, epicutaneously as solution, suspension, emulsion, foam, ointment, paste or plaster; via the oral and lingual mucosa, buccally, lingually or sublingually as tablet, pastille, coated tablet, linctus or gargle; via the gastric and intestinal mucosa, enterally as tablet, coated tablet, capsule, solution, suspension or emulsion; via the rectal mucosa, rectally as suppository, rectal capsule or ointment; via the nasal mucosa, nasally as drops, ointments or spray; via the bronchial and alveolar epithelium, by the pulmonary route or by inhalation as aerosol or inhalant; via the conjunctiva, conjunctivally as eyedrops, eye ointment, eye tablets, lamellae or eye lotion; via the mucosa of the genital organs, intravaginally as vaginal suppositories, ointments and douche, by the intrauterine route as uterine pessary; via the urinary tract, intraurethrally as irrigation, ointment or bougie; into an artery, intraarterially as injection; into a vein, intravenously as injection or infusion, paravenously as injection or infusion; into the skin, intracutaneously as injection or implant; under the skin, subcutaneously as injection or implant; into the muscle, intramuscularly as injection or implant; into the abdominal cavity, intraperitoneally as injection or infusion.

The medicinal effect of the compounds of the invention of the general structure I can be prolonged by suitable measures in the light of practical therapeutic requirements. This aim can be achieved by chemical and/or pharmaceutical means.

Examples of the achievement of a prolongation of the effect are the use of implants, liposomes, delayed-release forms, nanoparticle suspensions and so-called prodrugs of the compounds according to the invention, the formation of salts and complexes of low solubility, or the use of crystal suspensions.

The compounds according to the invention can be employed as individual substances or in combination with other substances such as, for example, asparaginase, bleomycin, carboplatin, carmustine, chlorambucil, cisplatin, colaspase, cyclophosphamide, cytarabine, dacarbazine, dactinomycin, daunorubicin, doxorubicin (adriamycin), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thalidomide, thioguanine, topotecan, vinblastine, vincristine, vindesine, aminoglutethimide, L-asparaginase, azathioprine, 5-azacytidine cladribine, busulphan, diethylstilbestrol, 2',2'-difluorodeoxycytidine, docetaxel, erythrohydroxynonyladenine, ethynylestradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, oxaliplatin, pentostatin, N-phosphonoacetyl-L-aspartate (PALA), plicamycin, semustine, teniposide, testosterone propionate, thiotepa, trimethylmelamine, uridine, vinorelbine, epothilone, gemcitabine, taxotere, BCNU, CCNU, DTIC, herceptin, avastin, erbitux, sorafenib, gleevec, iressa, tarceva, rapamycin, actinomycin D, sunitinib (sutent).

Particular preference is given here to medicaments comprising at least one compound of the following group of quinoxalines:

1-cyclopentyl-3-[7-(4-hydroxy-3-methoxyphenyl)quinoxalin-2-yl]urea (1)

1-cyclohexyl-3-[7-(4-hydroxy-3-methoxyphenyl)quinoxalin-2-yl]urea (2)

1-cyclohexyl-3-[7-(3,4-dimethoxyphenyl)quinoxalin-2-yl]urea (3)

1-[7-(3,4-dimethoxyphenyl)quinoxalin-2-yl]-3-[1-(2,2,2-trifluoroacetyl)piperidin-4-yl]urea (4)

1-[7-(4-hydroxy-3-methoxyphenyl)quinoxalin-2-yl]-3-phenylurea (5)

1-[7-(4-hydroxy-3-methoxyphenyl)quinoxalin-2-yl]-3-[1-(2,2,2-trifluoroacetyl)piperidin-4-yl]urea (6)

1-benzyl-3-[7-(4-hydroxy-3-methoxyphenyl)quinoxalin-2-yl]urea (7)

1-cyclopentyl-3-[7-(3,4-dimethoxyphenyl)quinoxalin-2-yl]urea (8)

1-tert-butyl-3-[7-(4-hydroxy-3,5-dimethylphenyl)quinoxalin-2-yl]urea (9)

1-tert-butyl-3-[7-(4-hydroxy-3-methoxyphenyl)quinoxalin-2-yl]urea (10)

1-[7-(4-hydroxy-3-methoxyphenyl)quinoxalin-2-yl]-3-thiophen-2-ylurea (11)

1-cyclohexyl-3-[7-(4-hydroxy-3,5-dimethylphenyl)quinoxalin-2-yl]urea (12)

1-cyclopentyl-3-[7-(4-hydroxy-3,5-dimethylphenyl)quinoxalin-2-yl]urea (13)

1-[7-(4-hydroxy-3,5-dimethylphenyl)quinoxalin-2-yl]-3-phenylurea (14)

1-[7-(4-hydroxy-3,5-dimethylphenyl)quinoxalin-2-yl]-3-thiophen-2-ylurea (15)

1-[7-(4-hydroxy-3,5-dimethylphenyl)quinoxalin-2-yl]-3-methylurea (16)

1-[7-(4-hydroxy-3,5-dimethylphenyl)quinoxalin-2-yl]-3-isopropylurea (17)
1-butyl-3-[7-(4-hydroxy-3,5-dimethylphenyl)quinoxalin-2-yl]urea (18)
1-ethyl-3-[7-(4-hydroxy-3,5-dimethylphenyl)quinoxalin-2-yl]urea (19)
1-cyclohexyl-3-[7-(4-hydroxy-3,5-dimethylphenyl)quinoxalin-2-yl]thiourea (20)
1-cyclohexyl-3-[7-(3,5-dichloro-4-hydroxyphenyl)quinoxalin-2-yl]thiourea (21)
1-ethyl-3-[7-(4-hydroxy-3,5-dimethylphenyl)quinoxalin-2-yl]thiourea (22)
1-cyclopropyl-3-[7-(4-hydroxy-3,5-dimethylphenyl)quinoxalin-2-yl]thiourea (23)
1-cyclopentyl-3-[7-(4-hydroxy-3,5-dimethylphenyl)quinoxalin-2-yl]thiourea (24)
1-tert-butyl-3-[7-(4-hydroxy-3,5-dimethylphenyl)quinoxalin-2-yl]thiourea (25)
1-dodecyl-3-(7-phenylquinoxalin-2-yl)urea (26)
1-(3-chloro-2-methylphenyl)-3-(7-phenylquinoxalin-2-yl)urea (27)
1-(3,4-dimethylphenyl)-3-(7-phenylquinoxalin-2-yl)urea (28)
1-allyl-3-(7-phenylquinoxalin-2-yl)urea (29)
1-cyclopentyl-3-(7-phenylquinoxalin-2-yl)urea (30)
1-[7-(4-hydroxy-3,5-dimethylphenyl)quinoxalin-2-yl]-3-isopropylthiourea (31)
1-butyl-3-[7-(4-hydroxy-3,5-dimethylphenyl)quinoxalin-2-yl]thiourea (32)
1-[7-(4-hydroxy-3,5-dimethylphenyl)quinoxalin-2-yl]-3-pentylurea (33)
1-cyclobutyl-3-[7-(4-hydroxy-3,5-dimethylphenyl)quinoxalin-2-yl]thiourea (34)
1-hexyl-3-[7-(4-hydroxy-3,5-dimethylphenyl)quinoxalin-2-yl]urea (35)
1-[7-(4-hydroxy-3,5-dimethylphenyl)quinoxalin-2-yl]-3-propylurea (36)
1-dodecyl-3-[7-(4-hydroxy-3,5-dimethylphenyl)quinoxalin-2-yl]urea (37)
1-(3-chloro-2-methylphenyl)-3-[7-(4-hydroxy-3,5-dimethylphenyl)quinoxalin-2-yl]urea (38)
1-(3-acetylphenyl)-3-[7-(4-hydroxy-3,5-dimethylphenyl)quinoxalin-2-yl]urea (39)
1-(3,4-dimethylphenyl)-3-[7-(4-hydroxy-3,5-dimethylphenyl)quinoxalin-2-yl]urea (40)
1-allyl-3-[7-(4-hydroxy-3,5-dimethylphenyl)quinoxalin-2-yl]urea (41)
1-cyclooctyl-3-[7-(4-hydroxy-3,5-dimethylphenyl)quinoxalin-2-yl]urea (42)
1-(2,4-dimethylphenyl)-3-[7-(4-hydroxy-3,5-dimethylphenyl)quinoxalin-2-yl]urea (43)
1-cyclooctyl-3-[7-(4-hydroxy-3-methoxyphenyl)quinoxalin-2-yl]urea (44)
1-adamantan-1-yl-3-(7-phenylquinoxalin-2-yl)urea (45)
1-[7-(4-hydroxy-3,5-dimethylphenyl)quinoxalin-2-yl]-3-p-tolylurea (46)
1-(3,4-dichlorophenyl)-3-[7-(4-hydroxy-3,5-dimethylphenyl)quinoxalin-2-yl]urea (47)
1-[7-(4-hydroxy-3,5-dimethylphenyl)quinoxalin-2-yl]-3-(4-methoxyphenyl)urea (48)
1-adamantan-1-yl-3-[7-(4-hydroxy-3,5-dimethylphenyl)quinoxalin-2-yl]urea (49)
1-[7-(4-hydroxy-3,5-dimethylphenyl)quinoxalin-2-yl]-3-naphthalen-2-ylurea (50)
1-[7-(4-hydroxy-3,5-dimethylphenyl)quinoxalin-2-yl]-3-(1,1,3,3-tetramethylbutyl)urea (51)
1-[7-(4-hydroxy-3,5-dimethylphenyl)quinoxalin-2-yl]-3-pyridin-3-ylurea (52)
1-((R)-1,2-dimethylpropyl)-3-[7-(4-hydroxy-3,5-dimethylphenyl)quinoxalin-2-yl]urea (53)
1-((S)-1,2-dimethylpropyl)-3-[7-(4-hydroxy-3,5-dimethylphenyl)quinoxalin-2-yl]urea (54)
1-(5-chloro-2-methylphenyl)-3-[7-(4-hydroxy-3,5-dimethylphenyl)quinoxalin-2-yl]urea (55)
1-((S)-2-phenylcyclopropyl)-3-(7-phenylquinoxalin-2-yl)urea (56)
1-[7-(4-hydroxy-3,5-dimethylphenyl)quinoxalin-2-yl]-3-((S)-2-phenylcyclopropyl)urea (57)
1-(2-chloro-6-methylphenyl)-3-[7-(4-hydroxy-3,5-dimethylphenyl)quinoxalin-2-yl]urea (58)
1-allyl-3-[7-(4-hydroxy-3-methoxyphenyl)quinoxalin-2-yl]urea (D-118068) (59)
1-(3,5-dimethylisoxazol-4-yl)-3-[7-(4-hydroxy-3,5-dimethylphenyl)quinoxalin-2-yl]urea (60)
1-sec-butyl-3-[7-(4-hydroxy-3,5-dimethylphenyl)quinoxalin-2-yl]urea (61)
1-ethyl-3-[7-(4-methoxy-3,5-dimethylphenyl)quinoxalin-2-yl]urea (62)
1-isopropyl-3-[7-(4-methoxy-3,5-dimethylphenyl)quinoxalin-2-yl]urea (63)
1-isopropyl-3-[7-(4-methoxy-3,5-dimethylphenyl)quinoxalin-2-yl]thiourea (64)
1-[7-(4-hydroxy-3,5-dimethylphenyl)quinoxalin-2-yl]-3-isobutylurea (65)
1-(1-ethylpropyl)-3-[7-(4-hydroxy-3,5-dimethylphenyl)quinoxalin-2-yl]urea (66)
1-(2,2-Dimethyl-propyl)-3-[7-(4-hydroxy-3,5-dimethyl-phenyl)-quinoxalin-2-yl]urea (67)
1-[7-(4-Amino-phenyl)-quinoxalin-2-yl]-3-isopropyl-urea (68)
1-[7-(4-Hydroxy-phenyl)-quinoxalin-2-yl]-3-isopropyl-urea (69)
1-Isopropyl-3-[7-(1-methyl-1H-pyrazol-4-yl)-quinoxalin-2-yl]-urea (70)
1-[7-(3,5-Dichloro-4-hydroxy-phenyl)-quinoxalin-2-yl]-3-pentyl-urea (71)
1-Butyl-3-[7-(3,5-dichloro-4-hydroxy-phenyl)-quinoxalin-2-yl]-urea (72)
1-[7-(3,5-Dichloro-4-hydroxy-phenyl)-quinoxalin-2-yl]-3-propyl-urea (73)
1-[7-(3,5-Dichloro-4-hydroxy-phenyl)-quinoxalin-2-yl]-3-ethyl-urea (74)
1-[7-(3,5-Dichloro-4-hydroxy-phenyl)-quinoxalin-2-yl]-3-heptyl-urea (75)
1-[7-(3,5-Dichloro-4-hydroxy-phenyl)-quinoxalin-2-yl]-3-isopropyl-urea (76)
1-tert-Butyl-3-[7-(3,5-dichloro-4-hydroxy-phenyl)-quinoxalin-2-yl]-urea (77)
1-Cycloheptyl-3-[7-(3,5-dichloro-4-hydroxy-phenyl)-quinoxalin-2-yl]-urea (78)
1-Cyclooctyl-3-[7-(3,5-dichloro-4-hydroxy-phenyl)-quinoxalin-2-yl]-urea (79)
1-Cyclobutyl-3-[7-(3,5-dichloro-4-hydroxy-phenyl)-quinoxalin-2-yl]-thiourea (80)
1-Cyclopentyl-3-[7-(3,5-dichloro-4-hydroxy-phenyl)-quinoxalin-2-yl]-urea (81)
1-[7-(3-Chloro-4-hydroxy-5-methoxy-phenyl)-quinoxalin-2-yl]-3-isopropyl-urea (82)
1-Cyclopropyl-3-[7-(3,5-dichloro-4-hydroxy-phenyl)-quinoxalin-2-yl]-thiourea (83)
1-[7-(3,5-Dichloro-4-hydroxy-phenyl)-quinoxalin-2-yl]-3-(3-phenyl-propyl)-urea (84)

1-[7-(3,5-Dichloro-4-hydroxy-phenyl)-quinoxalin-2-yl]-3-phenethyl-urea (85)
1-[7-(3,5-Dichloro-4-hydroxy-phenyl)-quinoxalin-2-yl]-3-phenyl-urea (86)
1-Butyl-3-[7-(3,5-dichloro-4-hydroxy-phenyl)-quinoxalin-2-yl]-thiourea (87)
1-[7-(3,5-Dichloro-4-hydroxy-phenyl)-quinoxalin-2-yl]-3-ethyl-thiourea (88)
1-[7-(3,5-Dichloro-4-hydroxy-phenyl)-quinoxalin-2-yl]-3-propyl-thiourea (89)
1-[7-(3,5-Dichloro-4-hydroxy-phenyl)-quinoxalin-2-yl]-3-pentyl-thiourea (90)
1-[7-(3,5-Dichloro-4-hydroxy-phenyl)-quinoxalin-2-yl]-3-isopropyl-thiourea (91)
1-Cycloheptyl-3-[7-(3,5-dichloro-4-hydroxy-phenyl)-quinoxalin-2-yl]-thiourea (92)
1-Cyclooctyl-3-[7-(3,5-dichloro-4-hydroxy-phenyl)-quinoxalin-2-yl]-thiourea (93)
1-Benzyl-3-[7-(3,5-dichloro-4-hydroxy-phenyl)-quinoxalin-2-yl]-thiourea (94)
1-[7-(3-Chloro-4-hydroxy-phenyl)-quinoxalin-2-yl]-3-isopropyl-urea (95)
1-[7-(3,5-Dichloro-4-hydroxy-phenyl)-quinoxalin-2-yl]-3-(3-phenyl-propyl)-thiourea (96)
1-[7-(3,5-Dichloro-4-hydroxy-phenyl)-quinoxalin-2-yl]-3-phenethyl-thiourea (97)
1-[2-(4-Chloro-phenyl)-ethyl]-3-[7-(3,5-dichloro-4-hydroxy-phenyl)-quinoxalin-2-yl]-thiourea (98)
1-[7-(3,5-Dichloro-4-hydroxy-phenyl)-quinoxalin-2-yl]-3-(3-morpholin-4-yl-propyl)-thiourea (99)
1-[7-(3,5-Dichloro-4-hydroxy-phenyl)-quinoxalin-2-yl]-3-[2-(3,4-dimethoxy-phenyl)-ethyl]-thiourea (100)
1-(2-Cyclohex-1-enyl-ethyl)-3-[7-(3,5-dichloro-4-hydroxy-phenyl)-quinoxalin-2-yl]-thiourea (101)
1-[7-(3,5-Dichloro-4-hydroxy-phenyl)-quinoxalin-2-yl]-3-(2-thiophen-2-yl-ethyl)-urea (102)
1-[7-(3,5-Dichloro-4-hydroxy-phenyl)-quinoxalin-2-yl]-3-[2-(4-methoxy-phenyl)-ethyl]-thiourea (103)
1-[7-(3,5-Dichloro-4-hydroxy-phenyl)-quinoxalin-2-yl]-3-[2-(4-ethyl-phenyl)-ethyl]-urea (104)
1-[7-(3,5-Dichloro-4-hydroxy-phenyl)-quinoxalin-2-yl]-3-[2-(3,5-dimethoxy-phenyl)-ethyl]-urea (105)
1-[7-(3,5-Dichloro-4-hydroxy-phenyl)-quinoxalin-2-yl]-3-[2-(3,4-dichloro-phenyl)-ethyl]-urea (106)
1-[2-(3-Bromo-4-methoxy-phenyl)-ethyl]-3-[7-(3,5-dichloro-4-hydroxy-phenyl)-quinoxalin-2-yl]-urea (107)
1-(2-Biphenyl-4-yl-ethyl)-3-[7-(3,5-dichloro-4-hydroxy-phenyl)-quinoxalin-2-yl]-urea (108)
1-[7-(3,5-Dichloro-4-hydroxy-phenyl)-quinoxalin-2-yl]-3-[2-(2,3-dimethoxy-phenyl)-ethyl]-urea (109)
1-[7-(3,5-Dichloro-4-hydroxy-phenyl)-quinoxalin-2-yl]-3-[2-(2-fluoro-phenyl)-ethyl]-urea (110)
1-[7-(3,5-Dichloro-4-hydroxy-phenyl)-quinoxalin-2-yl]-3-[2-(2,4-dichloro-phenyl)-ethyl]-urea (111)
1-[7-(3,5-Dichloro-4-hydroxy-phenyl)-quinoxalin-2-yl]-3-[2-(4-fluoro-phenyl)-ethyl]-urea (112)
1-[7-(3,5-Dichloro-4-hydroxy-phenyl)-quinoxalin-2-yl]-3-[2-(3,4-dimethoxy-phenyl)-ethyl]-urea (113)
1-[7-(3,5-Dichloro-4-hydroxy-phenyl)-quinoxalin-2-yl]-3-[2-(4-methoxy-phenyl)-ethyl]-urea (114)
1-[7-(3,5-Dichloro-4-hydroxy-phenyl)-quinoxalin-2-yl]-3-[2-(2,5-dimethoxy-phenyl)-ethyl]-urea (115)
1-[2-(4-Chloro-phenyl)-ethyl]-3-[7-(3,5-dichloro-4-hydroxy-phenyl)-quinoxalin-2-yl]-urea (116)
1-[2-(3-Chloro-phenyl)-ethyl]-3-[7-(3,5-dichloro-4-hydroxy-phenyl)-quinoxalin-2-yl]-urea (117)
1-(2-Cyclopentyl-ethyl)-3-[7-(3,5-dichloro-4-hydroxy-phenyl)-quinoxalin-2-yl]-thiourea (118)
1-(2-Cyclohexyl-ethyl)-3-[7-(3,5-dichloro-4-hydroxy-phenyl)-quinoxalin-2-yl]-urea (119)
1-(2-Cyclohexyl-ethyl)-3-[7-(3,5-dichloro-4-hydroxy-phenyl)-quinoxalin-2-yl]-thiourea (120)
1-[7-(3,5-Dichloro-4-hydroxy-phenyl)-quinoxalin-2-yl]-3-[2-(4-hydroxy-phenyl)-ethyl]-thiourea (121)
1-[7-(3,5-Dichloro-4-hydroxy-phenyl)-quinoxalin-2-yl]-3-(2-pyridin-3-yl-ethyl)-thiourea (122)

These compounds can be present as the free base or else as salts of physiologically acceptable acids.

Chemical Synthesis

The compounds of the general formula I can be obtained according to Scheme 1 below:

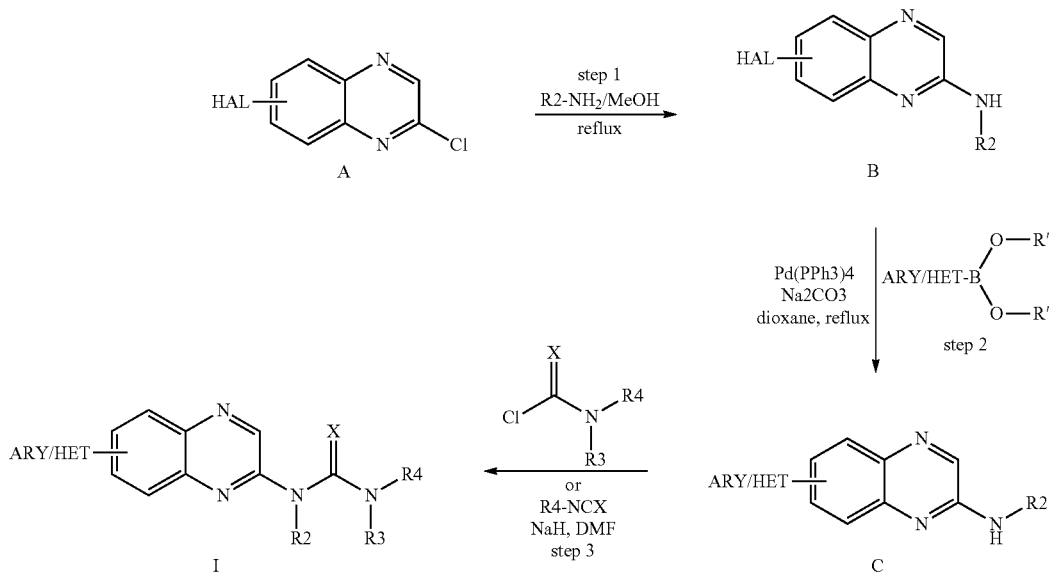

Scheme 1

The starting materials are either commercially available or can be prepared by procedures known per se. The starting materials B and C are useful intermediates for preparing the quinoxalines of the general formula I according to the invention.

For the preparation of the starting materials and target compounds, reference may be made, for example, to the following primary literature, the content of which is hereby incorporated into the disclosure of the present application:
1) W. C. Lumma et al. *J. Med. Chem.* 1991, 24, 93-101;
2) J. P. Horwitz et al. *J. Med. Chem.* 2001, 44, 1758-1776.

Any solvents and auxiliaries to be used, if appropriate, and the reaction parameters to be used, such as temperature and duration of the reaction, are known to the person skilled in the art by virtue of his expert knowledge.

The compounds below, which are evident from the statement of the respective chemical name from the survey hereinafter, were synthesized in accordance with this general procedure for steps 1, 2 and 3 based on Synthesis Scheme 1. The analytical characterization of the compounds according to the invention was carried out by their melting points and/or by $^1$H-NMR spectroscopy and/or mass spectroscopy.

The chemicals and solvents used were obtained commercially from conventional suppliers (Acros, Avocado, Aldrich, Fluka, Lancaster, Maybridge, Merck, Sigma, TCI etc.) or synthesized.

EXAMPLES

The invention is to be explained in more detail by means of the following examples without being restricted thereto.

The chemical names of the substances were generated using the AutoNom 2000 Software (ISIS™/Draw 2.5 SP2; MDL).

Example 1

Reaction According to Scheme 1, Step 1

Example 1.1

7-Chloroquinoxalin-2-ylamine

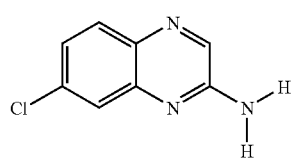 [SMILES: Nc1cnc2ccc(Cl)cc2n1]

At T=120° C., 30.0 g (60.0 mmol) of 2,7-dichloroquinoxaline are stirred in 400 ml of NH$_3$/MeOH (w=22%) for 16 hours. The mixture is then evaporated to dryness under reduced pressure, and the residue is taken up in 250 ml of dichloromethane and 250 ml of water. After phase separation, the organic phase is then washed with 250 ml of water and dried over sodium sulphate, and the solvent is removed under membrane pump vacuum. The residue obtained is purified by column chromatography on silica gel (ethyl acetate/petroleum ether=1:5; silica gel: 200-300 mesh), which gives 10.5 g of 7-chloroquinoxalin-2-ylamine (yield 98%).

m.p.: 219-222° C.
$^1$H-NMR (300 MHz, CDCl$_3$) δ=8.30 (1H, s), 7.83 (1H, s), 7.65 (1H, m), 7.40 (1H, m) ppm
MS (ESI) m/z 180 (MH$^+$)

Example 2

Reaction According to Scheme 1, Step 2

Example 2.1

4-(3-Aminoquinoxalin-6-yl)-2,6-dimethylphenol

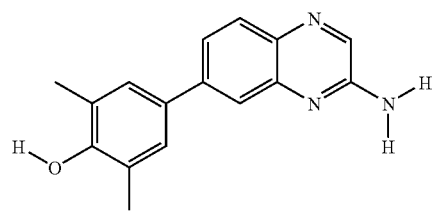 [SMILES: Cc1cc(-c2ccc3ncc(N)nc3c2)cc(C)c1O]

Under argon, 1.66 g (6.7 mmol) of 3,5-dimethyl-4-hydroxyphenylboronic acid pinacol ester, 1.42 g (13.4 mmol) of sodium carbonate dissolved in 10 ml of water and 0.155 g (0.13 mmol) of Pd(PPh$_3$)$_4$ are added to a solution of 0.8 g (4.5 mmol) of 7-chloroquinoxalin-2-ylamine in 40 ml of dioxane, and the mixture is stirred at 100° C. for 4 hours.

For work-up, 30 ml of ethyl acetate and 30 ml of water are added to the reaction mixture, the phases are separated, the organic phase is dried over magnesium sulphate and filtered and the solvent is removed on a rotary evaporator. The residue obtained is purified by column chromatography on silica gel (ethyl acetate/n-heptane), which gives 0.65 g of 4-(3-aminoquinoxalin-6-yl)-2,6-dimethylphenol.

Yield: 33.1%
m.p.: 256° C.
$^1$H-NMR (600 MHz, DMSO-d$_6$) δ=8.43 (1H, br. s), 8.24 (1H, s), 7.75 (1H, d), 7.62 (1H, m), 7.57 (1H, m), 7.35 (2H, s), 6.90 (2H, s), 2.25 (6H, s) ppm
MS (ESI) m/z 266 (MH$^+$)

The intermediates below of the formula B were synthesized analogously to Example 2.1 (4-(3-aminoquinoxalin-6-yl)-2,6-dimethylphenol).

Ex. 2.2

7-Phenylquinoxalin-2-amine

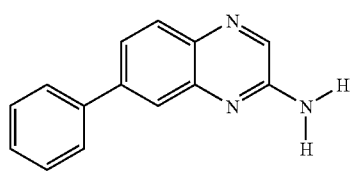 [SMILES: Nc1cnc2ccc(-c3ccccc3)cc2n1]

$^1$H-NMR (300 MHz, DMSO-d$_6$) δ=8.93 (1H, m), 8.81 (1H, s), 8.00 (5H, m), 7.45 (3H, s) ppm
MS (ESI) m/z 222 (MH$^+$)

Ex. 2.3

4-(3-Aminoquinoxalin-6-yl)-2-methoxyphenol

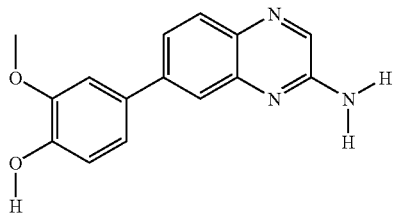 [SMILES: COc1cc(-c2ccc3ncc(N)nc3c2)ccc1O]

$^1$H-NMR (300 MHz, DMSO-$d_6$) δ=8.26 (1H, s), 7.70 (4H, s), 7.30 (2H, J=5.4 Hz, m), 6.90 (1H, m), 4.00 (3H, s) ppm
MS (ESI) 269 (MH$^+$)

Ex. 2.4

7-(3,4-Dimethoxyphenyl)quinoxalin-2-amine

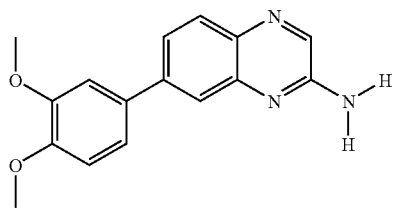 [SMILES: COc1ccc(-c2ccc3ncc(N)nc3c2)cc1OC]

$^1$H-NMR (300 MHz, DMSO-$d_6$) δ=8.26 (1H, s), 7.50 (4H, s), 7.30 (1H, J=5.4 Hz, m), 6.90 (2H, m), 3.88 (6H, s) ppm;
MS (ESI) 282 (MH$^+$)

Ex. 2.5

4-(3-Aminoquinoxalin-6-yl)-2,6-dichlorophenol

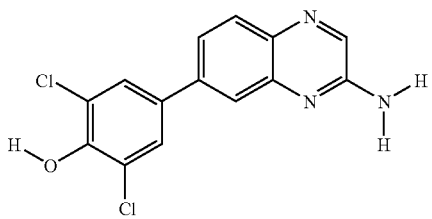 [SMILES: Nc1cnc2ccc(-c3cc(Cl)c(O)c(Cl)c3)cc2n1]

m.p.: 263° C.

$^1$H-NMR (600 MHz, DMSO-$d_6$) δ=10.35 (1H, s), 8.28 (1H, s), 7.78 (3H, m), 7.71 (1H, m), 7.63 (1H, m), 7.02 (2H, s) ppm
MS (ESI) m/z 306 (MH$^+$)

Ex. 2.6

7-(4-Methoxy-3,5-dimethylphenyl)quinoxalin-2-ylamine

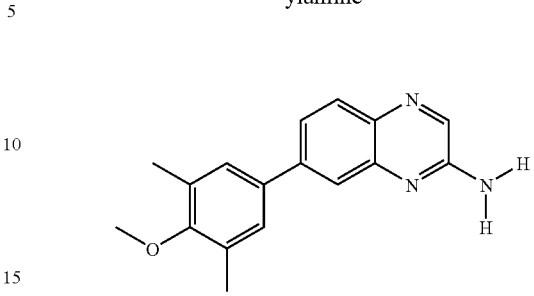

$^1$H-NMR (600 MHz, DMSO-$d_6$) δ=8.26 (1H, s), 7.78 (1H, d), 7.67 (1H, m), 7.58 (1H, m), 7.43 (2H, s), 6.95 (2H, s), 3.75 (3H, s) ppm
MS (ESI) m/z 280 (MH$^+$)

Example 3

Reaction According to Scheme 1, Step 3

General Procedure (GP) for Preparing the Urea or Thiourea Derivatives:

With ice-cooling, 0.45 mmol of intermediate B (see Example 2) is added to a mixture of 0.71 mmol of sodium hydride (60% strength suspension in mineral oil) in 5 ml of dimethylformamide or THF. After 30 min of stirring at 0° C., 0.54 mmol of the appropriate isocyanate or isothiocyanate dissolved in 2 ml of THF is added dropwise, and ice-cooling is removed. After 16 h of stirring at room temperature, the reaction solution is, under membrane pump vacuum, concentrated to dryness, and the residue is taken up in 50 ml of water and 50 ml of ethyl acetate, resulting in the precipitation of the product. The precipitate is filtered off with suction and then dried in a vacuum drying cabinet, which gives the target compound.

The following compounds of the formula I were synthesized analogously to the synthesis route in Scheme 1 and in accordance with the general procedure:

Example 3.1

1-Cyclopentyl-3-[7-(4-hydroxy-3-methoxyphenyl)quinoxalin-2-yl]urea (1)

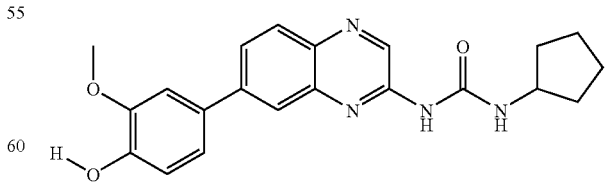

$^1$H-NMR (300 MHz, DMSO-$d_6$) δ=9.99 (1H, s), 8.80 (1H, m), 8.75 (1H, s), 7.95 (3H, s), 7.25 (2H, s), 6.90 (1H, m), 4.01 (1H, m), 3.90 (3H, s), 1.90 (3H, s), 1.6 (5H, s) ppm
MS (ESI) m/z 379 (MH$^+$)

Example 3.2

1-Cyclohexyl-3-[7-(4-hydroxy-3-methoxyphenyl)quinoxalin-2-yl]urea (2)

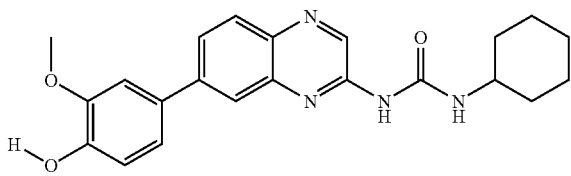 [SMILES: COc1cc(-c2ccc3ncc(NC(=O)NC4CCCCC4)nc3c2)ccc1O]

$^1$H-NMR (300 MHz, DMSO-$d_6$) δ=9.99 (1H, s), 8.80 (1H, m), 8.75 (1H, s), 7.95 (3H, s), 7.25 (2H, s), 6.90 (1H, m), 3.90 (3H, m), 3.68 (1H, s), 1.7 (4H, s), 1.4 (6H, s) ppm MS (ESI) m/z 392 (MH$^+$)

Example 3.3

1-Cyclohexyl-3-[7-(3,4-dimethoxyphenyl)quinoxalin-2-yl]urea (3)

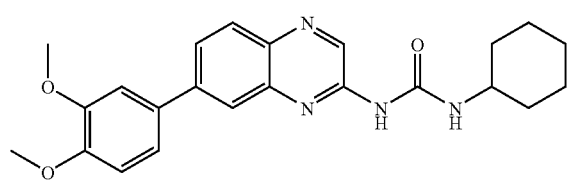 [SMILES: COc1ccc(-c2ccc3ncc(NC(=O)NC4CCCCC4)nc3c2)cc1OC]

$^1$H-NMR (300 MHz, DMSO-$d_6$) δ=9.86 (1H, m), 8.88 (1H, s), 8.77 (1H, s), 7.95 (3H, s), 7.38 (2H, s), 7.11 (1H, m), 3.90 (3H, s) 3.80 (3H, s), 3.36 (1H, s), 1.75 (2H, s), 1.52 (6H, m) ppm MS (ESI) m/z 407 (MH$^+$)

Example 3.4

1-[7-(3,4-Dimethoxyphenyl)quinoxalin-2-yl]-3-[1-(2,2,2-trifluoroacetyl)-piperidin-4-yl]urea (4)

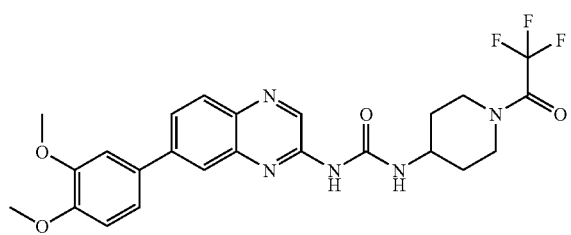 [SMILES: COc1ccc(-c2ccc3ncc(NC(=O)NC4CCN(C(=O)C(F)(F)F)CC4)nc3c2)cc1OC]

$^1$H-NMR (300 MHz, DMSO-$d_6$) δ=10.13 (1H, s), 8.89 (1H, m), 8.82 (1H, s), 8.07 (1H, m), 7.96 (2H, s), 7.35 (2H, s), 7.00 (1H, s), 4.22 (2H, m), 4.15 (1H, m), 3.90 (3H, s), 3.82 (3H, s), 3.49 (1H, s), 3.25 (1H, s), 2.04 (2H, m), 1.65 (2H, m) ppm MS (ESI) m/z 504 (MH$^+$)

Example 3.5

1-[7-(4-Hydroxy-3-methoxyphenyl)quinoxalin-2-yl]-3-phenylurea (5)

$^1$H-NMR (300 MHz, DMSO-$d_6$) δ=10.98 (1H, s), 10.40 (1H, s), 9.30 (1H, m), 8.88 (1H, s), 8.20 (3H, m), 7.68 (2H, s), 7.52 (4H, s), 6.90 (2H, m), 3.90 (3H, s) ppm MS (ESI) m/z 386 (MH$^+$)

Example 3.6

1-[7-(4-Hydroxy-3-methoxyphenyl)quinoxalin-2-yl]-3-[1-(2,2,2-trifluoroacetyl)piperidin-4-yl]urea (6)

$^1$H-NMR (300 MHz, DMSO-$d_6$) δ=10.12 (1H, s), 9.30 (1H, m), 8.88 (1H, s), 8.80 (1H, m), 8.78 (3H, s), 7.35 (2H, s), 6.90 (1H, m), 4.15 (2H, m), 3.90 (3H, s), 3.33 (2H, m), 2.15 (2H, m), 1.75 (2H, m) ppm MS (ESI) m/z 489 (MH$^+$)

Example 3.7

1-Benzyl-3-[7-(4-hydroxy-3-methoxyphenyl)quinoxalin-2-yl]urea (7)

$^1$H-NMR (300 MHz, DMSO-$d_6$) δ=10.50 (1H, s), 9.30 (1H, m), 8.88 (1H, s), 8.00 (3H, s), 7.41 (5H, s), 7.25 (2H, m), 6.90 (1H, m), 4.53 (2H, m), 3.90 (3H, s) ppm MS (ESI) m/z 400 (MH$^+$)

Example 3.8

1-Cyclopentyl-3-[7-(3,4-dimethoxyphenyl)quinoxalin-2-yl]urea (8)

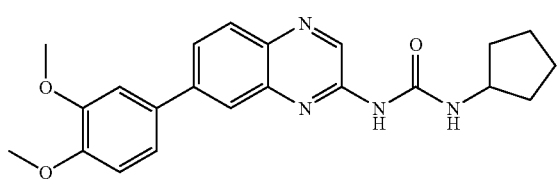 [SMILES: COc1ccc(-c2ccc3ncc(NC(=O)NC4CCCC4)nc3c2)cc1OC]

$^1$H-NMR (300 MHz, DMSO-d$_6$) δ=9.86 (1H, m), 8.88 (1H, s), 8.77 (1H, s), 7.95 (3H, s), 7.38 (2H, s), 7.11 (1H, m), 4.12 (1H, s), 3.90 (3H, s) 3.80 (3H, s), 1.75 (2H, s), 1.52 (6H, m) ppm MS (ESI) m/z 393 (MH$^+$)

Example 3.9

1-tert-Butyl-3-[7-(4-hydroxy-3,5-dimethylphenyl)quinoxalin-2-yl]urea (9)

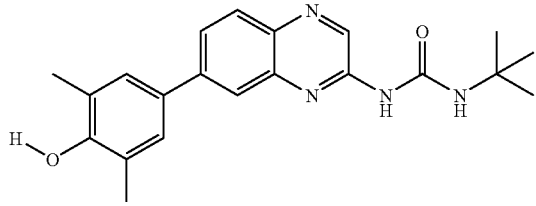

$^1$H-NMR (300 MHz, DMSO-d$_6$) δ=9.84 (1H, s), 9.88 (1H, s), 8.76 (1H, m), 8.58 (1H, s), 7.89 (3H, s), 7.45 (2H, s), 2.28 (6H, s), 1.40 (9H, m) ppm MS (ESI) m/z 365 (MH$^+$)

Example 3.10

1-tert-Butyl-3-[7-(4-hydroxy-3-methoxyphenyl)quinoxalin-2-yl]urea (10)

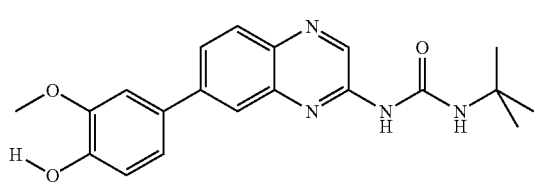 [SMILES: COc1cc(-c2ccc3ncc(NC(=O)NC(C)(C)C)nc3c2)ccc1O]

$^1$H-NMR (300 MHz, DMSO-d$_6$) δ=10.50 (1H, s), 9.30 (1H, m), 8.88 (1H, s), 8.20 (1H, m), 8.81 (1H, s), 7.91 (3H, s), 7.32 (2H, s), 6.90 (1H, m), 3.90 (3H, s), 1.42 (9H, m) ppm MS (ESI) m/z 367 (MH$^+$)

Example 3.11

1-[7-(4-Hydroxy-3-methoxyphenyl)quinoxalin-2-yl]-3-thiophen-2-ylurea (11)

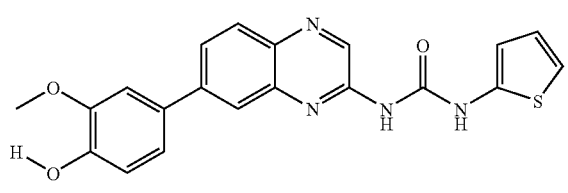 [SMILES: COc1cc(-c2ccc3ncc(NC(=O)Nc4cccs4)nc3c2)ccc1O]

$^1$H-NMR (300 MHz, DMSO-d$_6$) δ=10.50 (1H, s), 9.30 (1H, m), 8.88 (1H, s), 8.20 (1H, m), 8.00 (2H, s), 7.35 (2H, s), 7.00 (2H, s), 6.90 (2H, m), 3.90 (3H, s) ppm MS (ESI) m/z 393 (MH$^+$)

Example 3.12

1-Cyclohexyl-3-[7-(4-hydroxy-3,5-dimethylphenyl)quinoxalin-2-yl]urea (12)

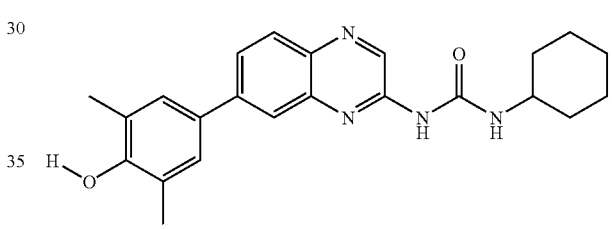

$^1$H-NMR (300 MHz, DMSO-d$_6$) δ=9.98 (1H, s), 8.86 (1H, m), 8.58 (1H, s), 7.98 (1H, m), 7.89 (2H, s), 7.45 (2H, s), 3.34 (1H, s), 2.28 (6H, s), 1.88 (2H, s), 1.70 (3H, m), 1.35 (5H, m) ppm MS (ESI) m/z 391 (MH$^+$)

Example 3.13

1-Cyclopentyl-3-[7-(4-hydroxy-3,5-dimethylphenyl)quinoxalin-2-yl]urea (13)

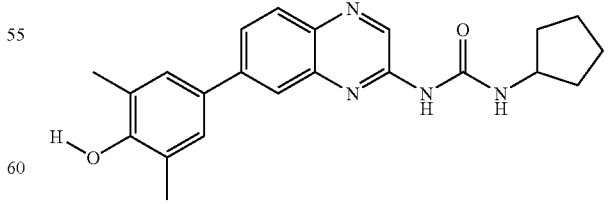

$^1$H-NMR (300 MHz, DMSO-d$_6$) δ=9.98 (1H, s), 8.86 (1H, m), 8.58 (1H, s), 7.98 (1H, m), 7.89 (2H, s), 7.45 (2H, s), 4.11 (1H, s), 2.28 (6H, s), 1.96 (2H, s), 1.70 (6H, s) ppm MS (ESI) m/z 377 (MH$^+$)

Example 3.14

1-[7-(4-Hydroxy-3,5-dimethylphenyl)quinoxalin-2-yl]-3-phenylurea (14)

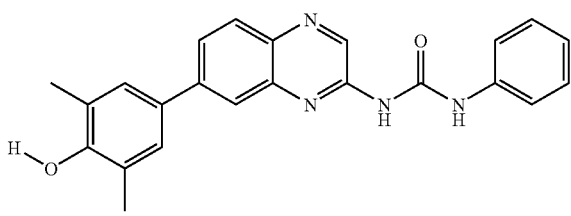 [SMILES: Cc1cc(-c2ccc3ncc(NC(=O)Nc4ccccc4)nc3c2)cc(C)c1O]

$^1$H-NMR (300 MHz, DMSO-$d_6$) δ=10.98 (1H, s), 8.88 (1H, s), 8.00 (3H, m), 7.86 (2H, s), 7.42 (4H, s), 7.00 (1H, s), 2.25 (6H, m) ppm
MS (ESI) m/z 385 (MH$^+$)

Example 3.15

1-[7-(4-Hydroxy-3,5-dimethylphenyl)quinoxalin-2-yl]-3-thiophen-2-ylurea (15)

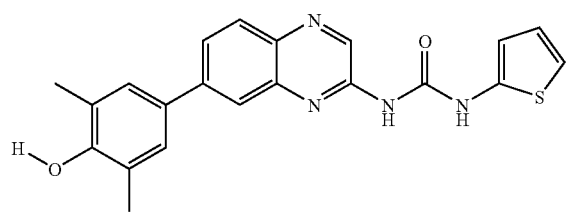 [SMILES: Cc1cc(-c2ccc3ncc(NC(=O)Nc4cccs4)nc3c2)cc(C)c1O]

$^1$H-NMR (300 MHz, DMSO-$d_6$) δ=11.85 (1H, s), 10.56 (1H, s), 9.98 (1H, s), 8.96 (1H, m), 8.58 (1H, s), 8.22 (1H, s), 7.98 (2H, m), 7.52 (2H, s), 7.00 (2H, s), 6.95 (1H, s), 2.28 (6H, s) ppm
MS (ESI) m/z 391 (MH$^+$)

Example 3.16

1-[7-(4-Hydroxy-3,5-dimethylphenyl)quinoxalin-2-yl]-3-methylurea (16)

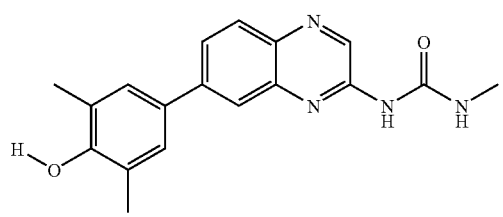 [SMILES: CNC(=O)Nc1cnc2ccc(-c3cc(C)c(O)c(C)c3)cc2n1]

m.p.: 251° C.
$^1$H-NMR (600 MHz, DMSO-$d_6$) δ=10.1 (1H, s), 8.82 (1H, m), 8.69 (1H, s), 8.52 (1H, s), 8.08 (1H, s), 7.92 (1H, m), 7.85 (1H, s), 7.44 (2H, s), 2.85 (3H, s), 2.25 (6H, s) ppm
MS (ESI) m/z 323 (MH$^+$)

Example 3.17

1-[7-(4-Hydroxy-3,5-dimethylphenyl)quinoxalin-2-yl]-3-isopropylurea (17)

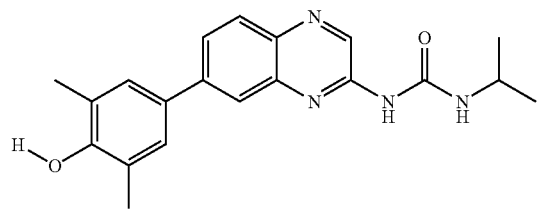 [SMILES: Cc1cc(-c2ccc3ncc(NC(=O)NC(C)C)nc3c2)cc(C)c1O]

m.p.: 280-283° C.
$^1$H-NMR (600 MHz, DMSO-$d_6$) δ=9.92 (1H, s), 8.82 (1H, s), 8.54 (1H, s), 7.95-7.85 (3H, m), 7.42 (2H, s), 3.85 (1H, m), 2.25 (6H, s), 1.22 (6H, d) ppm
MS (ESI) m/z 351 (MH$^+$)

Example 3.18

1-Butyl-3-[7-(4-hydroxy-3,5-dimethylphenyl)quinoxalin-2-yl]urea (18)

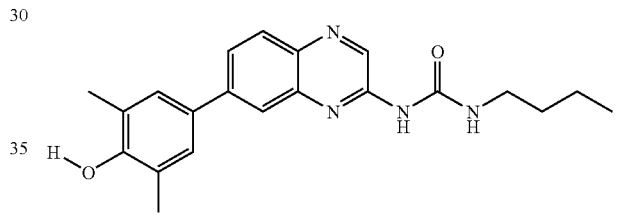

m.p.: 276-280° C.
$^1$H-NMR (600 MHz, DMSO-$d_6$) δ=10.02 (1H, s), 8.85 (1H, s), 8.73 (1H, s), 8.53 (1H, s), 7.96-7.83 (3H, m), 7.42 (2H, s), 3.28 (2H, m), 2.48 (6H, s), 1.52 (2H, m), 1.38 (2H, m), 0.95 (3H, m) ppm
MS (ESI) m/z 365 (MH$^+$)

Example 3.19

1-Ethyl-3-[7-(4-hydroxy-3,5-dimethylphenyl)quinoxalin-2-yl]urea (19)

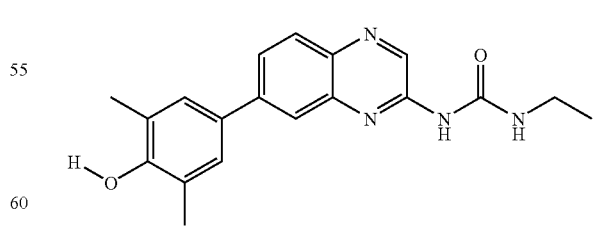

m.p.: 257° C.
$^1$H-NMR (600 MHz, DMSO-$d_6$) δ=10.0 (1H, s), 8.82 (1H, m), 8.74 (1H, s), 8.22 (1H, m), 7.94-7.84 (2H, m), 7.43 (2H, s), 3.28 (2H, m), 2.23 (6H, s), 1.18 (3H, m) ppm
MS (ESI) m/z 337 (MH$^+$)

Example 3.20

1-Cyclohexyl-3-[7-(4-hydroxy-3,5-dimethylphenyl)quinoxalin-2-yl]-thiourea (20)

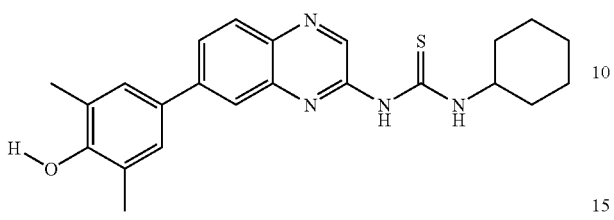

$^1$H-NMR (600 MHz, DMSO-$d_6$) δ=11.78 (1H, s), 11.16 (1H, s), 8.75 (1H, s), 8.55 (1H, m), 7.96-7.85 (3H, m), 7.41 (2H, s), 4.35 (1H, m), 3.28 (2H, m), 2.28 (6H, s), 1.95 (2H, m), 1.77 (2H, m), 1.62 (3H, m), 1.45 (3H, m) ppm
MS (ESI) m/z 407 (MH$^+$)

Example 3.21

1-Cyclohexyl-3-[7-(3,5-dichloro-4-hydroxyphenyl)quinoxalin-2-yl]-thiourea (21)

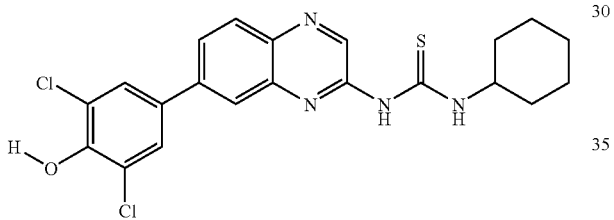

m.p.: 284° C.
$^1$H-NMR (600 MHz, DMSO-$d_6$) δ=11.64 (1H, s), 11.2 (1H, s), 10.48 (1H, s), 8.79 (1H, s), 8.03-7.96 (3H, m), 7.87 (2H, s), 4.22 (1H, m), 2.02 (2H, m), 1.85 (2H, m), 1.62 (3H, m), 1.4 (3H, m) ppm

Example 3.22

1-Ethyl-3-[7-(4-hydroxy-3,5-dimethylphenyl)quinoxalin-2-yl]thiourea (22)

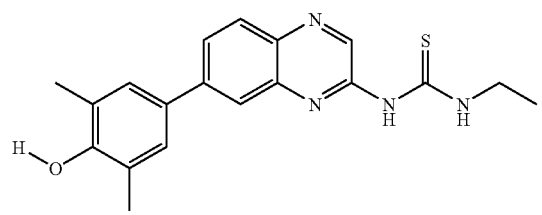

m.p.: 243-244° C.
$^1$H-NMR (600 MHz, DMSO-$d_6$) δ=11.65 (1H, s), 11.14 (1H, s), 8.74 (1H, s), 8.55 (1H, m), 8.15 (1H, m), 7.97-7.7.91 (2H, m), 7.41 (2H, s), 3.78 (2H, m), 2.24 (6H, s), 1.28 (3H, m) ppm
MS (ESI) m/z 353 (MH$^+$)

Example 3.23

1-Cyclopropyl-3-[7-(4-hydroxy-3,5-dimethylphenyl)quinoxalin-2-yl]-thiourea (23)

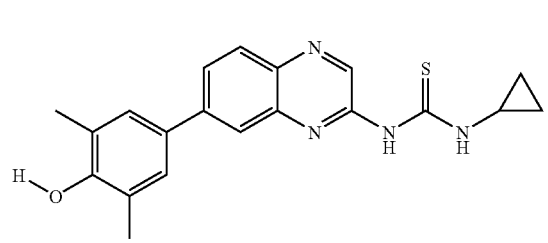 [SMILES: Cc1cc(-c2ccc3ncc(NC(=S)NC4CC4)nc3c2)cc(C)c1O]

m.p.: 274-276° C.
$^1$H-NMR (600 MHz, DMSO-$d_6$) δ=11.61 (1H, s), 11.23 (1H, s), 8.73 (1H, s), 8.53 (1H, m), 7.99-7.7.91 (3H, m), 7.46 (2H, s), 3.22 (1H, m), 0.91-0.78 (4H, m) ppm
MS (ESI) m/z 365 (MH$^+$)

Example 3.24

1-Cyclopentyl-3-[7-(4-hydroxy-3,5-dimethylphenyl)quinoxalin-2-yl]-thiourea (24)

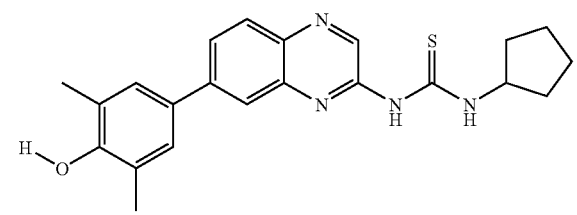

m.p.: 271-272° C.
MS (ESI) m/z 393 (MH$^+$)

Example 3.25

1-tert-Butyl-3-[7-(4-hydroxy-3,5-dimethylphenyl)quinoxalin-2-yl]thiourea (25)

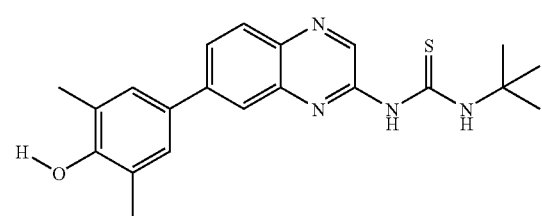

m.p.: 238-240° C.
MS (ESI) m/z 381 (MH$^+$)

Example 3.26

1-Dodecyl-3-(7-phenylquinoxalin-2-yl)urea (26)

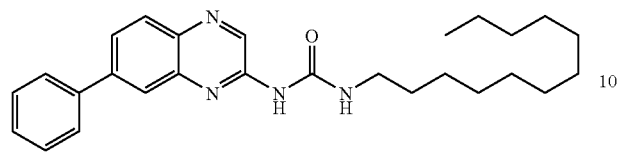

$^1$H-NMR (300 MHz, DMSO-d$_6$) δ=10.14 (1H, s), 8.93 (1H, m), 8.81 (1H, s), 8.00 (5H, m), 7.45 (3H, s), 3.31 (2H, s), 1.57 (2H, s), 1.24 (20H, m), 0.83 (3H, s) ppm MS (ESI) m/z 433 (MH$^+$)

Example 3.27

1-(3-Chloro-2-methylphenyl)-3-(7-phenylquinoxalin-2-yl)urea (27)

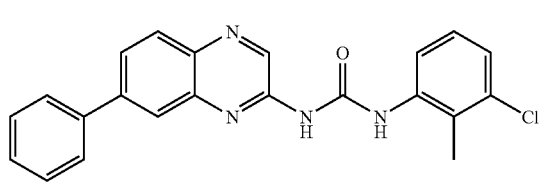 [SMILES: Cc1c(Cl)cccc1NC(=O)Nc1cnc2ccc(-c3ccccc3)cc2n1]

$^1$H-NMR (300 MHz, DMSO-d$_6$) δ=10.77 (1H, s), 10.14 (1H, s), 8.93 (1H, m), 8.00 (5H, m), 7.45 (5H, s), 7.22 (1H, s), 2.21 (3H, s) ppm MS (ESI) m/z 389 (MH$^+$)

Example 3.28

1-(3,4-Dimethylphenyl)-3-(7-phenylquinoxalin-2-yl)urea (28)

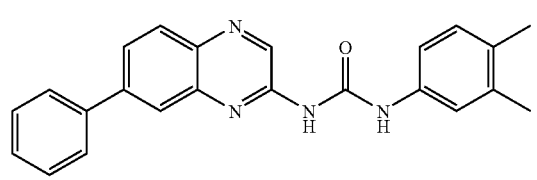 [SMILES: Cc1ccc(NC(=O)Nc2cnc3ccc(-c4ccccc4)cc3n2)cc1C]

$^1$H-NMR (300 MHz, DMSO-d$_6$) δ=10.77 (1H, s), 10.14 (1H, s), 8.93 (1H, m), 8.00 (5H, m), 7.45 (5H, s), 7.22 (1H, s), 2.21 (6H, s) ppm MS (ESI) m/z 369 (MH$^+$)

Example 3.29

1-Allyl-3-(7-phenylquinoxalin-2-yl)urea (29)

$^1$H-NMR (300 MHz, DMSO-d$_6$) δ=10.14 (1H, s), 8.88 (2H, m), 8.00 (5H, m), 7.45 (3H, s), 6.00 (1H, s), 5.21 (2H, s), 3.95 (2H, m) ppm MS (ESI) m/z 305 (MH$^+$)

Example 3.30

1-Cyclopentyl-3-(7-phenylquinoxalin-2-yl)urea (30)

$^1$H-NMR (300 MHz, DMSO-d$_6$) δ=10.14 (1H, s), 8.93 (2H, m), 8.00 (5H, m), 7.45 (3H, s), 3.61 (1H, s), 1.57 (8H, s) ppm MS (ESI) m/z 333 (MH$^+$)

Example 3.31

1-[7-(4-Hydroxy-3,5-dimethylphenyl)quinoxalin-2-yl]-3-isopropylthiourea (31)

m.p.: 269-271° C.

MS (ESI) m/z 367 (MH$^+$)

Example 3.32

1-Butyl-3-[7-(4-hydroxy-3,5-dimethylphenyl)qui-
noxalin-2-yl]thiourea (32)

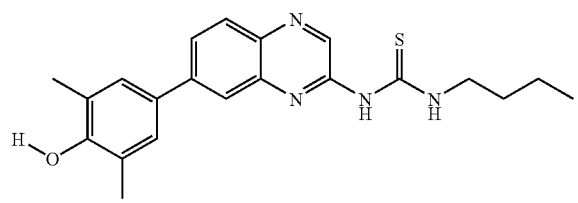

m.p.: 278-280° C.
MS (ESI) m/z 381 (MH+)

Example 3.33

1-[7-(4-Hydroxy-3,5-dimethylphenyl)quinoxalin-2-
yl]-3-pentylurea (33)

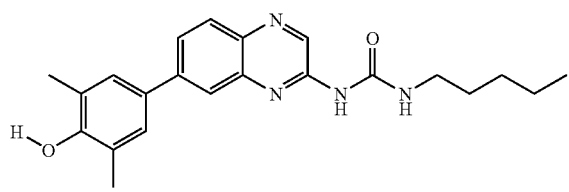 [SMILES: CCCCCNC(=O)Nc1cnc2ccc(-c3cc(C)c(O)c(C)c3)cc2n1]

m.p.: 274-275° C.
MS (ESI) m/z 379 (MH+)

Example 3.34

1-Cyclobutyl-3-[7-(4-hydroxy-3,5-dimethylphenyl)
quinoxalin-2-yl]-thiourea (34)

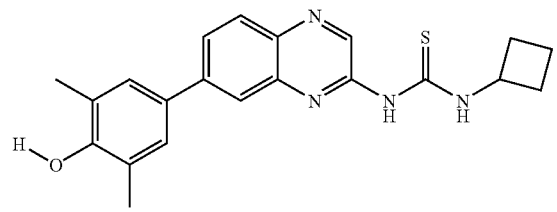 [SMILES: Cc1cc(-c2ccc3ncc(NC(=S)NC4CCC4)nc3c2)cc(C)c1O]

m.p.: 285-286° C.
MS (ESI) m/z 379 (MH+)

Example 3.35

1-Hexyl-3-[7-(4-hydroxy-3,5-dimethylphenyl)qui-
noxalin-2-yl]urea (35)

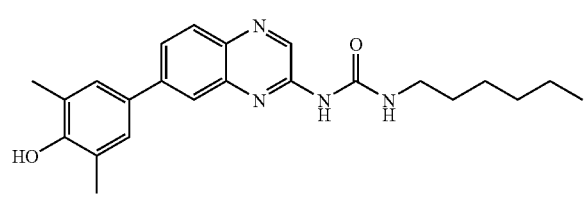 [SMILES: CCCCCCNC(=O)Nc1cnc2ccc(-c3cc(C)c(O)c(C)c3)cc2n1]

m.p.: 272-273° C.
MS (ESI) m/z 393 (MH+)

Example 3.36

1-[7-(4-Hydroxy-3,5-dimethylphenyl)quinoxalin-2-
yl]-3-propylurea (36)

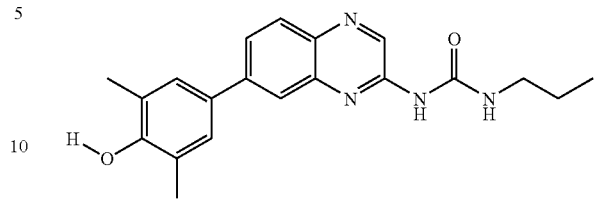

m.p.: 276-277° C.
MS (ESI) m/z 351 (MH+)

Example 3.37

1-Dodecyl-3-[7-(4-hydroxy-3,5-dimethylphenyl)
quinoxalin-2-yl]urea (37)

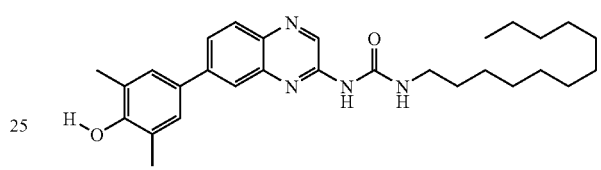

$^1$H-NMR (300 MHz, DMSO-$d_6$) δ=10.14 (1H, s), 8.93 (1H, m), 8.71 (1H, s), 8.51 (1H, s), 7.95 (3H, m), 7.45 (2H, s), 2.26 (6H, s), 1.57 (2H, s), 1.24 (20H, m) ppm
MS (ESI) m/z 477 (MH+)

Example 3.38

1-(3-Chloro-2-methylphenyl)-3-[7-(4-hydroxy-3,5-
dimethylphenyl)-quinoxalin-2-yl]urea (38)

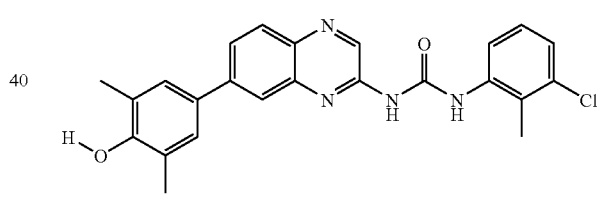

$^1$H-NMR (300 MHz, DMSO-$d_6$) δ=11.14 (1H, s), 10.14 (1H, s), 8.93 (1H, m), 8.51 (1H, s), 7.95 (4H, m), 7.45 (4H, s), 7.15 (1H, s), 2.26 (6H, s), 2.15 (3H, s) ppm
MS (ESI) m/z 433 (MH+)

Example 3.39

1-(3-Acetylphenyl)-3-[7-(4-hydroxy-3,5-dimeth-
ylphenyl)quinoxalin-2-yl]urea (39)

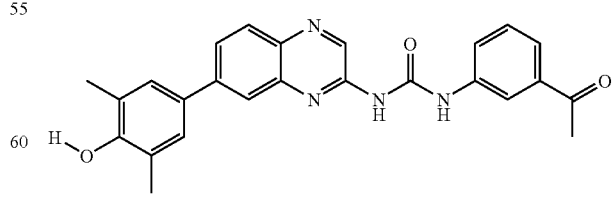

$^1$H-NMR (300 MHz, DMSO-$d_6$) δ=11.14 (1H, s), 10.14 (1H, s), 8.93 (1H, m), 8.51 (1H, s), 7.95 (4H, m), 7.45 (2H, s), 7.15 (2H, s), 2.56 (3H, s), 2.15 (3H, s) ppm
MS (ESI) m/z 427 (MH+)

Example 3.40

1-(3,4-Dimethylphenyl)-3-[7-(4-hydroxy-3,5-dimethylphenyl)quinoxalin-2-yl]urea (40)

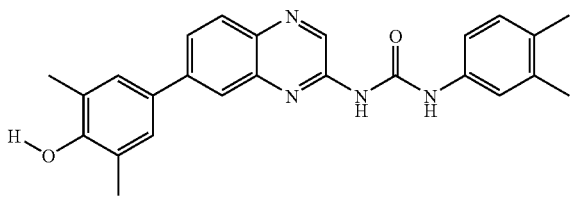 [SMILES: Cc1ccc(NC(=O)Nc2cnc3ccc(-c4cc(C)c(O)c(C)c4)cc3n2)cc1C]

¹H-NMR (300 MHz, DMSO-d₆) δ=11.14 (1H, s), 10.14 (1H, s), 8.93 (1H, m), 8.51 (1H, s), 7.95 (4H, m), 7.45 (4H, s), 7.15 (1H, s), 2.26 (6H, s), 2.15 (6H, s) ppm MS (ESI) m/z 413 (MH⁺)

Example 3.41

1-Allyl-3-[7-(4-hydroxy-3,5-dimethylphenyl)quinoxalin-2-yl]urea (41)

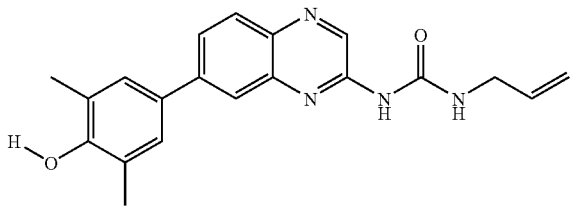 [SMILES: C=CCNC(=O)Nc1cnc2ccc(-c3cc(C)c(O)c(C)c3)cc2n1]

¹H-NMR (300 MHz, DMSO-d₆) δ=10.14 (1H, s), 8.93 (1H, m), 8.71 (1H, s), 8.54 (1H, s), 7.45 (3H, s), 5.97 (1H, s), 5.22 (2H, s), 3.95 (2H, m), 1.99 (6H, s) ppm MS (ESI) m/z 349 (MH⁺)

Example 3.42

1-Cyclooctyl-3-[7-(4-hydroxy-3,5-dimethylphenyl)quinoxalin-2-yl]urea (42)

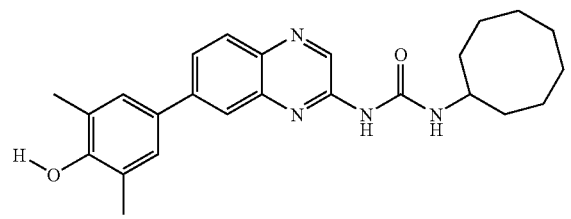 [SMILES: Cc1cc(-c2ccc3ncc(NC(=O)NC4CCCCCCC4)nc3c2)cc(C)c1O]

¹H-NMR (300 MHz, DMSO-d₆) δ=10.14 (1H, s), 8.93 (2H, m), 8.81 (1H, s), 7.85 (3H, m), 7.45 (2H, s), 4.08 (1H, m), 2.28 (6H, m), 1.95 (12H, m), 1.85 (2H, s) ppm MS (ESI) m/z 419 (MH⁺)

Example 3.43

1-(2,4-Dimethylphenyl)-3-[7-(4-hydroxy-3,5-dimethylphenyl)quinoxalin-2-yl]urea (43)

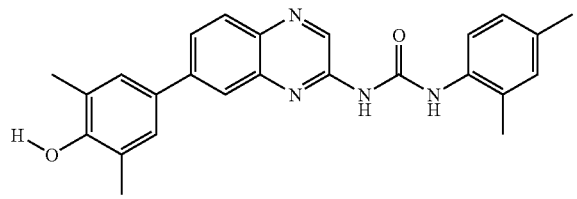 [SMILES: Cc1ccc(NC(=O)Nc2cnc3ccc(-c4cc(C)c(O)c(C)c4)cc3n2)c(C)c1]

¹H-NMR (300 MHz, DMSO-d₆) δ=11.14 (1H, s), 10.14 (1H, s), 8.93 (1H, m), 8.51 (1H, s), 7.95 (4H, m), 7.45 (4H, s), 7.15 (1H, s), 2.26 (6H, s), 2.15 (6H, s) ppm MS (ESI) m/z 413 (MH⁺)

Example 3.44

1-Cyclooctyl-3-[7-(4-hydroxy-3-methoxyphenyl)quinoxalin-2-yl]urea (44)

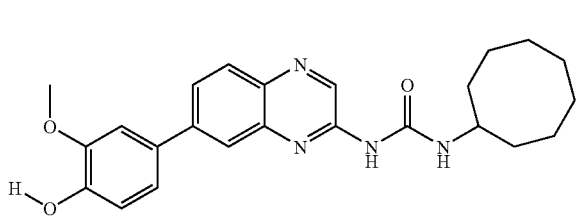 [SMILES: COc1cc(-c2ccc3ncc(NC(=O)NC4CCCCCCC4)nc3c2)ccc1O]

¹H-NMR (300 MHz, DMSO-d₆) δ=10.14 (1H, s), 9.03 (1H, m), 8.81 (2H, s), 8.00 (3H, m), 7.45 (2H, s), 6.93 (1H, s), 4.08 (1H, s), 3.88 (3H, s), 2.00 (2H, s), 1.75 (12H, s) ppm MS (ESI) m/z 421 (MH⁺)

Example 3.45

1-Adamantan-1-yl-3-(7-phenylquinoxalin-2-yl)urea (45)

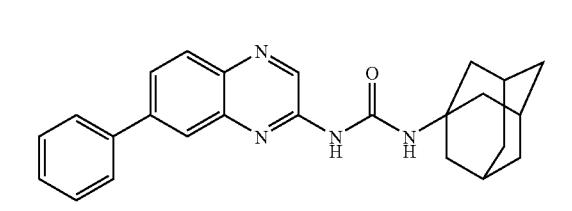 [SMILES: O=C(Nc1cnc2ccc(-c3ccccc3)cc2n1)NC12CC3CC(CC(C3)C1)C2]

¹H-NMR (300 MHz, DMSO-d₆) δ=10.14 (1H, s), 8.93 (2H, m), 8.00 (5H, m), 7.45 (3H, s), 2.00 (12H, s), 1.68 (3H, s) ppm MS (ESI) m/z 399 (MH⁺)

Example 3.46

1-[7-(4-Hydroxy-3,5-dimethylphenyl)quinoxalin-2-yl]-3-p-tolylurea (46)

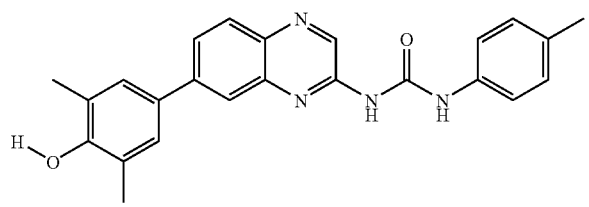 [SMILES: Cc1ccc(NC(=O)Nc2cnc3ccc(-c4cc(C)c(O)c(C)c4)cc3n2)cc1]

m.p.: >300° C.
MS (ESI) m/z 399 (MH$^+$)

Example 3.47

1-(3,4-Dichlorophenyl)-3-[7-(4-hydroxy-3,5-dimethylphenyl)quinoxalin-2-yl]urea (47)

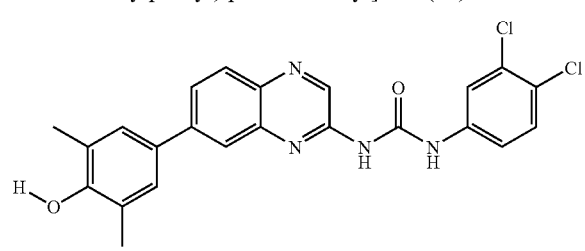

m.p.: >300° C.
MS (ESI) m/z 454 (MH$^+$)

Example 3.48

1-[7-(4-Hydroxy-3,5-dimethylphenyl)quinoxalin-2-yl]-3-(4-methoxy-phenyl)urea (48)

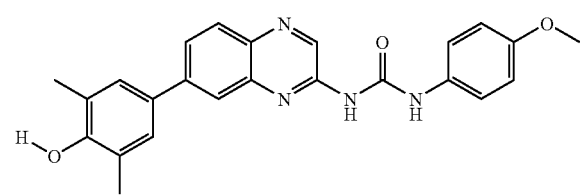 [SMILES: COc1ccc(NC(=O)Nc2cnc3ccc(-c4cc(C)c(O)c(C)c4)cc3n2)cc1]

m.p.: >300° C.
MS (ESI) m/z 415 (MH$^+$)

Example 3.49

1-Adamantan-1-yl-3-[7-(4-hydroxy-3,5-dimethylphenyl)quinoxalin-2-yl]urea (49)

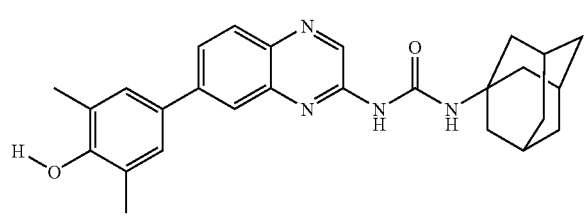 [SMILES: Cc1cc(-c2ccc3ncc(NC(=O)NC45CC6CC(CC(C6)C4)C5)nc3c2)cc(C)c1O]

$^1$H-NMR (300 MHz, DMSO-d$_6$) δ=10.14 (1H, s), 8.93 (2H, m), 8.81 (1H, s), 7.85 (3H, m), 7.45 (2H, s), 2.28 (6H, m), 1.85 (12H, m), 1.56 (3H, s) ppm
MS (ESI) m/z 443 (MH$^+$)

Example 3.50

1-[7-(4-Hydroxy-3,5-dimethylphenyl)quinoxalin-2-yl]-3-naphthalen-2-ylurea (50)

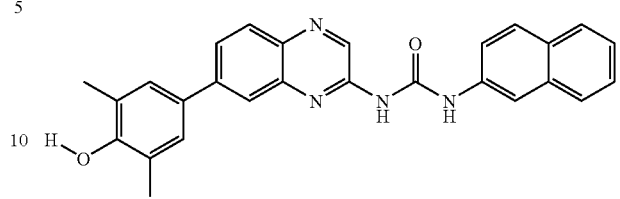

m.p.: >300° C.
MS (ESI) m/z 435 (MH$^+$)

Example 3.51

1-[7-(4-Hydroxy-3,5-dimethylphenyl)quinoxalin-2-yl]-3-(1,1,3,3-tetra-methylbutyl)urea (51)

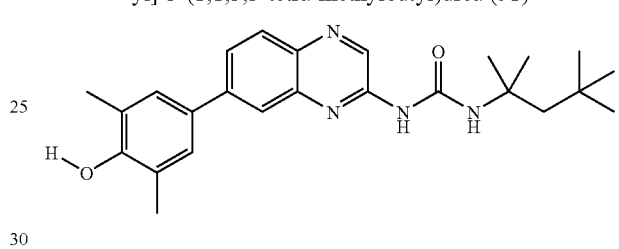

m.p.: >300° C.
MS (ESI) m/z 421 (MH$^+$)

Example 3.52

1-[7-(4-Hydroxy-3,5-dimethylphenyl)quinoxalin-2-yl]-3-pyridin-3-ylurea (52)

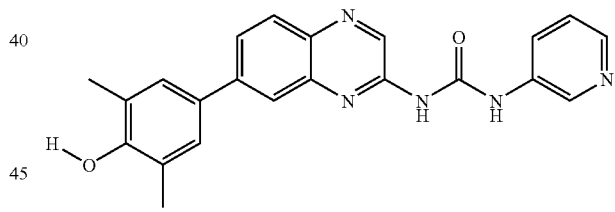

m.p.: 298-300° C.
MS (ESI) m/z 386 (MH$^+$)

Example 3.53

1-((R)-1,2-Dimethylpropyl)-3-[7-(4-hydroxy-3,5-dimethylphenyl)-quinoxalin-2-yl]urea (53)

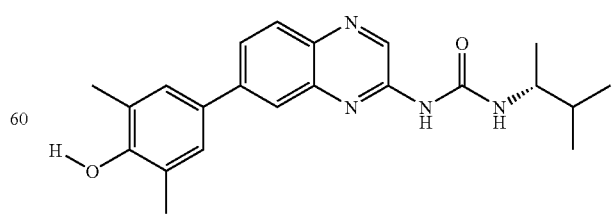

m.p.: 265° C.
MS (ESI) m/z 379 (MH$^+$)

Example 3.54

1-((S)-1,2-Dimethylpropyl)-3-[7-(4-hydroxy-3,5-dimethylphenyl)-quinoxalin-2-yl]urea (54)

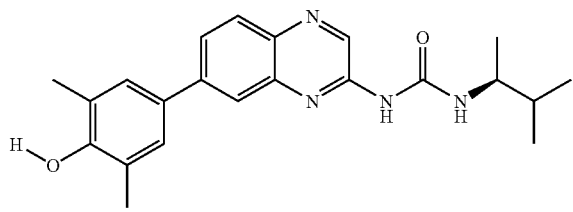 [SMILES: Cc1cc(-c2ccc3ncc(NC(=O)N[C@@H](C)C(C)C)nc3c2)cc(C)c1O]

m.p.: 267° C.
MS (ESI) m/z 379 (MH$^+$)

Example 3.55

1-(5-Chloro-2-methylphenyl)-3-[7-(4-hydroxy-3,5-dimethylphenyl)-quinoxalin-2-yl]urea (55)

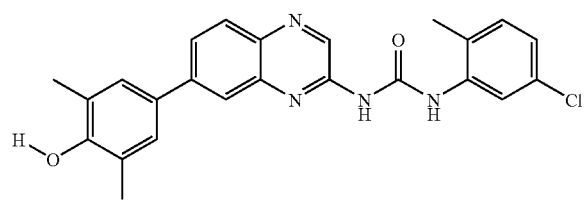 [SMILES: Cc1ccc(Cl)cc1NC(=O)Nc1cnc2ccc(-c3cc(C)c(O)c(C)c3)cc2n1]

$^1$H-NMR (300 MHz, DMSO-d$_6$) δ=11.14 (1H, s), 10.14 (1H, s), 8.93 (1H, m), 8.51 (1H, s), 7.95 (4H, m), 7.45 (4H, s), 7.15 (1H, s), 2.26 (6H, s), 2.15 (3H, s) ppm
MS (ESI) m/z 433 (MH$^+$)

Example 3.56

1-((S)-2-Phenylcyclopropyl)-3-(7-phenylquinoxalin-2-yl)urea (56)

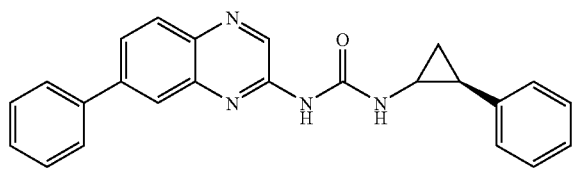 [SMILES: O=C(Nc1cnc2ccc(-c3ccccc3)cc2n1)NC1C[C@H]1c1ccccc1]

$^1$H-NMR (300 MHz, DMSO-d$_6$) δ=10.14 (1H, s), 8.93 (1H, m), 8.81 (1H, s), 8.00 (5H, m), 7.45 (3H, s), 7.32 (5H, s), 2.95 (1H, s), 2.05 (2H, m), 0.83 (1H, s) ppm
MS (ESI) m/z 381 (MH$^+$)

Example 3.57

1-[7-(4-Hydroxy-3,5-dimethylphenyl)quinoxalin-2-yl]-3-((S)-2-phenyl-cyclopropyl)urea (57)

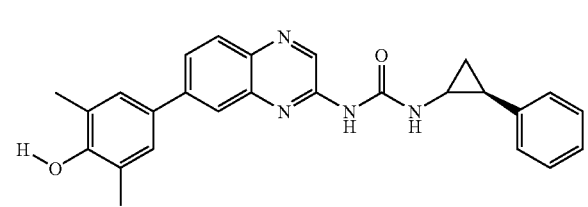 [SMILES: Cc1cc(-c2ccc3ncc(NC(=O)NC4C[C@H]4c4ccccc4)nc3c2)cc(C)c1O]

$^1$H-NMR (300 MHz, DMSO-d$_6$) δ=10.14 (1H, s), 8.93 (2H, m), 8.81 (1H, s), 8.00 (3H, m), 7.45 (2H, s), 7.28 (5H, s), 2.93 (1H, s), 2.28 (6H, m), 1.46 (2H, m), 0.83 (1H, s) ppm
MS (ESI) m/z 425 (MH$^+$)

Example 3.58

1-(2-Chloro-6-methylphenyl)-3-[7-(4-hydroxy-3,5-dimethylphenyl)-quinoxalin-2-yl]urea (58)

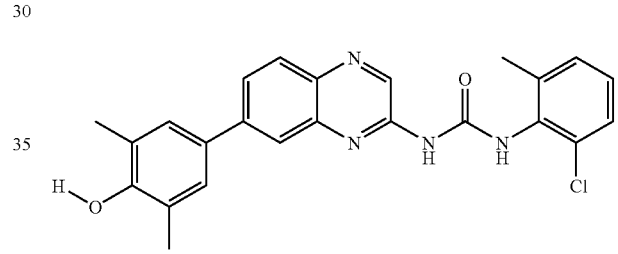

$^1$H-NMR (300 MHz, DMSO-d$_6$) δ=11.14 (1H, s), 10.14 (1H, s), 8.93 (1H, m), 8.51 (1H, s), 7.95 (4H, m), 7.45 (4H, s), 7.15 (1H, s), 2.26 (6H, s), 2.15 (3H, s) ppm
MS (ESI) m/z 433 (MH$^+$)

Example 3.59

1-Allyl-3-[7-(4-hydroxy-3-methoxyphenyl)quinoxalin-2-yl]urea (59)

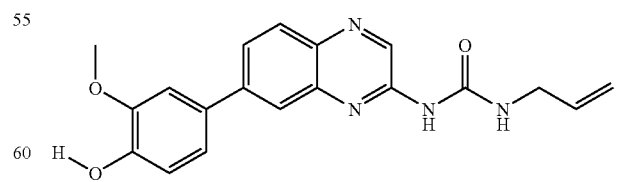

$^1$H-NMR (300 MHz, DMSO-d$_6$) δ=10.14 (1H, s), 9.03 (1H, m), 8.81 (2H, s), 8.00 (3H, m), 7.45 (2H, s), 6.93 (1H, s), 5.96 (1H, s), 5.21 (2H, m), 3.94 (2H, s), 3.88 (3H, s) ppm
MS (ESI) m/z 351 (MH$^+$)

Example 3.60

1-(3,5-Dimethylisoxazol-4-yl)-3-[7-(4-hydroxy-3,5-dimethylphenyl)-quinoxalin-2-yl]urea (60)

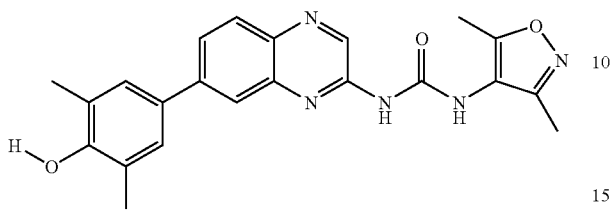

$^1$H-NMR (300 MHz, DMSO-d$_6$) δ=12.48 (1H, s), 8.42 (1H, s), 8.05 (1H, s), 7.84 (2H, s), 7.41 (1H, s), 2.47 (3H, s), 2.24 (6H, s), 2.18 (3H, s) ppm
MS (ESI) m/z 404 (MH$^+$)

Example 3.61

1-sec-Butyl-3-[7-(4-hydroxy-3,5-dimethylphenyl)quinoxalin-2-yl]urea (61)

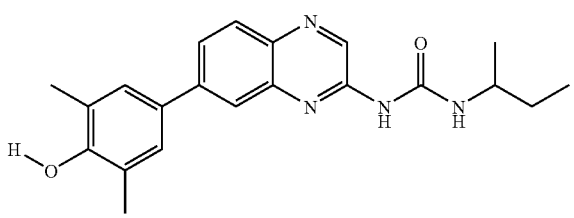 [SMILES: CCC(C)NC(=O)Nc1cnc2ccc(-c3cc(C)c(O)c(C)c3)cc2n1]

$^1$H-NMR (300 MHz, DMSO-d$_6$) δ=9.85 (1H, s), 8.84 (1H, s), 8.53-8.51 (2H, m), 7.93 (1H, d), 7.84 (2H, m), 7.41 (2H, s), 3.76 (1H, m), 2.24 (6H, s), 1.54 (2H, m), 1.21 (3H, d), 0.88 (3H, t) ppm
MS (ESI) m/z 365 (MH$^+$)

Example 3.62

1-Ethyl-3-[7-(4-methoxy-3,5-dimethylphenyl)quinoxalin-2-yl]urea (62)

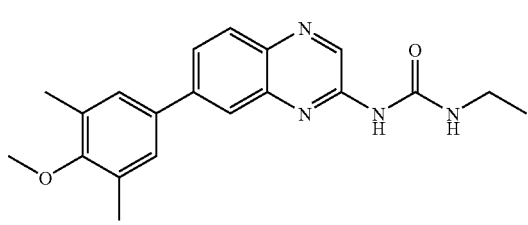 [SMILES: CCNC(=O)Nc1cnc2ccc(-c3cc(C)c(OC)c(C)c3)cc2n1]

$^1$H-NMR (300 MHz, DMSO-d$_6$) δ=10.03 (1H, s), 8.79 (2H, s), 8.08 (1H, d), 7.96 (1H, d), 7.88 (1H, m), 7.52 (2H, s), 3.71 (3H, s), 3.31 (2H, s), 2.33 (6H, s), 1.19 (3H, t) ppm
MS (ESI) m/z 351 (MH$^+$)

Example 3.63

1-Isopropyl-3-[7-(4-methoxy-3,5-dimethylphenyl)quinoxalin-2-yl]urea (63)

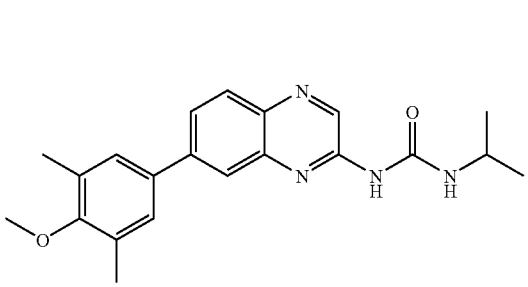 [SMILES: COc1c(C)cc(-c2ccc3ncc(NC(=O)NC(C)C)nc3c2)cc1C]

$^1$H-NMR (300 MHz, DMSO-d$_6$) δ=9.94 (1H, s), 8.87 (1H, s), 8.53-8.52 (1H, d), 7.98-7.95 (2H, m), 7.88-7.86 (2H, m), 7.51 (2H, s), 3.94-3.91(1H, m), 3.71 (3H, s), 2.33 (6H, s), 1.25-1.24 (6H, d) ppm
MS (ESI) m/z 365 (MH$^+$)

Example 3.64

1-Isopropyl-3-[7-(4-methoxy-3,5-dimethylphenyl)quinoxalin-2-yl]-thiourea (64)

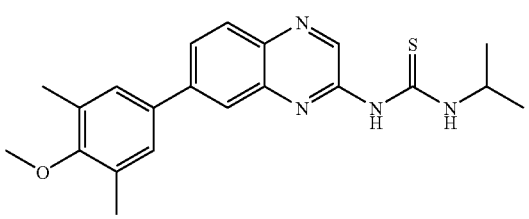 [SMILES: COc1c(C)cc(-c2ccc3ncc(NC(=S)NC(C)C)nc3c2)cc1C]

$^1$H-NMR (300 MHz, DMSO-d$_6$) δ=11.63 (1H, d), 11.17 (1H, s), 8.77 (1H, s), 7.99 (2H, m), 7.92 (1H, m), 7.52 (2H, s), 4.49-4.46 (1H, m), 3.71 (3H, s), 2.34 (6H, s), 1.38 (6H, d) ppm
MS (ESI) m/z 381 (MH$^+$)

Example 3.65

1-[7-(4-Hydroxy-3,5-dimethylphenyl)quinoxalin-2-yl]-3-isobutylurea (65)

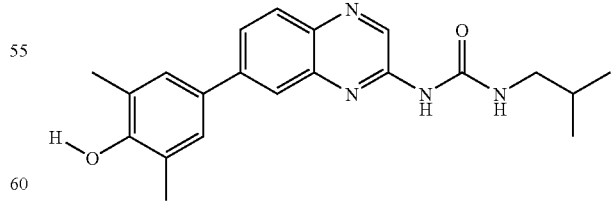

$^1$H-NMR (300 MHz, DMSO-d$_6$) δ=10.02 (1H, s), 8.85 (1H, m), 8.79 (1H, s), 8.53 (1H, s), 7.94-7.85 (3H, m), 7.41 (2H, s), 3.15-3.13 (2H, t), 2.27 (6H, s), 1.88-1.84 (1H, m), 0.95 (6H, d) ppm
MS (ESI) m/z 365 (MH$^+$)

Example 3.66

1-(1-Ethylpropyl)-3-[7-(4-hydroxy-3,5-dimethylphenyl)quinoxalin-2-yl]urea (66)

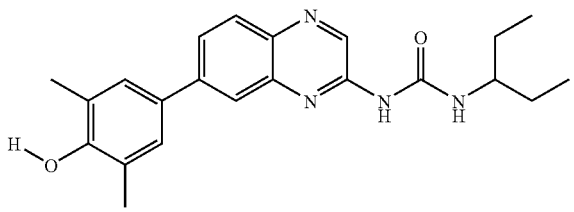 [SMILES: CCC(CC)NC(=O)Nc1cnc2ccc(-c3cc(C)c(O)c(C)c3)cc2n1]

$^1$H-NMR (300 MHz, DMSO-$d_6$) δ=9.92 (1H, s), 8.85 (1H, s), 8.52 (2H, s), 7.95 (1H, d), 7.85 (2H, m), 7.40 (2H, s), 3.67-3.64 (1H, m), 2.27 (6H, s), 1.63-1.52 (4H, m), 0.94-0.92 (6H, t) ppm
MS (ESI) m/z 379 (MH$^+$)

Example 3.67

1-(2,2-Dimethyl-propyl)-3-[7-(4-hydroxy-3,5-dimethyl-phenyl)-quinoxalin-2-yl]-urea (67)

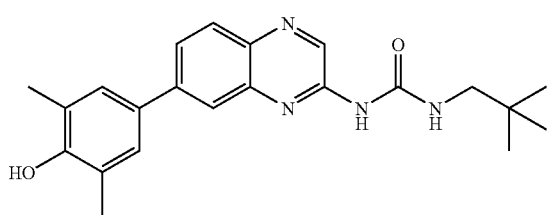 [SMILES: Cc1cc(-c2ccc3ncc(NC(=O)NCC(C)(C)C)nc3c2)cc(C)c1O]

m.p.: 275-276° C.
$^1$H-NMR (600 MHz, DMSO-$d_6$) δ=10.05 (1H, s), 8.91 (1H, s), 8.80 (1H, s), 8.54 (1H, s), 7.96 (1H, s), 7.87 (1H, s), 7.85 (1H, m), 7.38 (2H, s), 3.13 (2H, d), 2.26 (6H, s), 0.97 (9H, s) ppm
MS (ESI): m/z=379.3 (MH$^+$)

Example 3.68

1-[7-(4-Amino-phenyl)-quinoxalin-2-yl]-3-isopropyl-urea (68)

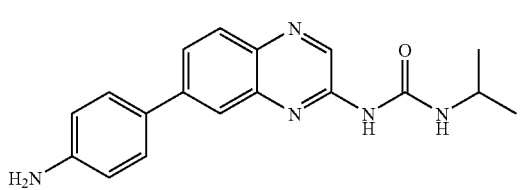 [SMILES: CC(C)NC(=O)Nc1cnc2ccc(-c3ccc(N)cc3)cc2n1]

m.p.: >300° C.
$^1$H-NMR (600 MHz, DMSO-$d_6$) δ=9.87 (1H, s), 8.77 (1H, s), 8.62 (1H, d), 7.91-7.84 (3H, m), 7.58-7.57 (2H, m), 6.71-6.69 (2H, m), 5.41 (2H, m), 3.94-3.90 (1H, m), 1.25-1.24 (6H, d) ppm
MS (ESI): m/z=322.0 (MH$^+$)

Example 3.69

1-[7-(4-Hydroxy-phenyl)-quinoxalin-2-yl]-3-isopropyl-urea (69)

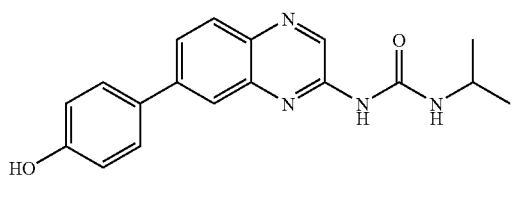 [SMILES: CC(C)NC(=O)Nc1cnc2ccc(-c3ccc(O)cc3)cc2n1]

$^1$H-NMR (600 MHz, DMSO-$d_6$) δ=9.94 (1H, s), 9.71 (1H, s), 8.82 (1H, s), 8.60 (1H, d), 7.96-7.86 (3H, m), 7.71-7.7 (2H, m), 6.92-6.91 (2H, m), 3.94-3.90 (1H, m), 1.25-1.24 (6H, d) ppm
MS (ESI): m/z=322.9 (MH$^+$)

Example 3.70

1-Isopropyl-3-[7-(1-methyl-1H-pyrazol-4-yl)-quinoxalin-2-yl]-urea (70)

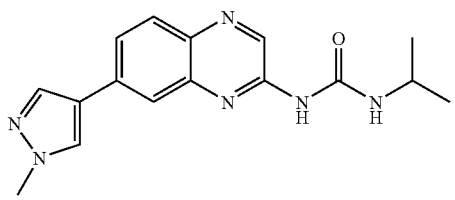 [SMILES: CC(C)NC(=O)Nc1cnc2ccc(-c3cnn(C)c3)cc2n1]

m.p.: 260-263° C.
$^1$H-NMR (600 MHz, DMSO-$d_6$) δ=9.91 (1H, s), 8.78 (1H, s), 8.60 (1H, d), 8.39 (1H, s), 8.10 (1H, s), 7.91-7.89 (2H, m), 7.85-7.83 (1H, m), 3.91 (4H, m), 1.26-1.25 (6H, d) ppm
MS (ESI): m/z=311.2 (MH$^+$)

Example 3.71

1-[7-(3,5-Dichloro-4-hydroxy-phenyl)-quinoxalin-2-yl]-3-pentyl-urea (71)

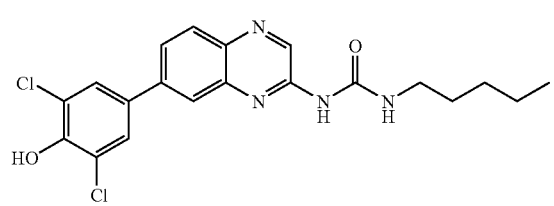 [SMILES: CCCCCNC(=O)Nc1cnc2ccc(-c3cc(Cl)c(O)c(Cl)c3)cc2n1]

m.p.: 297-298° C.
$^1$H-NMR (600 MHz, DMSO-$d_6$) δ=10.41 (1H, s), 10.08 (1H, s), 8.91 (1H, s), 8.78 (1H, s), 8.10 (1H, m), 7.98-7.87 (4H, m), 3.29 (2H, m), 1.61-1.56 (2H, m), 1.38-1.35 (4H, m), 0.93-0.94 (3H, t) ppm
MS (ESI): m/z=421.1 (MH$^+$)

Example 3.72

1-Butyl-3-[7-(3,5-dichloro-4-hydroxy-phenyl)-quinoxalin-2-yl]-urea (72)

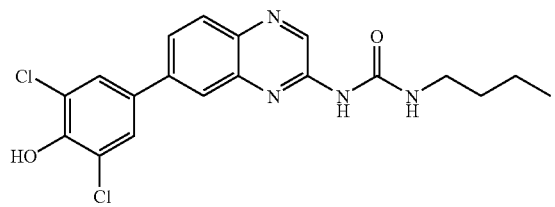

m.p.: 297-298° C.
$^1$H-NMR (600 MHz, DMSO-$d_6$) δ=10.42 (1H, s), 10.06 (1H, s), 8.80 (2H, m), 8.10 (1H, m), 7.98-7.88 (4H, m), 3.29 (2H, s), 1.58-1.56 (2H, m), 1.41-1.37 (2H, m), 0.96-0.93 (3H, m) ppm
MS (ESI): m/z=405.1, 407.8 (MH$^+$)

Example 3.73

1-[7-(3,5-Dichloro-4-hydroxy-phenyl)-quinoxalin-2-yl]-3-propyl-urea (73)

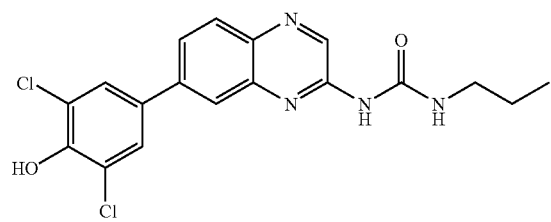 [SMILES: CCCNC(=O)Nc1cnc2ccc(-c3cc(Cl)c(O)c(Cl)c3)cc2n1]

m.p.: 295-296° C.
$^1$H-NMR (600 MHz, DMSO-$d_6$) δ=10.44 (1H, s), 10.06 (1H, s), 8.85-8.80 (2H, m), 8.13 (1H, s), 7.97-7.88 (4H, m), 3.28-3.24 (2H, m), 1.62-1.56 (2H, m), 0.95-0.91 (3H, t) ppm
MS (ESI): m/z=391.2, 392.9 (MH$^+$)

Example 3.74

1-[7-(3,5-Dichloro-4-hydroxy-phenyl)-quinoxalin-2-yl]-3-ethyl-urea (74)

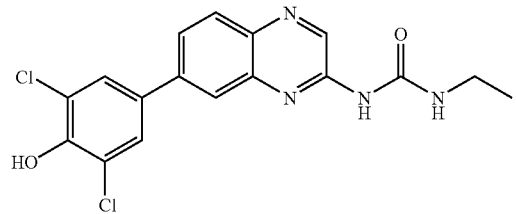

m.p.: 295-296° C.
$^1$H-NMR (600 MHz, DMSO-$d_6$) δ=10.44 (1H, s), 10.07 (1H, s), 8.86 (1H, m), 8.78 (1H, s), 8.18 (1H, m), 7.97-7.90 (4H, m), 3.35-3.30 (2H, m), 1.23-1.18 (3H, t) ppm
MS (ESI): m/z=377.1 (MH$^+$)

Example 3.75

1-[7-(3,5-Dichloro-4-hydroxy-phenyl)-quinoxalin-2-yl]-3-heptyl-urea (75)

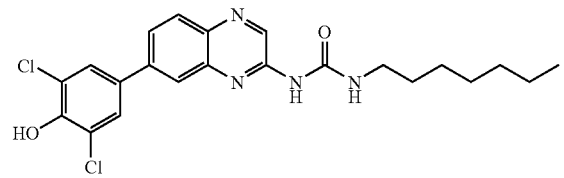 [SMILES: CCCCCCCNC(=O)Nc1cnc2ccc(-c3cc(Cl)c(O)c(Cl)c3)cc2n1]

m.p.: 289-291° C.
$^1$H-NMR (600 MHz, DMSO-$d_6$) δ=10.41 (1H, s), 10.08 (1H, s), 8.93 (1H, s), 8.77 (1H, s), 8.08 (1H, m), 7.96 (1H, m), 7.93-7.9 (1H, m), 7.86 (2H, s), 3.28 (2H, m), 1.60-1.55 (2H, m), 1.40-1.27 (8H, m), 0.83-0.81 (3H, t) ppm
MS (ESI): m/z=447.1 (MH$^+$)

Example 3.76

1-[7-(3,5-Dichloro-4-hydroxy-phenyl)-quinoxalin-2-yl]-3-isopropyl-urea (76)

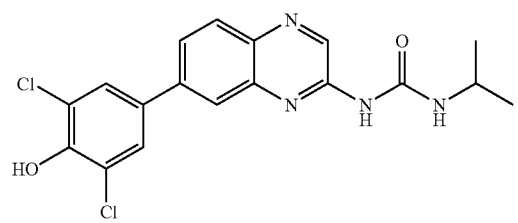

m.p.: 298-300° C.
$^1$H-NMR (600 MHz, DMSO-$d_6$) δ=10.44 (1H, s), 9.96 (1H, s), 8.87 (1H, s), 8.54 (1H, s), 8.05 (1H, m), 7.98 (1H, m), 7.93 (1H, m), 7.88 (2H, m), 3.95-3.91 (1H, m), 1.26-1.25 (6H, d) ppm
MS (ESI): m/z=391.1 (MH$^+$)

Example 3.77

1-tert-Butyl-3-[7-(3,5-dichloro-4-hydroxy-phenyl)-quinoxalin-2-yl]-urea (77)

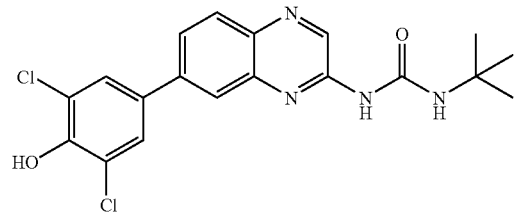 [SMILES: CC(C)(C)NC(=O)Nc1cnc2ccc(-c3cc(Cl)c(O)c(Cl)c3)cc2n1]

m.p.: 292-295° C.
$^1$H-NMR (600 MHz, DMSO-$d_6$) δ=10.45 (1H, s), 9.85 (1H, s), 8.86 (1H, s), 8.67 (1H, s), 7.98-7.96 (1H, m), 7.92-7.90 (2H, m), 7.86 (2H, s), 1.42 (9H, m) ppm
MS (ESI): m/z=405.1 (MH$^+$)

Example 3.78

1-Cycloheptyl-3-[7-(3,5-dichloro-4-hydroxy-phenyl)-quinoxalin-2-yl]-urea (78)

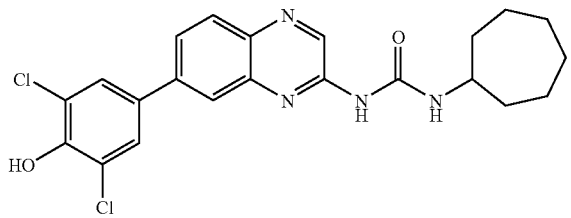 [SMILES: O=C(Nc1cnc2ccc(-c3cc(Cl)c(O)c(Cl)c3)cc2n1)NC1CCCCCC1]

m.p.: 283-286° C.
$^1$H-NMR (600 MHz, DMSO-d$_6$) δ=10.45 (1H, s), 9.99 (1H, s), 8.87 (1H, s), 8.67 (1H, m), 7.98-7.97 (2H, m), 7.92-7.91 (2H, m), 7.86 (1H, s), 3.87-3.83 (1H, m), 1.92-1.88 (2H, m), 1.68-1.50 (10H, m) ppm
MS (ESI): m/z=445.1 (MH$^+$)

Example 3.79

1-Cyclooctyl-3-[7-(3,5-dichloro-4-hydroxy-phenyl)-quinoxalin-2-yl]-urea (79)

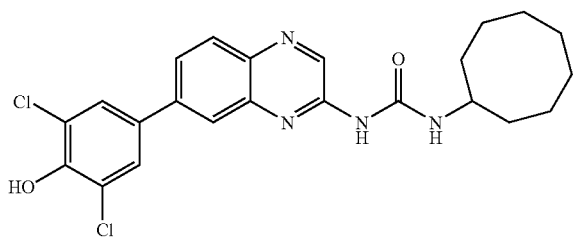

m.p.: 258-260° C.
$^1$H-NMR (600 MHz, DMSO-d$_6$) δ=10.44 (1H, s), 9.97 (1H, s), 8.88 (1H, s), 8.67 (1H, m), 7.98-7.91 (3H, m), 7.85 (2H, s), 3.89-3.87 (1H, m), 1.89-1.84 (2H, m), 1.73-1.55 (12H, m) ppm
MS (ESI): m/z=459.4 (MH$^+$)

Example 3.80

1-Cyclobutyl-3-[7-(3,5-dichloro-4-hydroxy-phenyl)-quinoxalin-2-yl]-thiourea (80)

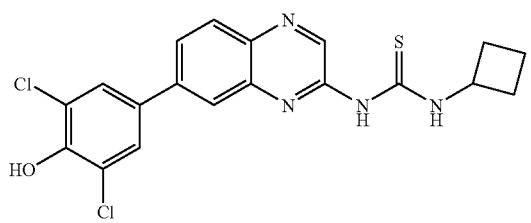 [SMILES: Oc1c(Cl)cc(-c2ccc3ncc(NC(=S)NC4CCC4)nc3c2)cc1Cl]

m.p.: 277-280° C.
$^1$H-NMR (600 MHz, DMSO-d$_6$) δ=11.74-11.73 (1H, d), 11.25 (1H, s), 10.46 (1H, s), 8.79 (1H, s), 8.17 (1H, s), 7.99-7.98 (2H, m), 7.92 (2H, s), 4.73-4.67 (1H, m), 2.44-2.40 (2H, m), 2.25-2.20 (2H, m), 1.84-1.75 (2H, m) ppm
MS (ESI): m/z=418.9 (MH$^+$)

Example 3.81

1-Cyclopentyl-3-[7-(3,5-dichloro-4-hydroxy-phenyl)-quinoxalin-2-yl]-urea (81)

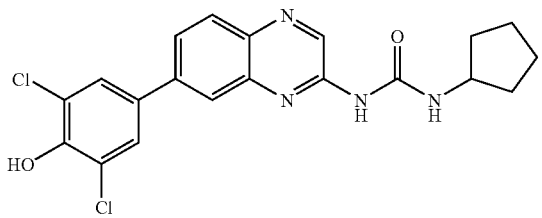 [SMILES: O=C(Nc1cnc2ccc(-c3cc(Cl)c(O)c(Cl)c3)cc2n1)NC1CCCC1]

m.p.: 295-296° C.
$^1$H-NMR (600 MHz, DMSO-d$_6$) δ=10.44 (1H, s), 9.96 (1H, s), 8.89 (1H, s), 8.60 (1H, m), 7.99-7.97 (2H, m), 7.92-7.91 (1H, m), 7.87 (2H, s), 4.10-4.07 (1H, m), 1.95-1.92 (2H, m), 1.74-1.73 (2H, m), 1.62-1.56 (4H, m) ppm
MS (ESI): m/z=417.1 (MH$^+$)

Example 3.82

1-[7-(3-Chloro-4-hydroxy-5-methoxy-phenyl)-quinoxalin-2-yl]-3-isopropyl-urea (82)

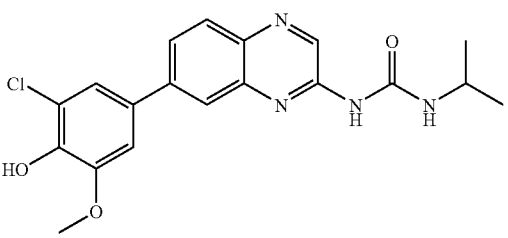 [SMILES: COc1cc(-c2ccc3ncc(NC(=O)NC(C)C)nc3c2)cc(Cl)c1O]

$^1$H-NMR (600 MHz, DMSO-d$_6$) δ=9.92 (1H, s), 9.68 (1H, s), 8.88 (1H, s), 8.51 (1H, s), 8.01-7.92 (3H, m), 7.44 (1H, d), 7.38 (1H, d), 3.97 (3H, s), 3.94-3.91 (1H, m), 1.25 (6H, d) ppm
MS (ESI): m/z=387.3 (MH$^+$)

Example 3.83

1-Cyclopropyl-3-[7-(3,5-dichloro-4-hydroxy-phenyl)-quinoxalin-2-yl]-thiourea (83)

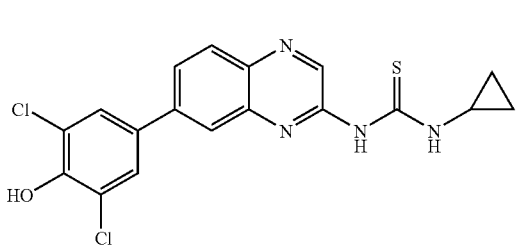 [SMILES: Oc1c(Cl)cc(-c2ccc3ncc(NC(=S)NC4CC4)nc3c2)cc1Cl]

m.p.: 260-262° C.
$^1$H-NMR (600 MHz, DMSO-d$_6$) δ=11.59 (1H, d), 11.31 (1H, s), 10.50 (1H, s), 8.78 (1H, s), 8.16 (1H, s), 7.98 (2H, s), 7.93 (2H, s), 3.25-3.20 (1H, m), 0.91-0.90 (4H, m) ppm
MS (ESI): m/z=405.2 (MH$^+$)

Example 3.84

1-[7-(3,5-Dichloro-4-hydroxy-phenyl)-quinoxalin-2-yl]-3-(3-phenyl-propyl)-urea (84)

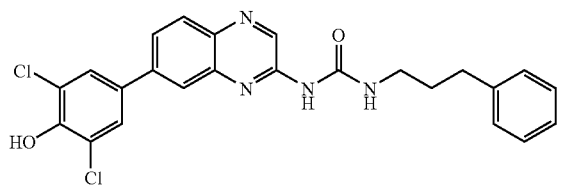

m.p.: 271-274° C.
$^1$H-NMR (600 MHz, DMSO-d$_6$) δ=10.42 (1H, s), 10.10 (1H, s), 8.86 (1H, s), 8.79 (1H, s), 8.13 (1H, s), 7.98 (1H, m), 7.94-7.93 (1H, m), 7.87 (2H, s), 7.28-7.17 (5H, m), 3.31 (2H, s), 2.70-2.68 (2H, t), 1.91-1.89 (2H, m) ppm
MS (ESI): m/z=467.3 (MH$^+$)

Example 3.85

1-[7-(3,5-Dichloro-4-hydroxy-phenyl)-quinoxalin-2-yl]-3-phenethyl-urea (85)

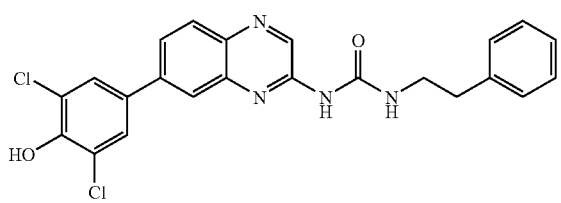

$^1$H-NMR (600 MHz, DMSO-d$_6$) δ=10.45 (1H, s), 10.16 (1H, s), 9.00 (1H, s), 8.70 (1H, s), 7.94-7.91 (2H, m), 7.82 (2H, s), 7.70 (1H, s), 7.32-7.36 (4H, m), 7.21 (1H, t), 3.63-3.61 (2H, m), 2.91-2.89 (2H, t) ppm
MS (ESI): m/z=453.1, 455.9 (MH$^+$)

Example 3.86

1-[7-(3,5-Dichloro-4-hydroxy-phenyl)-quinoxalin-2-yl]-3-phenyl-urea (86)

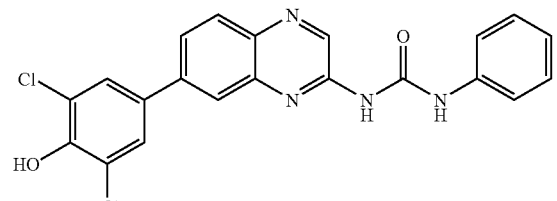

m.p.: >300° C.
$^1$H-NMR (600 MHz, DMSO-d$_6$) δ=10.96 (1H, s), 10.45 (1H, s), 10.37 (1H, s), 8.95 (1H, s), 8.26 (1H, m), 8.03-8.02 (2H, m), 7.98-7.95 (2H, m), 7.73-7.71 (2H, d), 7.4-7.37 (2H, t), 7.10-7.09 (1H, t) ppm
MS (ESI): m/z=425.1, 427.2 (MH$^+$)

Example 3.87

1-Butyl-3-[7-(3,5-dichloro-4-hydroxy-phenyl)-quinoxalin-2-yl]thiourea (87)

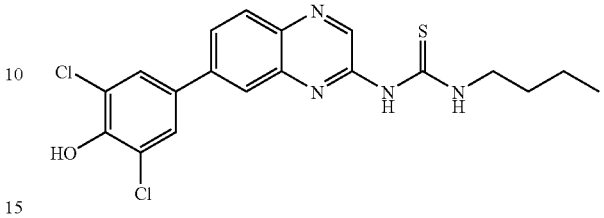

m.p.: 226-227° C.
$^1$H-NMR (600 MHz, DMSO-d$_6$) δ=11.71 (1H, t), 11.23 (1H, s), 10.49 (1H, s), 8.79 (1H, s), 8.16 (1H, s), 7.99 (2H, s), 7.88 (2H, s), 3.74-3.71 (2H, m), 1.75-1.70 (2H, m), 1.47-1.43 (2H, m), 0.99-0.97 (3H, t) ppm
MS (ESI): m/z=421.2, 425.3 (MH$^+$)

Example 3.88

1-[7-(3,5-Dichloro-4-hydroxy-phenyl)-quinoxalin-2-yl]-3-ethyl-thiourea (88)

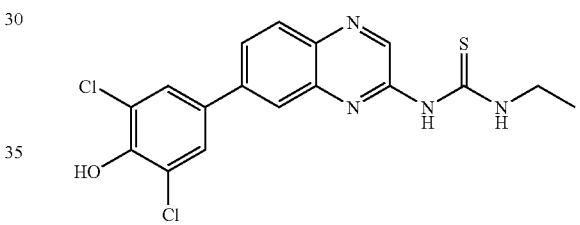

m.p.: 237-238° C.
$^1$H-NMR (600 MHz, DMSO-d$_6$) δ=11.65-11.63 (1H, t), 11.21 (1H, s), 10.47 (1H, s), 8.78 (1H, s), 8.27 (1H, s), 7.99 (2H, s), 7.90 (2H, s), 3.79-3.74 (2H, m), 1.32-1.30 (3H, t) ppm
MS (ESI): m/z=393.1, 395.2 (MH$^+$)

Example 3.89

1-[7-(3,5-Dichloro-4-hydroxy-phenyl)-quinoxalin-2-yl]-3-propyl-thiourea (89)

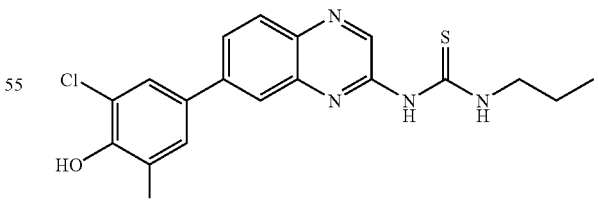

m.p.: 237-239° C.
$^1$H-NMR (600 MHz, DMSO-d$_6$) δ=11.69-11.67 (1H, t), 11.23 (1H, s), 10.48 (1H, s), 8.79 (1H, s), 8.2 (1H, s), 7.99 (2H, m), 7.88 (2H, s), 3.71-3.68 (2H, m), 1.78-1.74 (2H, m), 1.00-0.98 (3H, t) ppm
MS (ESI): m/z=407.1, 409.3 (MH$^+$)

Example 3.90

1-[7-(3,5-Dichloro-4-hydroxy-phenyl)-quinoxalin-2-yl]-3-pentyl-thiourea (90)

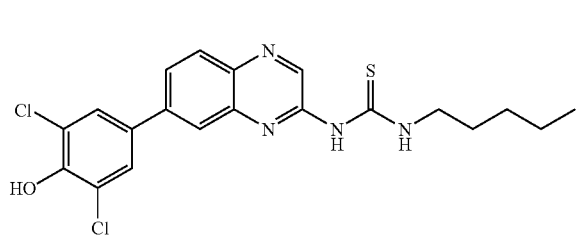 [SMILES: CCCCCNC(=S)Nc1cnc2ccc(-c3cc(Cl)c(O)c(Cl)c3)cc2n1]

m.p.: 237-238° C.
$^1$H-NMR (600 MHz, DMSO-$d_6$) δ=11.72-11.70 (1H, t), 11.24 (1H, s), 10.49 (1H, s), 8.78 (1H, s), 8.13 (1H, s), 8.00 (2H, m), 7.87 (2H, s), 3.73-3.70 (2H, m), 1.76-1.72 (2H, m), 1.44-1.40 (4H, m), 0.95-0.92 (3H, t) ppm
MS (ESI): m/z=435.2 (MH$^+$)

Example 3.91

1-[7-(3,5-Dichloro-4-hydroxy-phenyl)-quinoxalin-2-yl]-3-isopropyl-thiourea (91)

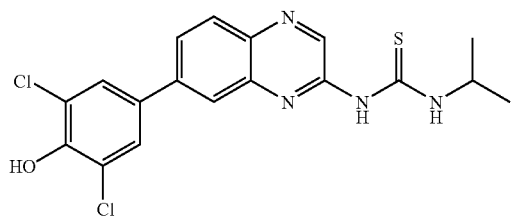

m.p.: 276-278° C.
$^1$H-NMR (600 MHz, DMSO-$d_6$) δ=11.60-11.59 (1H, d), 11.18 (1H, s), 10.46 (1H, s), 8.79 (1H, s), 8.10 (1H, s), 7.98 (2H, s), 4.49-4.47 (1H, m), 1.39-1.38 (6H, d) ppm
MS (ESI): m/z=407.1 (MH$^+$)

Example 3.92

1-Cycloheptyl-3-[7-(3,5-dichloro-4-hydroxy-phenyl)-quinoxalin-2-yl]-thiourea (92)

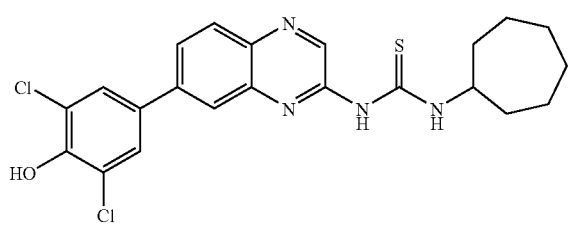

m.p.: 281-283° C.
$^1$H-NMR (600 MHz, DMSO-$d_6$) δ=11.73-11.71 (1H, d), 11.20 (1H, s), 10.50 (1H, s), 8.79 (1H, s), 7.99-7.97 (3H, m), 7.85 (2H, s), 4.46-4.41 (1H, m), 2.04-1.99 (2H, m), 1.87-1.81 (2H, m), 1.73-1.69 (2H, m), 1.65-1.64 (4H, m), 1.61-1.57 (2H, m) ppm
MS (ESI): m/z=461.2 (MH$^+$)

Example 3.93

1-Cyclooctyl-3-[7-(3,5-dichloro-4-hydroxy-phenyl)-quinoxalin-2-yl]-thiourea (93)

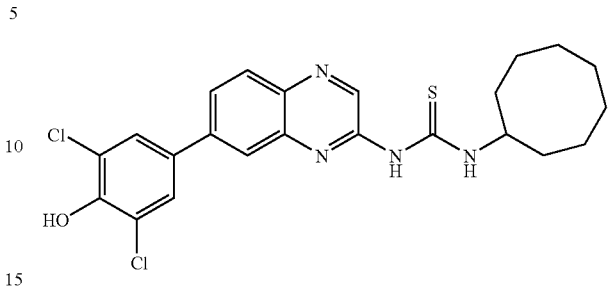

m.p.: 288-289° C.
$^1$H-NMR (600 MHz, DMSO-$d_6$) δ=11.82-11.81 (1H, d), 11.2 (1H, s), 10.5 (1H, s), 8.78 (1H, s), 7.99-7.95 (3H, m), 7.85 (2H, s), 4.52-4.48 (1H, m), 2.01-1.95 (2H, m), 1.87-1.83 (2H, m), 1.77-1.73 (2H, m), 1.67-1.61 (8H, m) ppm
MS (ESI): m/z=475.5 (MH$^+$)

Example 3.94

1-Benzyl-3-[7-(3,5-dichloro-4-hydroxy-phenyl)-quinoxalin-2-yl]-thiourea (94)

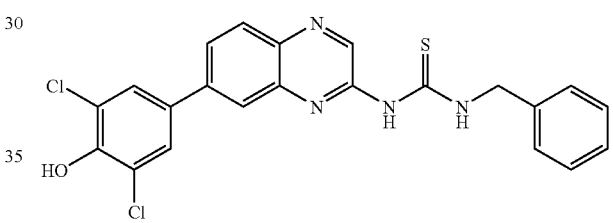

m.p.: 275-277° C.
$^1$H-NMR (600 MHz, DMSO-$d_6$) δ=12.19-12.18 (1H, t), 11.39 (1H, s), 10.50 (1H, s), 8.80 (1H, s), 8.05 (1H, s), 7.99 (2H, s), 7.83 (2H, s), 7.48-7.47 (2H, m), 7.41-7.38 (2H, m), 7.32-7.31 (1H, m), 4.98-4.97 (2H, d) ppm
MS (ESI): m/z=455.2 (MH$^+$)

Example 3.95

1-[7-(3-Chloro-4-hydroxy-phenyl)-quinoxalin-2-yl]-3-isopropyl-urea (95)

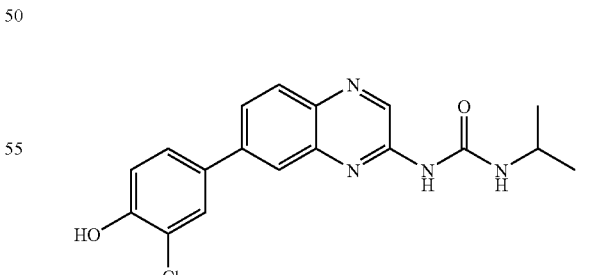

m.p.: 275-277
$^1$H-NMR (600 MHz, DMSO-$d_6$) δ=10.50 (1H, s), 9.95 (1H, s), 8.84 (1H, s), 8.57 (1H, m), 7.98-7.95 (2H, m), 7.89-7.87 (1H, m), 7.85-7.84 (1H, m), 7.68-7.66 (1H, m), 7.12-11 (1H, d), 3.94-3.91 (1H, m), 1.25-1.24 (6H, m) ppm
MS (ESI): m/z=357.2 (MH$^+$)

Example 3.96

1-[7-(3,5-Dichloro-4-hydroxy-phenyl)-quinoxalin-2-yl]-3-(3-phenyl-propyl)-thiourea (96)

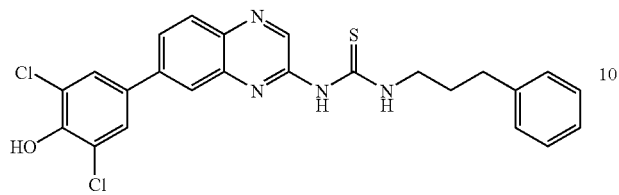

m.p.: 248-250° C.
$^1$H-NMR (600 MHz, DMSO-$d_6$) δ=11.72-11.7 (1H, t), 11.26 (1H, s), 10.50 (1H, s), 8.79 (1H, s), 8.17 (1H, m), 7.99 (2H, m), 7.87 (2H, s), 7.28-7.24 (4H, m), 7.16-7.14 (1H, m), 3.77-3.73 (2H, m), 2.75-2.73 (2H, m), 2.09-2.07 (2H, m) ppm
MS (ESI): m/z=481.2, 483.4 (MH$^+$)

Example 3.97

1-[7-(3,5-Dichloro-4-hydroxy-phenyl)-quinoxalin-2-yl]-3-phenethyl-thiourea (97)

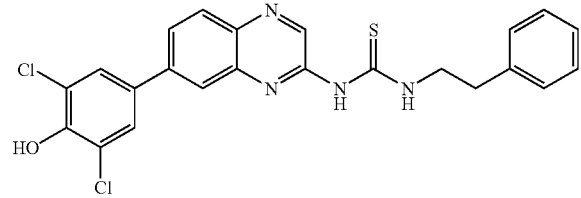

m.p.: 282-285° C.
$^1$H-NMR (600 MHz, DMSO-$d_6$) δ=11.61-11.58 (1H, t), 11.29 (1H, s), 10.53 (1H, s), 8.76 (1H, s), 7.97 (2H, m), 7.83 (2H, s), 7.68 (1H, m), 7.40-7.39 (2H, m), 7.33-7.29 (2H, m), 7.2-7.17 (1H, m), 4.07-4.04 (2H, m), 3.06-3.04 (2H, t) ppm
MS (ESI): m/z=469.1 (MH$^+$)

Biological Actions of the Compounds According to the Invention

Example 4

Antiproliferative Action in Various Tumour Cell Lines

The antiproliferative action of the compounds of the general formula I according to the invention was determined using the proliferation tests:

a) Alamar Blue assay (Page et al. Int. J. Oncology 1993, 3, 473)

b) XTT assay (Scuderio et al. Cancer Res. 1988, 48, 4827).

The cell lines used are the cell line KB/HeLa (cervix), the cell line SKOV-3 (ovaries), the cell line NCI-H460 (lung), the cell line PC3 (prostate), HCT-116 (colon), the cell line MDA-MB468 (breast), the cell line A549 (lung), the cell line U87MG (glioma), the cell line L363 (leukaemia), the cell line TMM (leukaemia), the cell line RKOp27 (colon), the cell line RS4,11 (leukaemia), the cell line HSB-2 (leukaemia), the cell line NALM-6 (leukaemia), the cell line MOLT-3 (leukaemia), the cell line MOLT-16 (leukaemia), the cell line MCF-7 (breast), the cell line MDA-MBA435 (breast) and the cell line LnCap (prostate).

The cytotoxic and growth-inhibitory activities of the compounds according to the invention are shown in Tables 1a and 1b. The results show highly potent inhibition of the proliferation of selected tumour cell lines by the substances mentioned.

TABLE 1a

| | | | | Proliferation assay, EC50 in [µM] | | | | | | |
|---|---|---|---|---|---|---|---|---|---|---|
| Vbb | NCI-H460 | SKOV-3 | HCT116 | MDA MB468 | PC-3 | A549 | U87MG | L363 | TMM | RKOP27 |
| 17 | 0.047 | 0.04 | 0.024 | 0.039 | 0.028 | 0.029 | 0.010 | 0.078 | 0.032 | 0.026 |
| 9 | 0.238 | 0.248 | 0.229 | 0.263 | 0.112 | 0.289 | 0.181 | n.d. | n.d. | 0.176 |
| 12 | 0.085 | 0.067 | 0.042 | 0.125 | 0.051 | 0.076 | 0.077 | n.d. | n.d. | n.d. |
| 15 | 0.714 | 1.81 | 0.475 | 0.835 | 0.309 | 0.836 | 1.336 | n.d. | n.d. | n.d. |
| 18 | 0.038 | 0.032 | 0.021 | 0.030 | 0.016 | 0.046 | 0.008 | n.d. | n.d. | n.d. |
| 22 | 0.027 | 0.030 | 0.007 | 0.053 | 0.011 | 0.008 | 0.002 | n.d. | n.d. | 0.028 |
| 23 | 0.021 | 0.016 | 0.003 | 0.148 | 0.003 | 0.009 | 0.002 | n.d. | n.d. | 0.020 |
| 31 | 0.060 | 0.045 | 0.030 | 0.025 | 0.015 | 0.023 | 0.013 | n.d. | n.d. | n.d. |
| 32 | 0.030 | 0.027 | 0.016 | 0.020 | 0.009 | 0.009 | 0.003 | n.d. | n.d. | n.d. |
| 34 | 0.052 | 0.050 | 0.036 | 0.030 | 0.012 | 0.016 | 0.224 | n.d. | n.d. | 0.058 |
| 36 | 0.064 | 0.042 | 0.043 | 0.043 | 0.009 | 0.034 | 0.111 | n.d. | n.d. | n.d. |
| 41 | 0.218 | n.d. | 0.091 | 0.131 | 0.076 | 0.217 | 0.105 | n.d. | n.d. | n.d. |
| 67 | n.d. | n.d. | 0.325 | 0.384 | 0.188 | 0.352 | 0.222 | n.d. | n.d. | n.d. |
| 68 | n.d. | n.d. | 0.474 | 1.67 | 0.453 | 0.626 | 0.529 | n.d. | n.d. | n.d. |
| 70 | n.d. | n.d. | 0.564 | 0.991 | 0.601 | 1.32 | 0.801 | n.d. | n.d. | n.d. |
| 72 | n.d. | n.d. | 1.82 | 0.779 | 0.880 | 3.26 | 3.19 | n.d. | n.d. | n.d. |
| 73 | n.d. | n.d. | 1.56 | 0.814 | 1.18 | 3.36 | 4.14 | n.d. | n.d. | n.d. |
| 74 | n.d. | n.d. | 3.09 | 2.10 | 2.20 | 3.91 | 10.0 | n.d. | n.d. | n.d. |
| 78 | n.d. | n.d. | 0.809 | 0.436 | 0.306 | 1.18 | 3.11 | n.d. | n.d. | n.d. |
| 79 | n.d. | n.d. | 0.503 | 0.253 | 0.300 | 1.03 | 1.16 | n.d. | n.d. | n.d. |
| 80 | n.d. | n.d. | 1.71 | 0.672 | 1.19 | 2.04 | 2.00 | n.d. | n.d. | n.d. |
| 83 | n.d. | n.d. | 2.09 | 1.05 | 0.955 | 2.29 | 1.97 | n.d. | n.d. | n.d. |
| 85 | n.d. | n.d. | 1.30 | 1.61 | 1.26 | 1.84 | 0.495 | n.d. | n.d. | n.d. |
| 87 | n.d. | n.d. | 1.09 | 0.464 | 0.790 | 1.53 | 2.49 | n.d. | n.d. | n.d. |
| 90 | n.d. | n.d. | 1.01 | 0.318 | 0.556 | 1.09 | 1.23 | n.d. | n.d. | n.d. |
| 93 | n.d. | n.d. | 0.409 | 0.193 | 0.334 | 1.03 | 1.80 | n.d. | n.d. | n.d. |
| 94 | n.d. | n.d. | 0.586 | 0.169 | 0.821 | 0.891 | 2.08 | n.d. | n.d. | n.d. |

TABLE 1a-continued

| | Proliferation assay, EC50 in [µM] | | | | | | | | | |
|---|---|---|---|---|---|---|---|---|---|---|
| Vbb | NCI-H460 | SKOV-3 | HCT116 | MDA MB468 | PC-3 | A549 | U87MG | L363 | TMM | RKOP27 |
| 96 | n.d. | n.d. | 1.54 | 1.04 | 1.65 | 1.82 | 2.35 | n.d. | n.d. | n.d. |
| 97 | n.d. | n.d. | 0.700 | 0.568 | 0.538 | 1.51 | 1.82 | n.d. | n.d. | n.d. |

TABLE 1b

| | Proliferation assay, EC50 in [µM] | | | | | | | | |
|---|---|---|---|---|---|---|---|---|---|
| Vbb | RS4, 11 | HSB-2 | NALM-6 | MOLT-3 | MOLT-16 | KB-HeLa | MCF-7 | MDA-MB435 | LNCaP |
| 17 | 0.037 | 0.037 | 0.054 | 0.036 | 0.056 | 0.037 | 0.032 | 0.018 | 0.040 |

Table 1a/1b: Growth inhibition of substances according to the invention in the proliferation assay in tumour cell lines Example 5

Antiproliferative Action in Resistant Tumour Cell Lines

For further characterization, the substances according to the invention were examined in resistant tumour cell lines compared to non-resistant wild-type tumour cell lines.

The cell lines examined are the cell line A2780 (ovary), the cis-platin-resistant cell line A2780 (ovary), the cell line L1210 (leukaemia), the vincristine-resistant cell line L1210 (leukaemia), the cell line MESSA (uterus), the doxorubicin-resistant cell line MESSA Dx5 (uterus), the cell line NCIH69 (lung) and the multi-drug-resistant cell line NCIH69 AR (lung).

The results are summarized in Table 3 below:

TABLE 3

Inhibitory action of quinoxalines in the XTT proliferation test in non-resistant and resistant tumour cell lines.

| | Proliferation assay, EC$_{50}$ in [µM] | | | | | | | |
|---|---|---|---|---|---|---|---|---|
| Vbb | A2780 | A2780 cis-Pt | L1210 | L1210 VCR | MESSA | MESSA DX5 | NCI H69 | NCI H69 AR |
| 17 | 0.0003 | 0.0005 | 0.002 | 0.004 | 0.152 | 0.139 | 0.027 | 0.086 |
| 22 | 0.018 | 0.014 | 0.015 | 0.019 | 0.141 | 0.038 | 0.010 | 0.008 |
| 23 | 0.022 | 0.019 | 0.005 | 0.004 | 0.048 | 0.016 | 0.004 | 0.0008 |

The quinoxalines of the formula I according to the invention show highly potent inhibitory action in all the cell lines tested.

The invention claimed is:
1. A quinoxaline compound represented by formula I

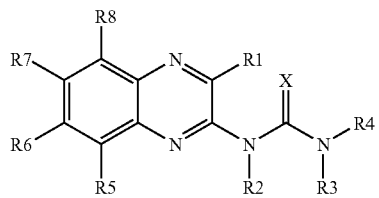

Formula I in which
X is: oxygen or sulphur;

$R_1$ is:
  (i) hydrogen,
  (ii) unsubstituted or substituted $(C_1$-$C_{12})$-alkyl,
  (iii) cyano,
  (iv) halogen,
$R_2$ and $R_3$ are independently:
  (i) hydrogen,
  (ii) unsubstituted or substituted $(C_1$-$C_{12})$-alkyl,
$R_4$ is:
  (i) hydrogen,
  (ii) unsubstituted or substituted $(C_1$-$C_{12})$-alkyl,
  (iii) unsubstituted or substituted cycloalkyl,
  (iv) unsubstituted or substituted heterocyclyl,
  (v) unsubstituted or substituted alkylaryl,
  (vi) unsubstituted or substituted alkylheteroaryl,
and
$R_5$ and $R_8$ are independently:
  (i) hydrogen,
  (ii) unsubstituted or substituted $(C_1$-$C_{12})$-alkyl,
  (iii) unsubstituted or substituted aryl,
  (iv) unsubstituted or substituted heteroaryl,
  (v) halogen,
  (vi) cyano,
  (vii) hydroxy,
  (viii) $(C_1$-$C_{12})$-alkoxy,
  (ix) amino,
  (x) carboxy, alkoxycarbonyl, carboxyalkyl or alkoxycarbonylalkyl,
  (xi) alkoxycarbonylamino, alkoxycarbonylaminoalkyl, and
$R_6$, $R_7$ are independently:
  (i) hydrogen,
  (ii) unsubstituted or substituted aryl,
  (iii) unsubstituted or substituted heteroaryl,
  (iv) halogen,
  (v) cyano,
  (vi) hydroxy,
  (vii) $(C_1$-$C_{12})$-alkoxy, (viii) amino,
(ix) carboxy, alkoxycarbonyl, carboxyalkyl or alkoxycarbonylalkyl,
(x) alkoxycarbonylamino, alkoxycarbonylaminoalkyl, and with the proviso that at least one of $R_5$, $R_6$, $R_7$ and $R_8$ are independently an unsubstituted or substituted aryl or heteroaryl radical, and where the substituents are selected from the group consisting of F, Cl, Br, I, CN, $CF_3$, $NH_2$, NH-alkyl, NH-aryl, N(alkyl)$_2$, NH—CO-alkyl, NH—CO-aryl, NH—CO-heteroaryl, NH—SO$_2$-alkyl, NH—SO$_2$-aryl, NH—SO$_2$-heteroaryl, NH—CO—NH-alkyl, NH—CO—NH-aryl, NH—CO—NH-heteroaryl, NH—C(O)O-alkyl, NH—C(O)O-aryl, NH—C(O)O-heteroaryl, $NO_2$, SH, S-alkyl, OH, $OCF_3$, O-alkyl, O-aryl, O—CO-alkyl, O—CO-aryl, O—CO-heteroaryl, O—C(O)O-alkyl, O—C(O)O-aryl, O—C(O)O-heteroaryl, O—CO—NH-alkyl, O—CO—N(alkyl)$_2$, O—CO—NH-aryl, O—CO—NH-heteroaryl, $OSO_3H$, $OSO_2$-alkyl, $OSO_2$-aryl, $OSO_2$-heteroaryl, OP(O)(OH)$_2$, alkyl-P(O)(OH)$_2$CHO, $CO_2H$, C(O)O-alkyl, C(O)O-aryl, C(O)O-heteroaryl, CO-alkyl, CO-aryl, CO-heteroaryl, $SO_3H$, $SO_2$—$NH_2$, $SO_2$—NH-alkyl, $SO_2$—NH-aryl, $SO_2$—NH-heteroaryl, alkyl, cycloalkyl, heterocyclyl, aryl and heteroaryl, where the radicals "alkyl", "cycloalkyl", "heterocyclyl", "aryl" and "heteroaryl" may also be substituted, or a physiologically acceptable salt, stereoisomer or tautomer thereof.

2. The quinoxaline compound represented by formula I according to claim 1 in which
X is independently oxygen or sulphur;
$R_1$ is independently
  (i) hydrogen,
  (ii) unsubstituted or substituted ($C_1$-$C_{12}$)-alkyl,
$R_2$ and $R_3$ are independently
  (i) hydrogen,
  (ii) unsubstituted or substituted ($C_1$-$C_{12}$)-alkyl,
$R_4$ is independently
  (i) hydrogen,
  (ii) unsubstituted or substituted ($C_1$-$C_{12}$)-alkyl,
  (iii) unsubstituted or substituted ($C_3$-$C_8$)-cycloalkyl,
  (iv) unsubstituted or substituted piperidyl,
  (v) unsubstituted or substituted benzyl,
$R_5$ and $R_8$ are independently
  (i) hydrogen,
  (ii) unsubstituted or substituted ($C_1$-$C_{12}$)-alkyl,
$R_7$ is
  (i) hydrogen,
and
substituent $R_6$ is
  (i) unsubstituted or substituted phenyl,
and where the substituents are selected from the group consisting of F, Cl, Br, I, CN, $CF_3$, $NH_2$, NH-alkyl, NH-aryl, N(alkyl)$_2$, NH—CO-alkyl, NH—CO-aryl, NH—CO-heteroaryl, NH—SO$_2$-alkyl, NH—SO$_2$-aryl, NH—SO$_2$-heteroaryl, NH—CO—NH-alkyl, NH—CO—NH-aryl, NH—CO—NH-heteroaryl, NH—C(O)O-alkyl, NH—C(O)O-aryl, NH—C(O)O-heteroaryl, $NO_2$, SH, S-alkyl, OH, $OCF_3$, O-alkyl, O-aryl, O—CO-alkyl, O—CO-aryl, O—CO-heteroaryl, O—C(O)O-alkyl, O—C(O)O-aryl, O—C(O)O-heteroaryl, O—CO—NH-alkyl, O—CO—N(alkyl)$_2$, O—CO—NH-aryl, O—CO—NH-heteroaryl, $OSO_3H$, $OSO_2$-alkyl, $OSO_2$-aryl, $OSO_2$-heteroaryl, OP(O)(OH)$_2$, alkyl-P(O)(OH)$_2$ CHO, $CO_2H$, C(O)O-alkyl, C(O)O-aryl, C(O)O-heteroaryl, CO-alkyl, CO-aryl, CO-heteroaryl, $SO_3H$, $SO_2$—$NH_2$, $SO_2$—NH-alkyl, $SO_2$—NH-aryl, $SO_2$—NH-heteroaryl, alkyl, cycloalkyl, heterocyclyl, aryl and heteroaryl, where the radicals "alkyl", "cycloalkyl", "heterocyclyl", "aryl" and "heteroaryl" may also be substituted.

3. The quinoxaline compound represented by formula I according to claim 1 in which
X is oxygen or sulphur;
$R_1$ is independently
  (i) hydrogen,
  (ii) unsubstituted or substituted ($C_1$-$C_{12}$)-alkyl,
  (iii) cyano,
  (iv) halogen,
$R_2$ and $R_3$ are independently
  (i) hydrogen,
  (ii) unsubstituted or substituted ($C_1$-$C_{12}$)-alkyl,
$R_4$ is independently
  (i) hydrogen,
  (ii) unsubstituted or substituted ($C_1$-$C_{12}$)-alkyl,
  (iii) unsubstituted or substituted cycloalkyl,
  (iv) unsubstituted or substituted heterocyclyl,
  (v) unsubstituted or substituted alkylaryl,
  (vi) unsubstituted or substituted alkylheteroaryl,
$R_5$ and $R_8$ are independently
  (i) hydrogen,
  (ii) unsubstituted or substituted ($C_1$-$C_{12}$)-alkyl,
  (iii) unsubstituted or substituted aryl,
  (iv) unsubstituted or substituted heteroaryl,
  (v) halogen,
  (vi) cyano,
  (vii) hydroxy,
  (viii) ($C_1$-$C_{12}$)-alkoxy,
  (ix) amino,
  (x) carboxy, alkoxycarbonyl, carboxyalkyl or alkoxycarbonylalkyl,
  (xi) alkoxycarbonylamino, alkoxycarbonylaminoalkyl,
$R_7$ is
  (i) hydrogen,
  (ii) unsubstituted or substituted aryl,
  (iii) unsubstituted or substituted heteroaryl,
  (iv) halogen,
  (v) cyano,
  (vi) hydroxy,
  (vii) ($C_1$-$C_{12}$)-alkoxy,
  (viii) amino,
  (ix) carboxy, alkoxycarbonyl, carboxyalkyl or alkoxycarbonylalkyl,
  (x) alkoxycarbonylamino, alkoxycarbonylaminoalkyl,
where the substituents are selected from the group consisting of F, Cl, Br, I, CN, $CF_3$, $NH_2$, NH-alkyl, NH-aryl, N(alkyl)$_2$, NH—CO-alkyl, NH—CO-aryl, NH—CO-heteroaryl, NH—SO$_2$-alkyl, NH—SO$_2$-aryl, NH—SO$_2$-heteroaryl NH—CO—NH-alkyl, NH—CO—NH-aryl, NH—CO—NH-heteroaryl, NH—C(O)O-alkyl, NH—C(O)O-aryl, NH—C(O)O-heteroaryl, $NO_2$, SH, S-alkyl, OH, $OCF_3$, O-alkyl, O-aryl, O—CO-alkyl, O—CO-aryl, O—CO-heteroaryl, O—C(O)O-alkyl, O—C(O)O-aryl, O—C(O)O-heteroaryl, O—CO—NH-alkyl, O—CO—N(alkyl)$_2$, O—CO—NH-aryl, O—CO—NH-heteroaryl, $OSO_3H$, $OSO_2$-alkyl, $OSO_2$-aryl, $OSO_2$-heteroaryl, OP(O)(OH)$_2$, alkyl-P(O)(OH)$_2$CHO, $CO_2H$, C(O)O-alkyl, C(O)O-aryl, C(O)O-heteroaryl, CO-alkyl, CO-aryl, CO-heteroaryl, $SO_3H$, $SO_2$—$NH_2$, $SO_2$—NH-alkyl, $SO_2$—NH-aryl, $SO_2$—NH-heteroaryl, alkyl, cycloalkyl, heterocyclyl, aryl and heteroaryl, where the radicals "alkyl", "cycloalkyl", "heterocyclyl", "aryl" and "heteroaryl" may also be substituted, and $R_6$ is independently
   (i) unsubstituted or substituted aryl,
   (ii) unsubstituted or substituted heteroaryl,
   where the substituents are selected from the group consisting of halogen, $(C_1-C_{12})$-alkyl, hydroxy, and $(C_1-C_{12})$-alkoxy.

4. The quinoxaline compound represented by formula I according to claim 1, wherein the quinoxaline is 1-[7-(4-hydroxy-3,5-dimethyl-phenyl)quinoxalin-2-yl]-3-isopropylurea

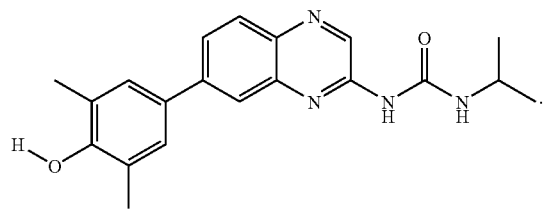 [SMILES: Cc1cc(-c2ccc3ncc(NC(=O)NC(C)C)nc3c2)cc(C)c1O]

5. The quinoxaline compound represented by formula I according to claim 1, wherein the quinoxaline is 1-ethyl-3-[7-(4-hydroxy-3,5-dimethyl-phenyl)quinoxalin-2-yl]thiourea

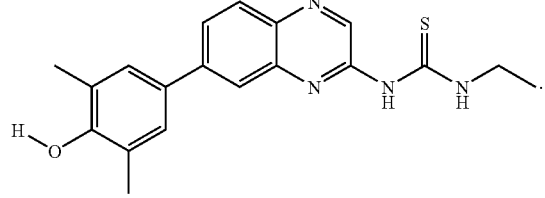

6. The quinoxaline compound represented by formula I according to claim 1, wherein the quinoxaline is 1-cyclopropyl-3-[7-(4-hydroxy-3,5-dimethylphenyl)quinoxalin-2-yl]thiourea

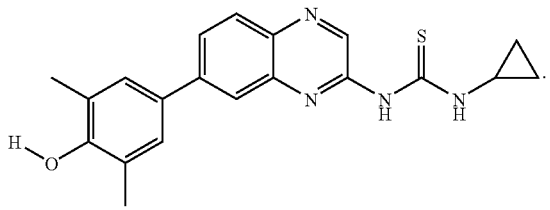 [SMILES: Cc1cc(-c2ccc3ncc(NC(=S)NC4CC4)nc3c2)cc(C)c1O]

7. The quinoxaline compound represented by formula I according to claim 1, wherein the quinoxaline is 1-[7-(3,5-Dichloro-4-hydroxy-phenyl)-quinoxalin-2-yl]-3-(2-thiophen-2-yl-ethyl)-urea

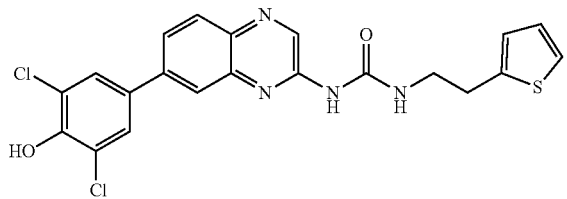 [SMILES: O=C(NCCc1cccs1)Nc1cnc2ccc(-c3cc(Cl)c(O)c(Cl)c3)cc2n1]

or a physiologically acceptable salt, stereoisomer or tautomer thereof.

8. The quinoxaline compound represented by formula I according to claim 1 or a physiologically acceptable salt, stereoisomer or tautomer thereof, selected from the group consisting of:

1-cyclopentyl-3-[7-(4-hydroxy-3-methoxy-phenyl)quinoxalin-2-yl]urea

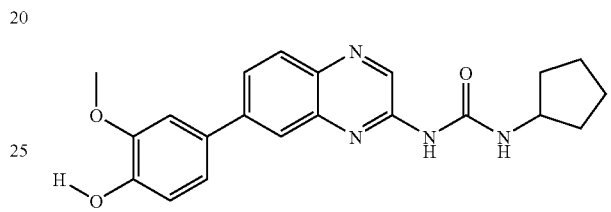

1-cyclohexyl-3-[7-(4-hydroxy-3-methoxyphenyl)quinoxalin-2-yl]urea

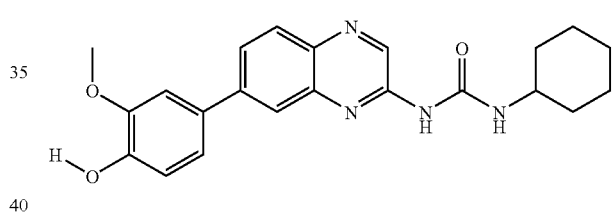

1-cyclohexyl-3-[7-(3,4-dimethoxyphenyl)quinoxalin-2-yl]urea

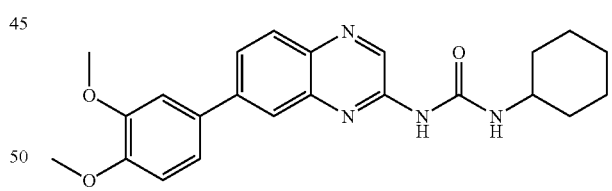

1-[7-(3,4-dimethoxyphenyl)quinoxalin-2-yl]-3-[1-(2,2,2-trifluoro-acetyl)-piperidin-4-yl]urea

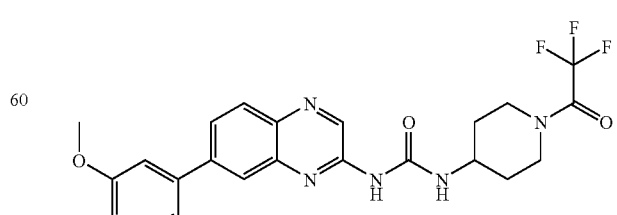

1-[7-(4-hydroxy-3-methoxyphenyl)quinoxalin-2-yl]-3-[1-(2,2,2-trifluoroacetyl)-piperidin-4-yl]urea

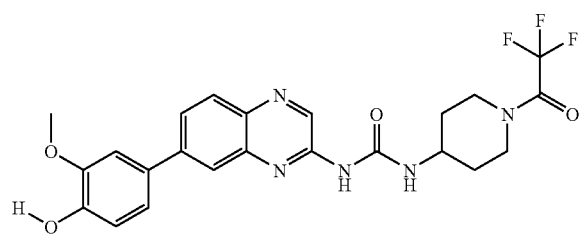 [SMILES: COc1cc(-c2ccc3ncc(NC(=O)NC4CCN(C(=O)C(F)(F)F)CC4)nc3c2)ccc1O]

1-benzyl-3-[7-(4-hydroxy-3-methoxyphenyl)quinoxalin-2-yl]urea

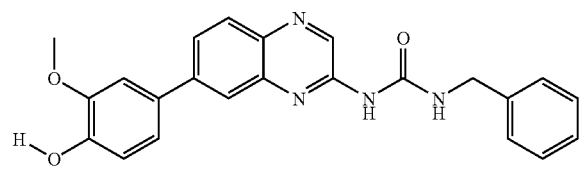 [SMILES: COc1cc(-c2ccc3ncc(NC(=O)NCc4ccccc4)nc3c2)ccc1O]

1-cyclopentyl-3-[7-(3,4-dimethoxyphenyl)quinoxalin-2-yl]urea

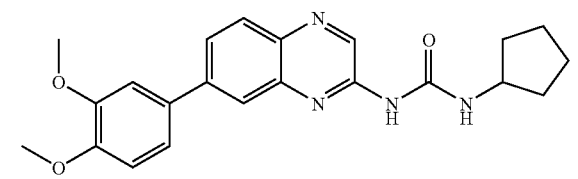 [SMILES: COc1ccc(-c2ccc3ncc(NC(=O)NC4CCCC4)nc3c2)cc1OC]

1-tert-butyl-3-[7-(4-hydroxy-3,5-dimethylphenyl)quinoxalin-2-yl]urea

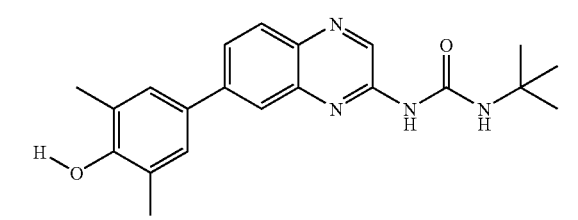 [SMILES: Cc1cc(-c2ccc3ncc(NC(=O)NC(C)(C)C)nc3c2)cc(C)c1O]

1-tert-butyl-3-[7-(4-hydroxy-3-methoxyphenyl)quinoxalin-2-yl]urea

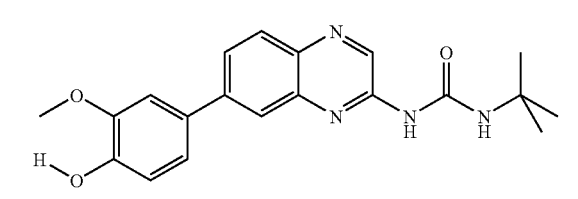 [SMILES: COc1cc(-c2ccc3ncc(NC(=O)NC(C)(C)C)nc3c2)ccc1O]

1-cyclohexyl-3-[7-(4-hydroxy-3,5-dimethylphenyl)quinoxalin-2-yl]urea

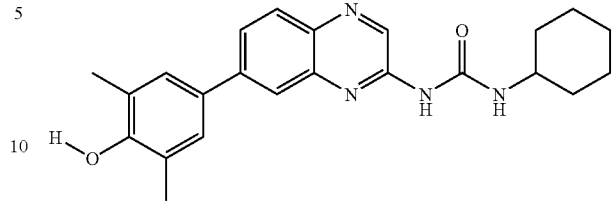

1-cyclopentyl-3-[7-(4-hydroxy-3,5-dimethylphenyl)quinoxalin-2-yl]urea

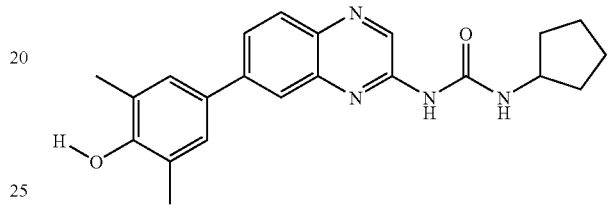

1-[7-(4-hydroxy-3,5-dimethylphenyl)quinoxalin-2-yl]-3-methylurea

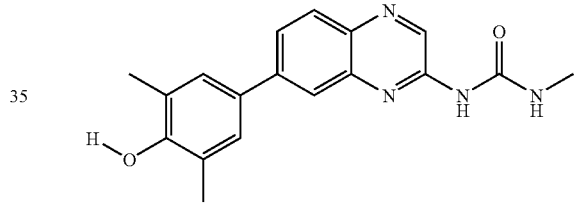

1-[7-(4-hydroxy-3,5-dimethylphenyl)quinoxalin-2-yl]-3-isopropylurea

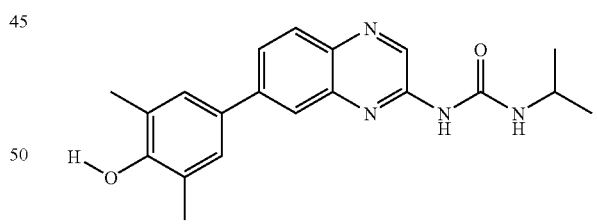

1-butyl-3-[7-(4-hydroxy-3,5-dimethylphenyl)quinoxalin-2-yl]urea

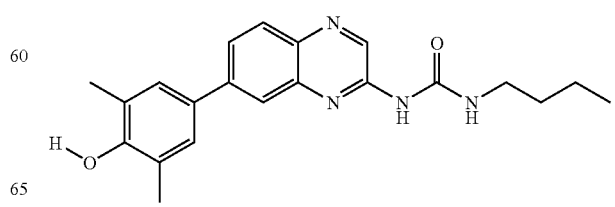

1-ethyl-3-[7-(4-hydroxy-3,5-dimethylphenyl)quinoxalin-2-yl]urea

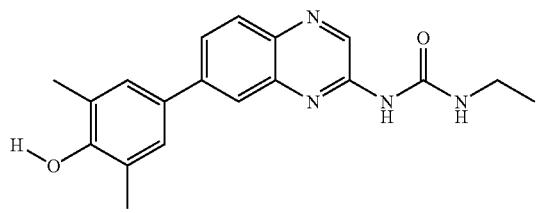 [SMILES: CCNC(=O)Nc1cnc2ccc(-c3cc(C)c(O)c(C)c3)cc2n1]

1-cyclohexyl-3-[7-(4-hydroxy-3,5-dimethylphenyl)quinoxalin-2-yl]thiourea

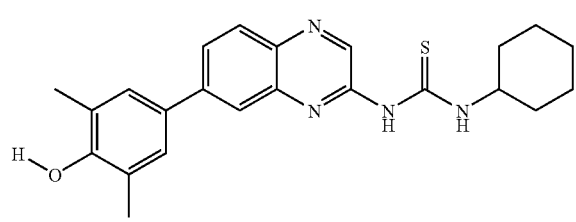

1-cyclohexyl-3-[7-(3,5-dichloro-4-hydroxyphenyl)quinoxalin-2-yl]thiourea

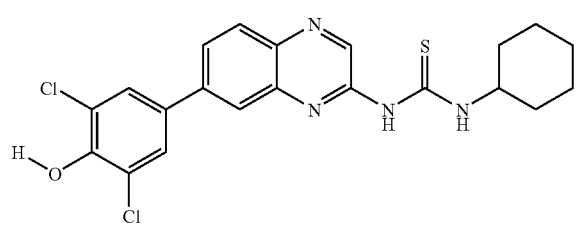 [SMILES: Oc1c(Cl)cc(-c2ccc3ncc(NC(=S)NC4CCCCC4)nc3c2)cc1Cl]

1-ethyl-3-[7-(4-hydroxy-3,5-dimethylphenyl)quinoxalin-2-yl]thiourea

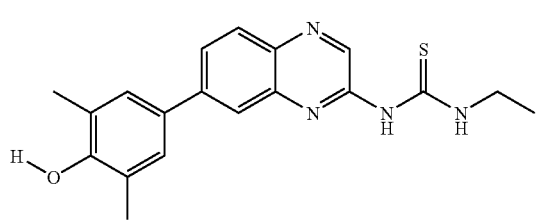 [SMILES: CCNC(=S)Nc1cnc2ccc(-c3cc(C)c(O)c(C)c3)cc2n1]

1-cyclopropyl-3-[7-(4-hydroxy-3,5-dimethylphenyl)quinoxalin-2-yl]thiourea

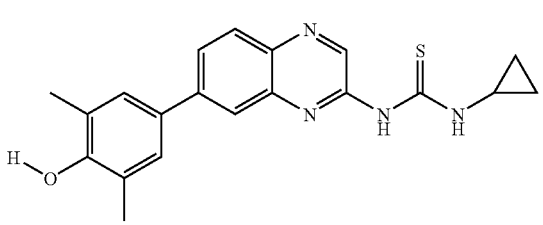 [SMILES: Cc1cc(-c2ccc3ncc(NC(=S)NC4CC4)nc3c2)cc(C)c1O]

1-cyclopentyl-3-[7-(4-hydroxy-3,5-dimethylphenyl)quinoxalin-2-yl]thiourea

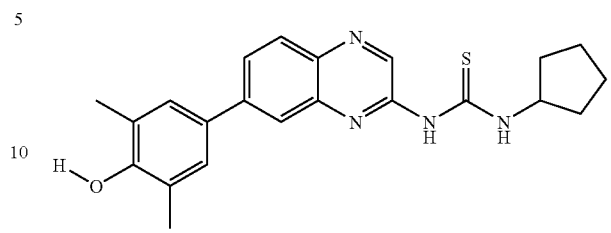

1-tert-butyl-3-[7-(4-hydroxy-3,5-dimethylphenyl)quinoxalin-2-yl]thiourea

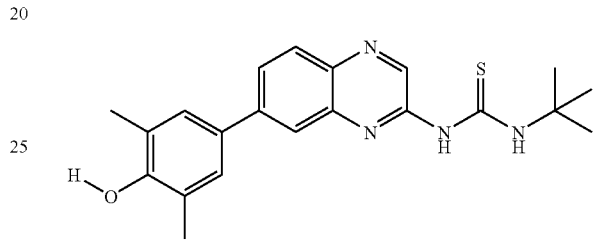

1-dodecyl-3-(7-phenylquinoxalin-2-yl)urea

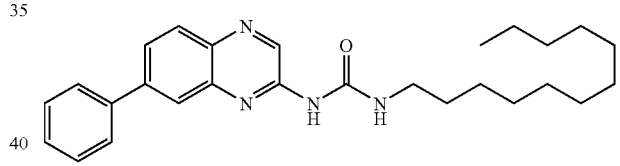

1-allyl-3-(7-phenylquinoxalin-2-yl)urea

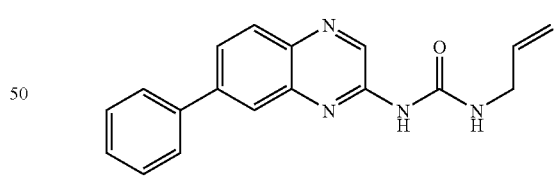

1-cyclopentyl-3-(7-phenylquinoxalin-2-yl)urea

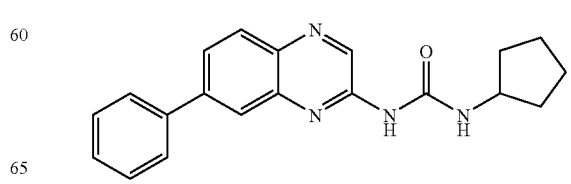

61

1-[7-(4-hydroxy-3,5-dimethylphenyl)quinoxalin-2-yl]-3-isopropylthiourea

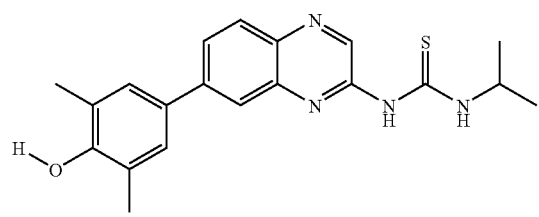

1-butyl-3-[7-(4-hydroxy-3,5-dimethylphenyl)quinoxalin-2-yl]thiourea

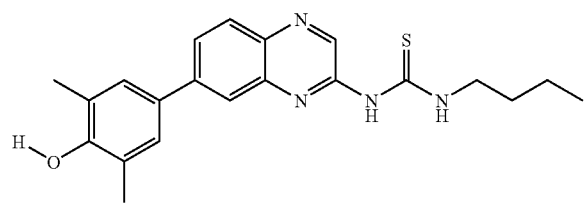

1-[7-(4-hydroxy-3,5-dimethylphenyl)quinoxalin-2-yl]-3-pentylurea

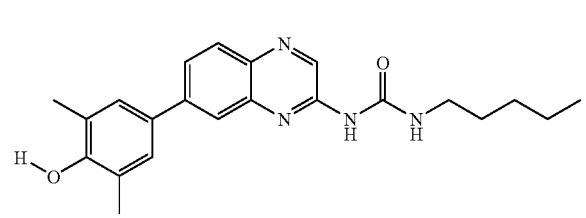 [SMILES: CCCCCNC(=O)Nc1cnc2ccc(-c3cc(C)c(O)c(C)c3)cc2n1]

1-cyclobutyl-3-[7-(4-hydroxy-3,5-dimethylphenyl)quinoxalin-2-yl]thiourea

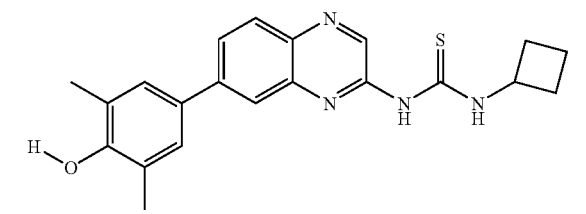 [SMILES: Cc1cc(-c2ccc3ncc(NC(=S)NC4CCC4)nc3c2)cc(C)c1O]

1-hexyl-3-[7-(4-hydroxy-3,5-dimethylphenyl)quinoxalin-2-yl]urea

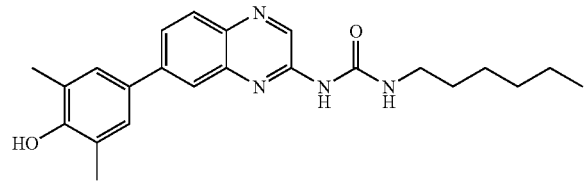 [SMILES: CCCCCCNC(=O)Nc1cnc2ccc(-c3cc(C)c(O)c(C)c3)cc2n1]

62

1-[7-(4-hydroxy-3,5-dimethylphenyl)quinoxalin-2-yl]-3-propylurea

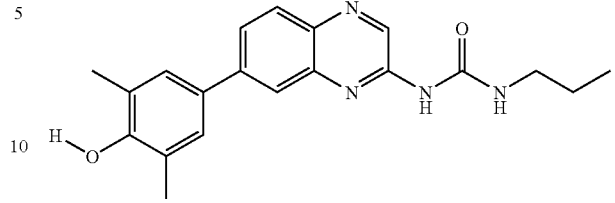

1-dodecyl-3-[7-(4-hydroxy-3,5-dimethylphenyl)quinoxalin-2-yl]urea

1-allyl-3-[7-(4-hydroxy-3,5-dimethylphenyl)quinoxalin-2-yl]urea

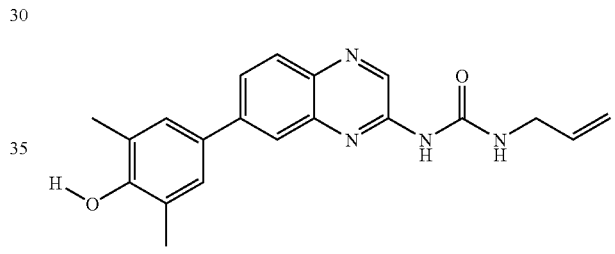

1-cyclooctyl-3-[7-(4-hydroxy-3,5-dimethylphenyl)quinoxalin-2-yl]urea

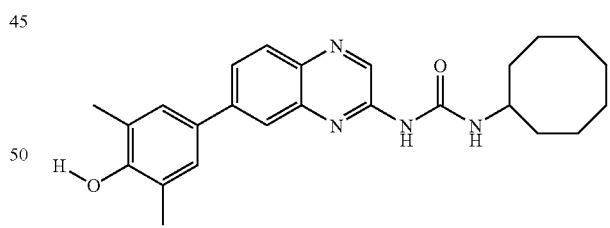

1-cyclooctyl-3-[7-(4-hydroxy-3-methoxyphenyl)quinoxalin-2-yl]urea

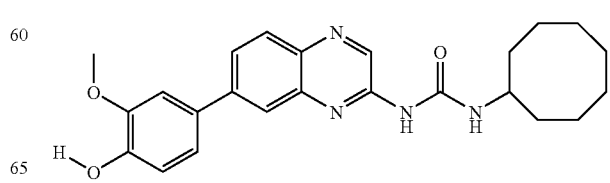

| 63 | 64 |
|---|---|
| 1-adamantan-1-yl-3-(7-phenylquinoxalin-2-yl)urea | 1-((S)-2-phenylcyclopropyl)-3-(7-phenylquinoxalin-2-yl)urea |

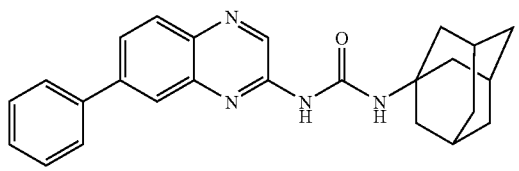 [SMILES: O=C(Nc1cnc2ccc(-c3ccccc3)cc2n1)NC12CC3CC(CC(C3)C1)C2]

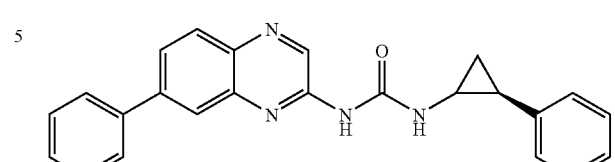

1-adamantan-1-yl-3-[7-(4-hydroxy-3,5-dimethylphenyl)quinoxalin-2-yl]urea

1-[7-(4-hydroxy-3,5-dimethylphenyl)quinoxalin-2-yl]-3-((S)-2-phenyl-cyclopropyl)urea

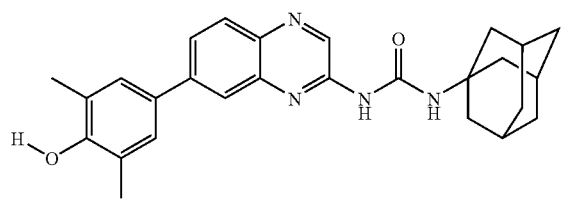 [SMILES: Cc1cc(-c2ccc3ncc(NC(=O)NC45CC6CC(CC(C6)C4)C5)nc3c2)cc(C)c1O]

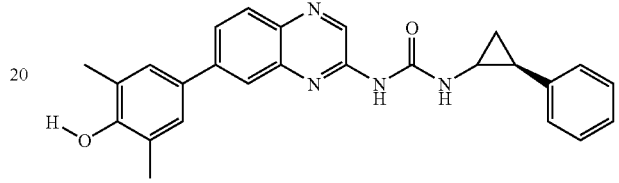

1-[7-(4-hydroxy-3,5-dimethylphenyl)quinoxalin-2-yl]-3-(1,1,3,3-tetramethyl-butyl)urea 1-allyl-3-[7-(4-hydroxy-3-methoxyphenyl)quinoxalin-2-yl]urea

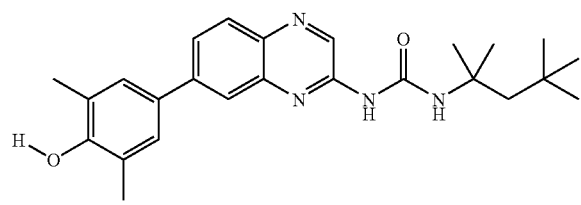 [SMILES: Cc1cc(-c2ccc3ncc(NC(=O)NC(C)(C)CC(C)(C)C)nc3c2)cc(C)c1O]

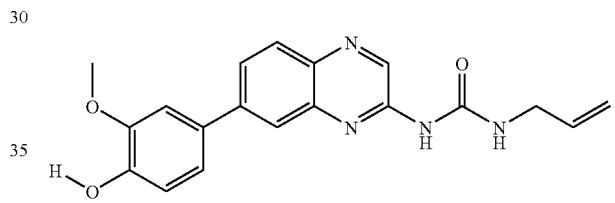

1-((R)-1,2-dimethylpropyl)-3-[7-(4-hydroxy-3,5-dimethylphenyl)quinoxalin-2-yl]urea 1-sec-butyl-3-[7-(4-hydroxy-3,5-dimethylphenyl)quinoxalin-2-yl]urea

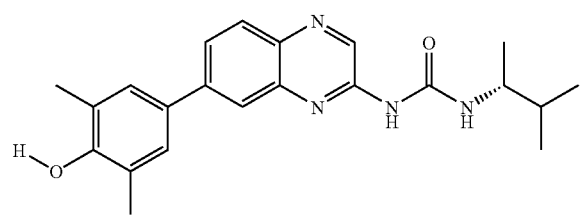

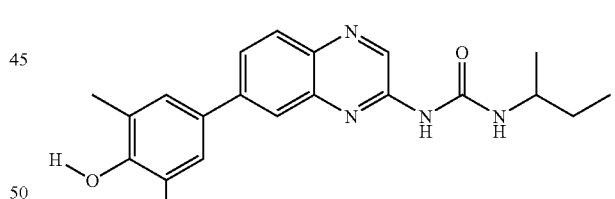

1-((S)-1,2-dimethylpropyl)-3-[7-(4-hydroxy-3,5-dimethylphenyl)quinoxalin-2-yl]urea 1-ethyl-3-[7-(4-methoxy-3,5-dimethylphenyl)quinoxalin-2-yl]urea

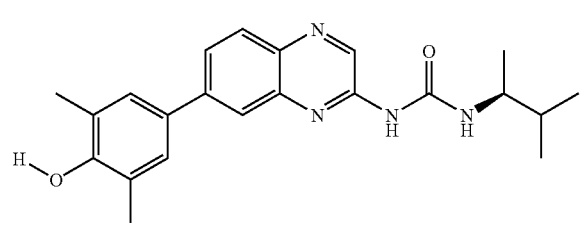 [SMILES: Cc1cc(-c2ccc3ncc(NC(=O)N[C@@H](C)C(C)C)nc3c2)cc(C)c1O]

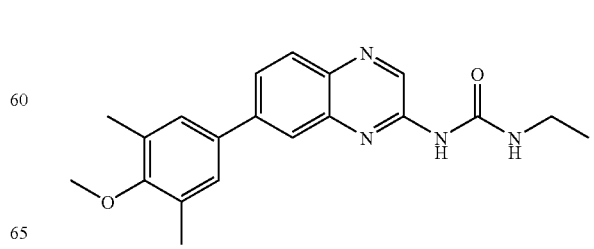

65

1-isopropyl-3-[7-(4-methoxy-3,5-dimethylphenyl)qui-noxalin-2-yl]urea

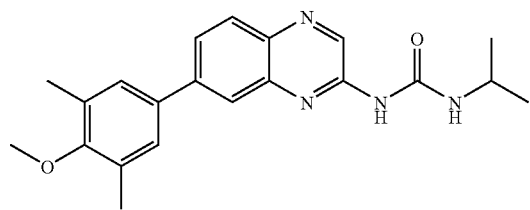

1-isopropyl-3-[7-(4-methoxy-3,5-dimethylphenyl)qui-noxalin-2-yl]thiourea

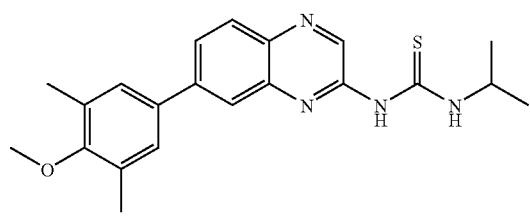

1-[7-(4-hydroxy-3,5-dimethylphenyl)quinoxalin-2-yl]-3-isobutylurea

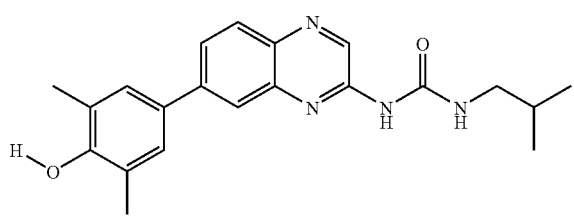 [SMILES: Cc1cc(-c2ccc3ncc(NC(=O)NCC(C)C)nc3c2)cc(C)c1O]

1-(1-ethylpropyl)-3-[7-(4-hydroxy-3,5-dimethylphenyl)quinoxalin-2-yl]urea

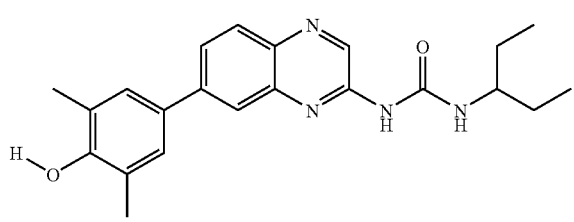 [SMILES: CCC(CC)NC(=O)Nc1cnc2ccc(-c3cc(C)c(O)c(C)c3)cc2n1]

1-(2,2-Dimethyl-propyl)-3-[7-(4-hydroxy-3,5-dimethyl-phenyl)-quinoxalin-2-yl]-urea

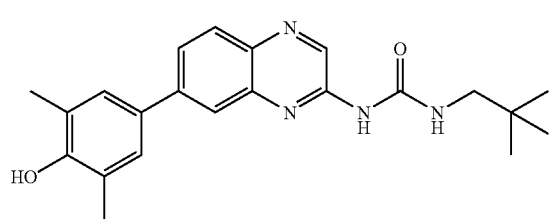 [SMILES: Cc1cc(-c2ccc3ncc(NC(=O)NCC(C)(C)C)nc3c2)cc(C)c1O]

66

1-[7-(4-Amino-phenyl)-quinoxalin-2-yl]-3-isopropyl-urea

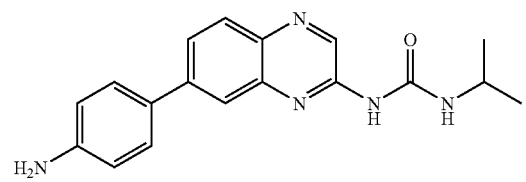 [SMILES: CC(C)NC(=O)Nc1cnc2ccc(-c3ccc(N)cc3)cc2n1]

1-[7-(4-Hydroxy-phenyl)-quinoxalin-2-yl]-3-isopropyl-urea

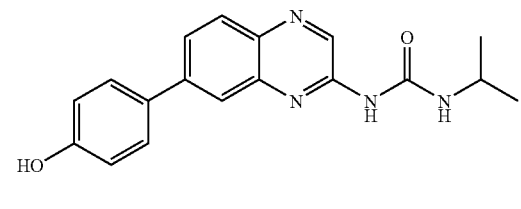 [SMILES: CC(C)NC(=O)Nc1cnc2ccc(-c3ccc(O)cc3)cc2n1]

1-Isopropyl-3-[7-(1-methyl-1H-pyrazol-4-yl)-quinoxa-lin-2-yl]-urea

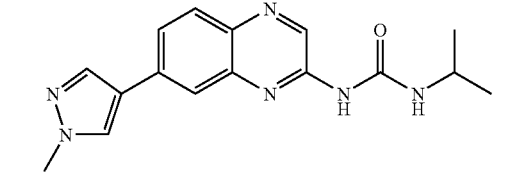 [SMILES: CC(C)NC(=O)Nc1cnc2ccc(-c3cnn(C)c3)cc2n1]

1-[7-(3,5-Dichloro-4-hydroxy-phenyl)-quinoxalin-2-yl]-3-pentyl-urea

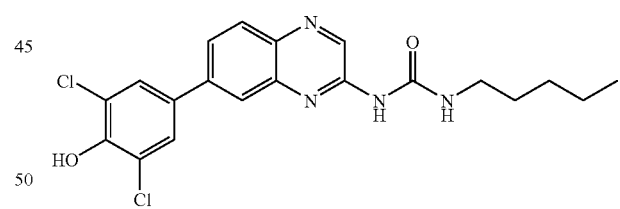

1-Butyl-3-[7-(3,5-dichloro-4-hydroxy-phenyl)-quinoxa-lin-2-yl]-urea

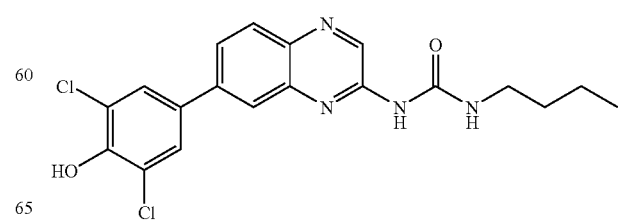

67

1-[7-(3,5-Dichloro-4-hydroxy-phenyl)-quinoxalin-2-yl]-3-propyl-urea

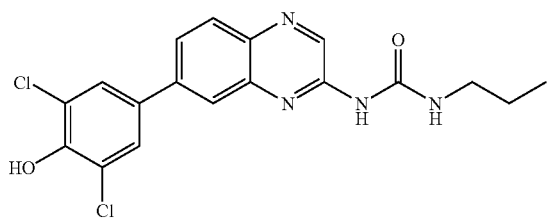

1-[7-(3,5-Dichloro-4-hydroxy-phenyl)-quinoxalin-2-yl]-3-ethyl-urea

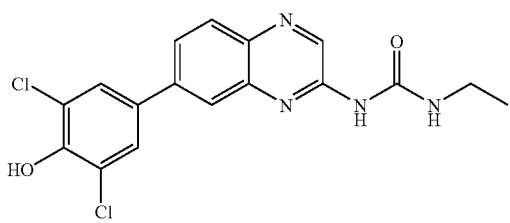

1-[7-(3,5-Dichloro-4-hydroxy-phenyl)-quinoxalin-2-yl]-3-heptyl-urea

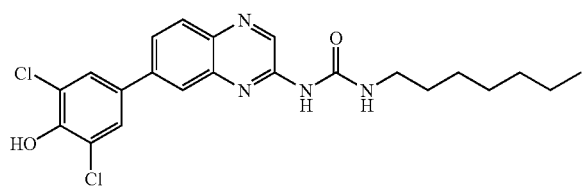 [SMILES: CCCCCCCNC(=O)Nc1cnc2ccc(-c3cc(Cl)c(O)c(Cl)c3)cc2n1]

1-[7-(3,5-Dichloro-4-hydroxy-phenyl)-quinoxalin-2-yl]-3-isopropyl-urea

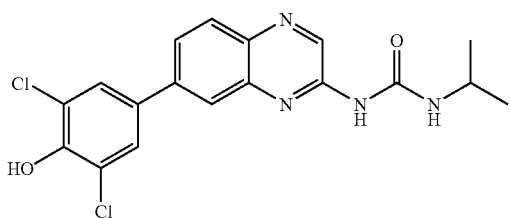 [SMILES: CC(C)NC(=O)Nc1cnc2ccc(-c3cc(Cl)c(O)c(Cl)c3)cc2n1]

1-tert-Butyl-3-[7-(3,5-dichloro-4-hydroxy-phenyl)-quinoxalin-2-yl]-urea

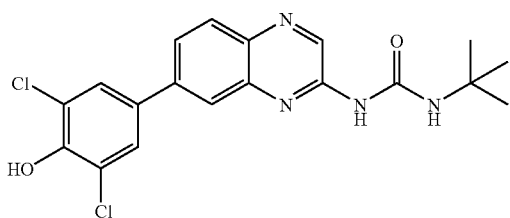 [SMILES: CC(C)(C)NC(=O)Nc1cnc2ccc(-c3cc(Cl)c(O)c(Cl)c3)cc2n1]

68

1-Cycloheptyl-3-[7-(3,5-dichloro-4-hydroxy-phenyl)-quinoxalin-2-yl]-urea

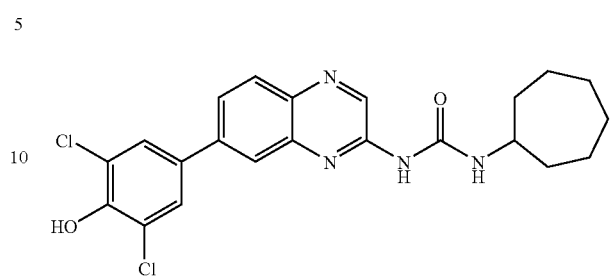

1-Cyclooctyl-3-[7-(3,5-dichloro-4-hydroxy-phenyl)-quinoxalin-2-yl]-urea

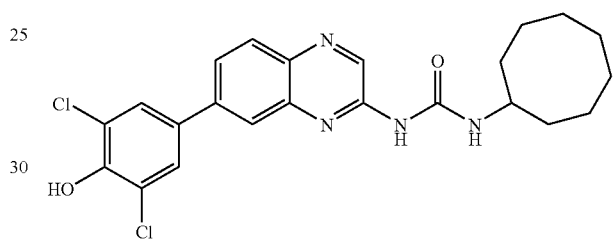

1-Cyclobutyl-3-[7-(3,5-dichloro-4-hydroxy-phenyl)-quinoxalin-2-yl]-thiourea

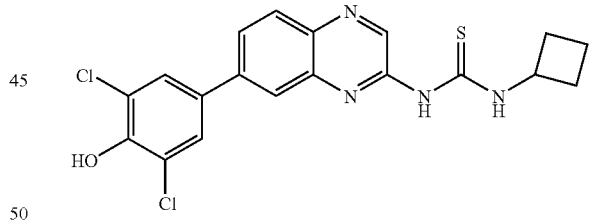

1-Cyclopentyl-3-[7-(3,5-dichloro-4-hydroxy-phenyl)-quinoxalin-2-yl]-urea

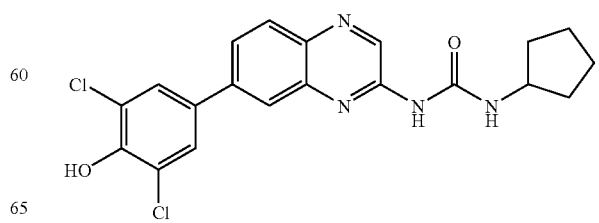

1-[7-(3-Chloro-4-hydroxy-5-methoxy-phenyl)-quinoxalin-2-yl]-3-isopropyl-urea

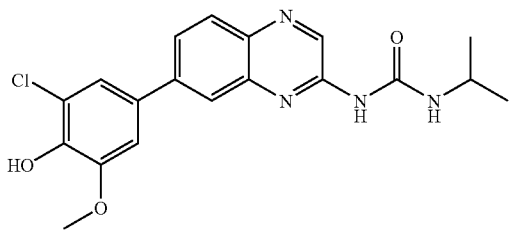 [SMILES: COc1cc(-c2ccc3ncc(NC(=O)NC(C)C)nc3c2)cc(Cl)c1O]

1-Cyclopropyl-3-[7-(3,5-dichloro-4-hydroxy-phenyl)-quinoxalin-2-yl]-thiourea

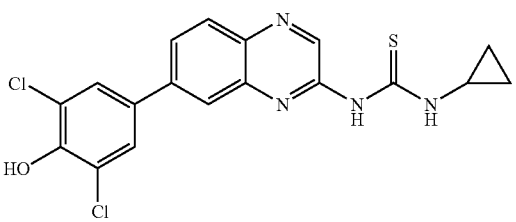 [SMILES: Oc1c(Cl)cc(-c2ccc3ncc(NC(=S)NC4CC4)nc3c2)cc1Cl]

1-[7-(3,5-Dichloro-4-hydroxy-phenyl)-quinoxalin-2-yl]-3-(3-phenyl-propyl)-urea

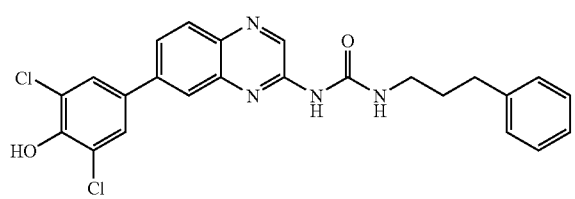

1-[7-(3,5-Dichloro-4-hydroxy-phenyl)-quinoxalin-2-yl]-3-phenethyl-urea

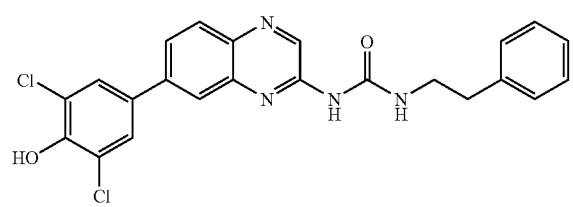 [SMILES: O=C(NCCc1ccccc1)Nc1cnc2ccc(-c3cc(Cl)c(O)c(Cl)c3)cc2n1]

1-Butyl-3-[7-(3,5-dichloro-4-hydroxy-phenyl)-quinoxalin-2-yl]-thiourea

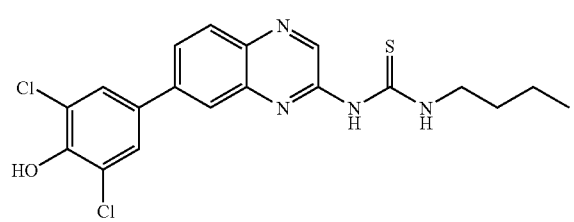 [SMILES: CCCCNC(=S)Nc1cnc2ccc(-c3cc(Cl)c(O)c(Cl)c3)cc2n1]

1-[7-(3,5-Dichloro-4-hydroxy-phenyl)-quinoxalin-2-yl]-3-ethyl-thiourea

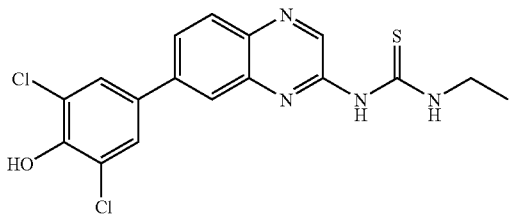

1-[7-(3,5-Dichloro-4-hydroxy-phenyl)-quinoxalin-2-yl]-3-propyl-thiourea

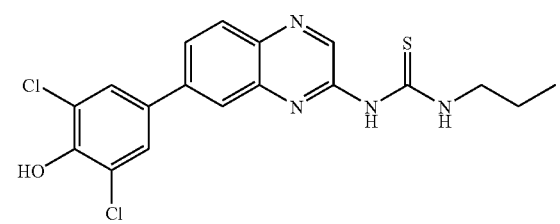

1-[7-(3,5-Dichloro-4-hydroxy-phenyl)-quinoxalin-2-yl]-3-pentyl-thiourea

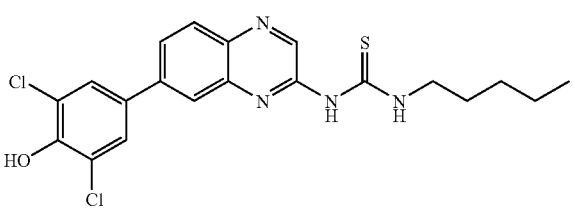 [SMILES: CCCCCNC(=S)Nc1cnc2ccc(-c3cc(Cl)c(O)c(Cl)c3)cc2n1]

1-[7-(3,5-Dichloro-4-hydroxy-phenyl)-quinoxalin-2-yl]-3-isopropyl-thiourea

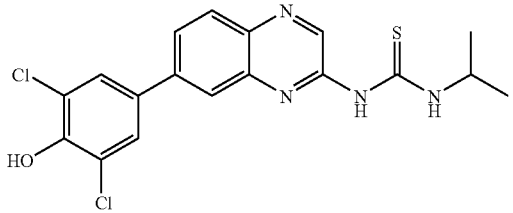

1-Cycloheptyl-3-[7-(3,5-dichloro-4-hydroxy-phenyl)-quinoxalin-2-yl]-thiourea

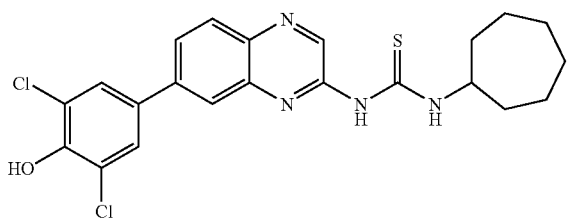

| 71 | 72 |
|---|---|
| 1-Cyclooctyl-3-[7-(3,5-dichloro-4-hydroxy-phenyl)-quinoxalin-2-yl]-thiourea | 1-[2-(4-Chloro-phenyl)-ethyl]-3-[7-(3,5-dichloro-4-hydroxy-phenyl)-quinoxalin-2-yl]-thiourea |

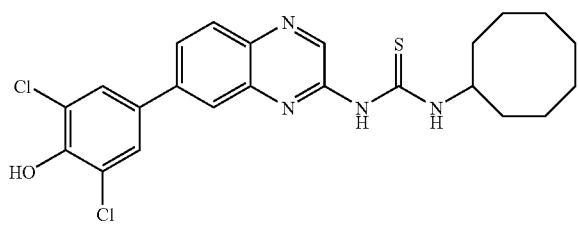 [SMILES: Oc1c(Cl)cc(-c2ccc3ncc(NC(=S)NC4CCCCCCC4)nc3c2)cc1Cl]

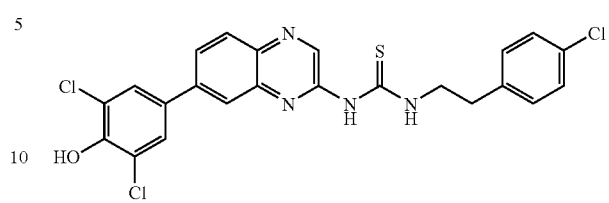

1-Benzyl-3-[7-(3,5-dichloro-4-hydroxy-phenyl)-quinoxalin-2-yl]-thiourea

1-[7-(3,5-Dichloro-4-hydroxy-phenyl)-quinoxalin-2-yl]-3-(3-morpholin-4-yl-propyl)-thiourea

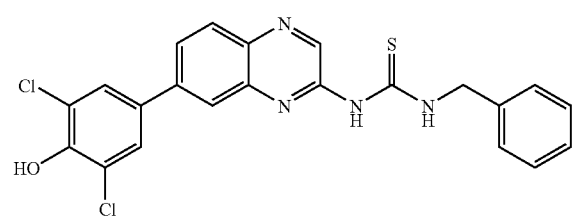 [SMILES: Oc1c(Cl)cc(-c2ccc3ncc(NC(=S)NCc4ccccc4)nc3c2)cc1Cl]

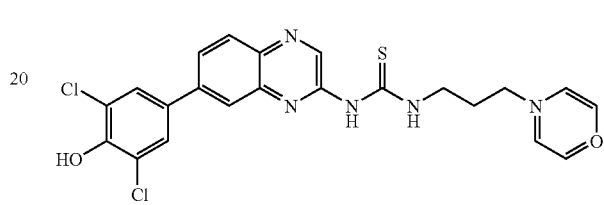

1-[7-(3-Chloro-4-hydroxy-phenyl)-quinoxalin-2-yl]-3-isopropyl-urea

1-[7-(3,5-Dichloro-4-hydroxy-phenyl)-quinoxalin-2-yl]-3-[2-(3,4-dimethoxy-phenyl)-ethyl]-thiourea

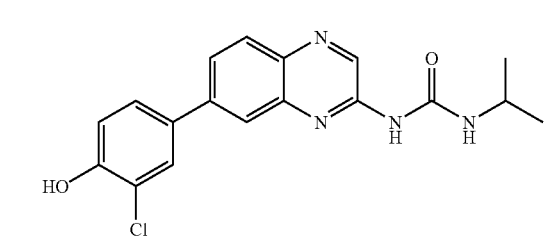 [SMILES: CC(C)NC(=O)Nc1cnc2ccc(-c3ccc(O)c(Cl)c3)cc2n1]

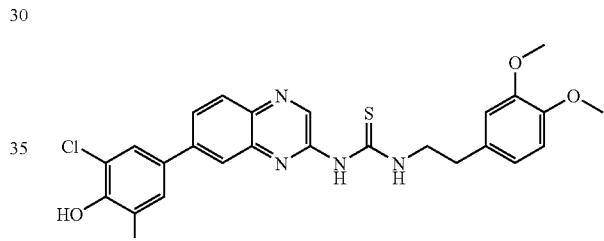

1-[7-(3,5-Dichloro-4-hydroxy-phenyl)-quinoxalin-2-yl]-3-(3-phenyl-propyl)-thiourea 1-(2-Cyclohex-1-enyl-ethyl)-3-[7-(3,5-dichloro-4-hydroxy-phenyl)-quinoxalin-2-yl]-thiourea

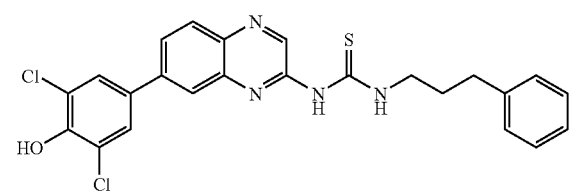

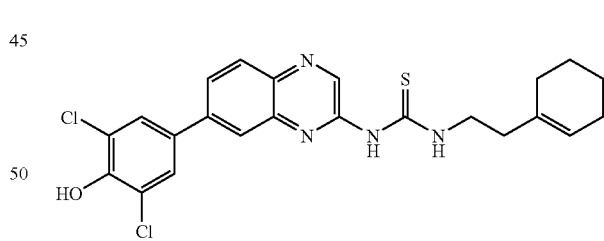

1-[7-(3,5-Dichloro-4-hydroxy-phenyl)-quinoxalin-2-yl]-3-phenethyl-thiourea

1-[7-(3,5-Dichloro-4-hydroxy-phenyl)-quinoxalin-2-yl]-3-(2-thiophen-2-yl-ethyl)-urea

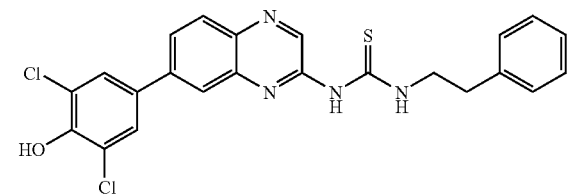

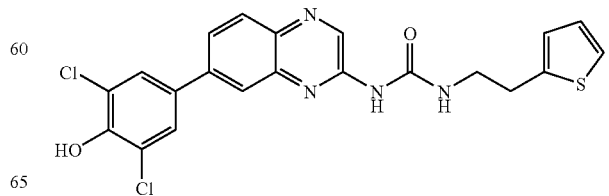

73

1-[7-(3,5-Dichloro-4-hydroxy-phenyl)-quinoxalin-2-yl]-3-[2-(4-methoxy-phenyl)-ethyl]-thiourea

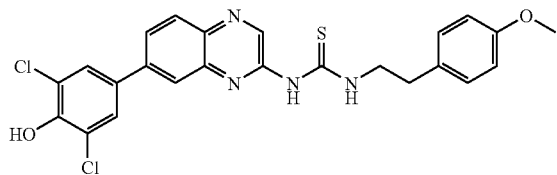

1-[7-(3,5-Dichloro-4-hydroxy-phenyl)-quinoxalin-2-yl]-3-[2-(4-ethyl-phenyl)-ethyl]-urea

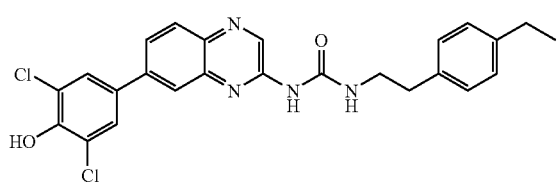

1-[7-(3,5-Dichloro-4-hydroxy-phenyl)-quinoxalin-2-yl]-3-[2-(3,5-dimethoxy-phenyl)-ethyl]-urea

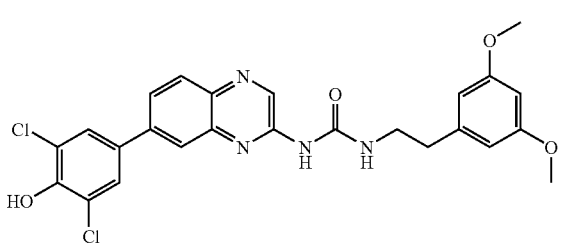 [SMILES: COc1cc(CCNC(=O)Nc2cnc3ccc(-c4cc(Cl)c(O)c(Cl)c4)cc3n2)cc(OC)c1]

1-[7-(3,5-Dichloro-4-hydroxy-phenyl)-quinoxalin-2-yl]-3-[2-(3,4-dichloro-phenyl)-ethyl]-urea

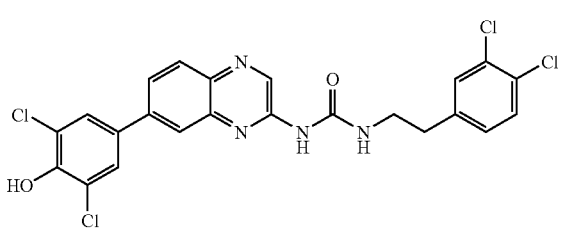 [SMILES: O=C(NCCc1ccc(Cl)c(Cl)c1)Nc1cnc2ccc(-c3cc(Cl)c(O)c(Cl)c3)cc2n1]

1-[2-(3-Bromo-4-methoxy-phenyl)-ethyl]-3-[7-(3,5-dichloro-4-hydroxy-phenyl)-quinoxalin-2-yl]-urea

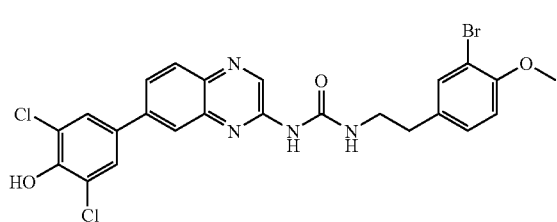 [SMILES: COc1ccc(CCNC(=O)Nc2cnc3ccc(-c4cc(Cl)c(O)c(Cl)c4)cc3n2)cc1Br]

74

1-(2-Biphenyl-4-yl-ethyl)-3-[7-(3,5-dichloro-4-hydroxy-phenyl)-quinoxalin-2-yl]-urea

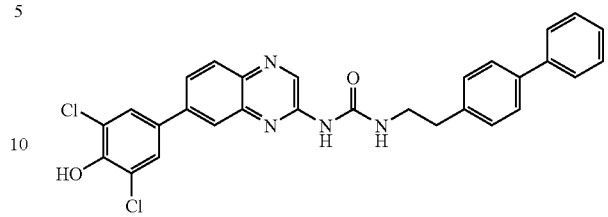

1-[7-(3,5-Dichloro-4-hydroxy-phenyl)-quinoxalin-2-yl]-3-[2-(2,3-dimethoxy-phenyl)-ethyl]-urea

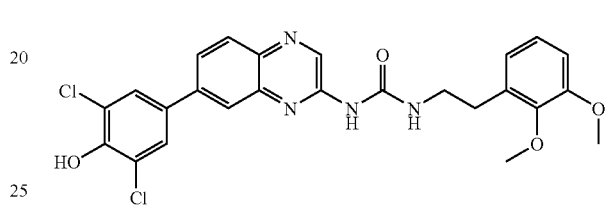

1-[7-(3,5-Dichloro-4-hydroxy-phenyl)-quinoxalin-2-yl]-3-[2-(2-fluoro-phenyl)-ethyl]-urea

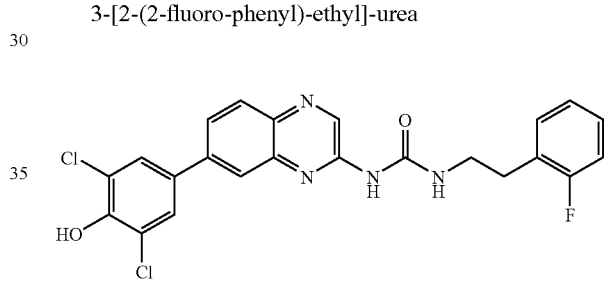

1-[7-(3,5-Dichloro-4-hydroxy-phenyl)-quinoxalin-2-yl]-3-[2-(2,4-dichloro-phenyl)-ethyl]-urea

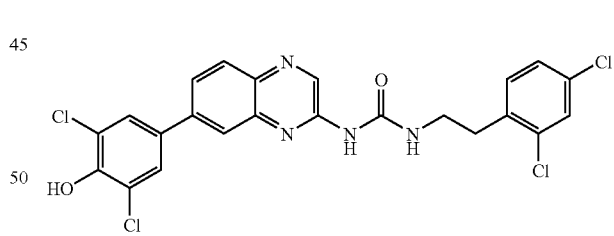

1-[7-(3,5-Dichloro-4-hydroxy-phenyl)-quinoxalin-2-yl]-3-[2-(4-fluoro-phenyl)-ethyl]-urea

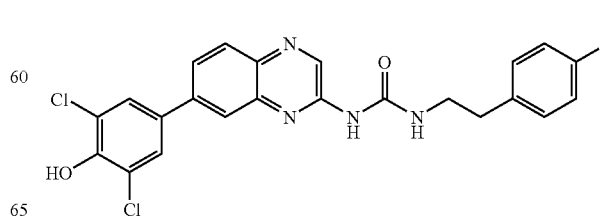

75

1-[7-(3,5-Dichloro-4-hydroxy-phenyl)-quinoxalin-2-yl]-3-[2-(3,4-dimethoxy-phenyl)-ethyl]-urea

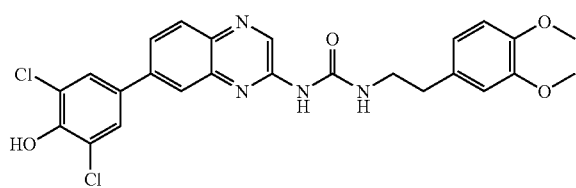 [SMILES: COc1ccc(CCNC(=O)Nc2cnc3ccc(-c4cc(Cl)c(O)c(Cl)c4)cc3n2)cc1OC]

1-[7-(3,5-Dichloro-4-hydroxy-phenyl)-quinoxalin-2-yl]-3-[2-(4-methoxy-phenyl)-ethyl]-urea

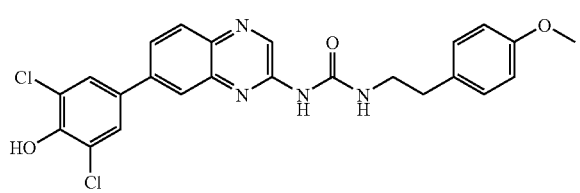 [SMILES: COc1ccc(CCNC(=O)Nc2cnc3ccc(-c4cc(Cl)c(O)c(Cl)c4)cc3n2)cc1]

1-[7-(3,5-Dichloro-4-hydroxy-phenyl)-quinoxalin-2-yl]-3-[2-(2,5-dimethoxy-phenyl)-ethyl]-urea

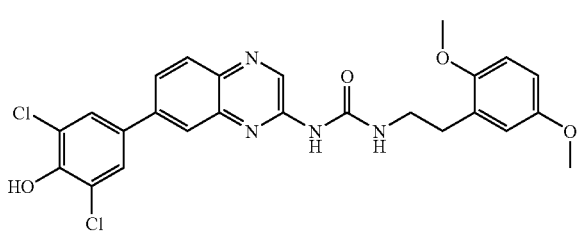 [SMILES: COc1ccc(OC)c(CCNC(=O)Nc2cnc3ccc(-c4cc(Cl)c(O)c(Cl)c4)cc3n2)c1]

1-[2-(4-Chloro-phenyl)-ethyl]-3-[7-(3,5-dichloro-4-hydroxy-phenyl)-quinoxalin-2-yl]-urea

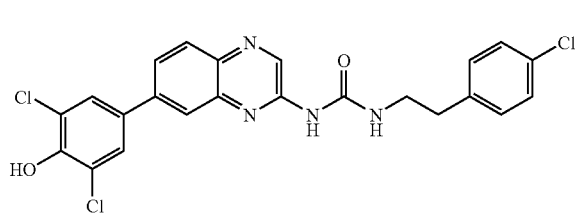 [SMILES: O=C(NCCc1ccc(Cl)cc1)Nc1cnc2ccc(-c3cc(Cl)c(O)c(Cl)c3)cc2n1]

1-[2-(3-Chloro-phenyl)-ethyl]-3-[7-(3,5-dichloro-4-hydroxy-phenyl)-quinoxalin-2-yl]-urea

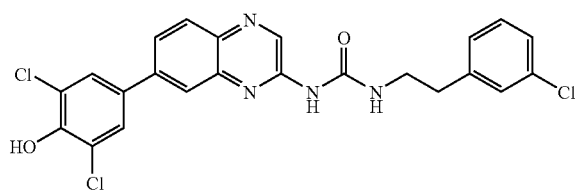 [SMILES: O=C(NCCc1cccc(Cl)c1)Nc1cnc2ccc(-c3cc(Cl)c(O)c(Cl)c3)cc2n1]

76

1-(2-Cyclopentyl-ethyl)-3-[7-(3,5-dichloro-4-hydroxy-phenyl)-quinoxalin-2-yl]-thiourea

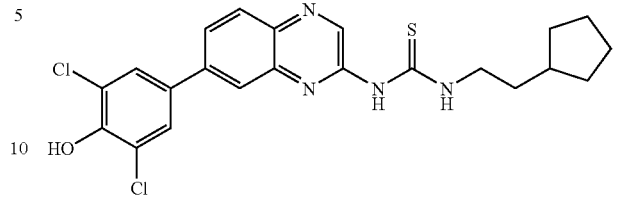

1-(2-Cyclohexyl-ethyl)-3-[7-(3,5-dichloro-4-hydroxy-phenyl)-quinoxalin-2-yl]-urea

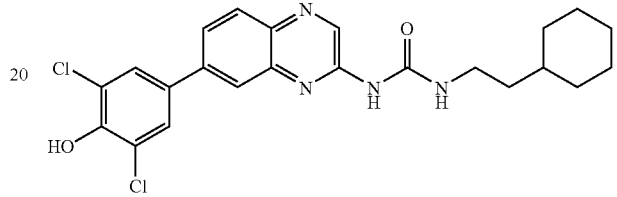

1-(2-Cyclohexyl-ethyl)-3-[7-(3,5-dichloro-4-hydroxy-phenyl)-quinoxalin-2-yl]-thiourea

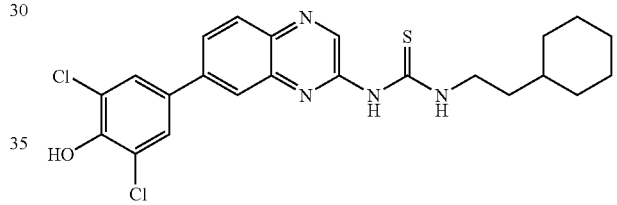

1-[7-(3,5-Dichloro-4-hydroxy-phenyl)-quinoxalin-2-yl]-3-[2-(4-hydroxy-phenyl)-ethyl]-thiourea

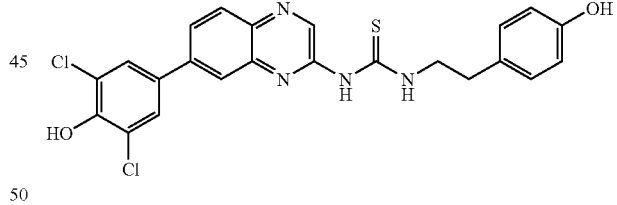

1-[7-(3,5-Dichloro-4-hydroxy-phenyl)-quinoxalin-2-yl]-3-(2-pyridin-3-yl-ethyl)-thiourea

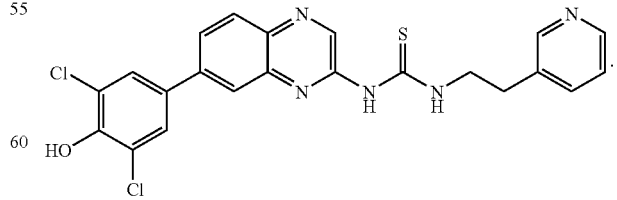

9. A pharmaceutical composition comprising a pharmacologically active amount of at least one compound according to claim 1 and a pharmaceutically acceptable carrier, auxiliary and/or excipient.

10. A pharmaceutical composition comprising a pharmacologically active amount of at least one compound according to claim 8 and a pharmaceutically acceptable carrier, auxiliary and/or excipient.

11. A process for preparing a pharmaceutical composition according to claim 9, comprising admixing a pharmacologically active amount of at least one compound according to claim 1 with at least one pharmaceutically acceptable carrier, auxiliary and/or excipient.

12. A process for preparing a pharmaceutical composition according to claim 10, comprising admixing a pharmacologically active amount of at least one compound according to claim 8 with at least one pharmaceutically acceptable carrier, auxiliary and/or excipient.

* * * * *